US009913862B2

(12) United States Patent
Collins et al.

(10) Patent No.: US 9,913,862 B2
(45) Date of Patent: Mar. 13, 2018

(54) METHODS OF TREATING GRAM-NEGATIVE MICROBIAL INFECTIONS

(71) Applicant: TRUSTEES OF BOSTON UNIVERSITY, Boston, MA (US)

(72) Inventors: James J. Collins, Newton, MA (US); J. Ruben Morones-Ramirez, Nuevo Leon (MX); Jonathan Alexander Winkler, Brighton, MA (US); Catherine S. Spina, Boston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 14/354,440

(22) PCT Filed: Oct. 26, 2012

(86) PCT No.: PCT/US2012/062138
§ 371 (c)(1),
(2) Date: Apr. 25, 2014

(87) PCT Pub. No.: WO2013/063405
PCT Pub. Date: May 2, 2013

(65) Prior Publication Data
US 2014/0308367 A1 Oct. 16, 2014

Related U.S. Application Data

(60) Provisional application No. 61/551,649, filed on Oct. 26, 2011.

(51) Int. Cl.
| A61K 33/38 | (2006.01) |
| C12N 1/20 | (2006.01) |
| A61K 38/17 | (2006.01) |
| A61K 31/28 | (2006.01) |
| A61K 38/12 | (2006.01) |
| A61K 38/14 | (2006.01) |
| A61K 45/06 | (2006.01) |

(52) U.S. Cl.
CPC ............ *A61K 33/38* (2013.01); *A61K 38/12* (2013.01); *A61K 38/14* (2013.01); *A61K 45/06* (2013.01)

(58) Field of Classification Search
None
See application file for complete search history.

(56) References Cited

U.S. PATENT DOCUMENTS

| 4,404,197 | A |  | 9/1983 | Fox, Jr. et al. |
| 5,374,432 | A |  | 12/1994 | Fox, Jr. et al. |
| 6,582,719 | B2 |  | 6/2003 | Modak et al. |
| 7,601,731 | B2 |  | 10/2009 | Raad |
| 8,962,026 | B2 | * | 2/2015 | Baker, Jr. ............ A61K 9/1075 424/400 |
| 2003/0008012 | A1 |  | 1/2003 | Pena et al. |
| 2005/0013836 | A1 |  | 1/2005 | Raad |
| 2005/0202066 | A1 | * | 9/2005 | Arata .................. A01N 31/02 424/443 |
| 2006/0269485 | A1 |  | 11/2006 | Friedman et al. |
| 2010/0272769 | A1 |  | 10/2010 | Darlington, Jr. et al. |

FOREIGN PATENT DOCUMENTS

WO WO 2010/036938 A2 * 4/2010 ............. A61P 11/00

OTHER PUBLICATIONS

Morones et al.; Nanotechnology (2005) 16; pp. 2346-2353.*
Sondi et al.; J. Colloid and Interface Science 275 (2004); pp. 177-182.*
Lok et al.; J. of Proteome Research (2006), 5, pp. 916-924.*
Ag Koloidna Srebrna Voda, Clinical Center of Serbia Urology Clinic "Influence of the Use of Colloidal Silver Water as Adjuvant Preparation in Treatment of Urinary Infections Manufacturer: "EKO SOLAR" D.O.O. Belgrade, Svetog Save St. No. 34", http://www.srebrna-voda.rs/english/misljenja4.php, Sep. 12, 2011, 3 pp.
Fayaz et al., "Biogenic synthesis of silver nanoparticles and their synergistic effect with antibiotics: a study against gram-positive and gram-negative bacteria", Nanomedicine: Nanotechnology, Biology, and Medicine, vol. 6, Iss. 1, pp. 103-109, 2010.
Humphreys et al., "Combinatorial activities of ionic silver and sodium hexannetaphosphate against microorganisms associated with chronic wounds", J. Antimicrob. Chemother., vol. 66, Iss. 11, pp. 2556-2561, 2011.
Kim et al., "Antimicrobial effects of silver nanoparticles", Nanomedicine: Nanotechnology, Biology, and Medicine, vol. 3, Iss. 1, pp. 95-101, 2007.
Shrivastava et al., "Characterization of enhanced antibacterial effects of novel silver nanoparticles", Nanotechnology, vol. 18, pp. 1-9, 2007.
Baba et al., "Construction of *Escherichia coli* K-12 in-frame, single-gene knockout mutants: the Keio collection", Molecular Systems Biology 1-11(2006).
Chen et al., "The Antiproliferative and Differentiative Activities of 1,25-Dihydroxyvitamin D3 Are Potentiated by Epidermal Growth Factor and Attenuated by Insulin in Cultured Human Keratinocytes", Journal of Investigative Dermatology 104(1):113-117 (1995).
Chillappagari et al., "Copper Stress Affects Iron Homeostasis by Destabilizing Iron-Sulfur Cluster Formation in Bacillus subtilis", Journal of Bacteriology 192(10):2512-2524 (2010).
Cotter et al., "Aerobic regulation of cytochrome d oxidase (cydAB) operon expression in *Escherichia coli*: roles of Fnr and ArcA in repression and activation", Molecular Microbiology 25(3):605-615 (1997).

(Continued)

*Primary Examiner* — Jeffrey T Palenik
(74) *Attorney, Agent, or Firm* — Nixon Peabody LLP

(57) ABSTRACT

Provided herein are methods and compositions for treatment of a microbial infection or a microbial biofilm in a subject or on a surface by administering to the subject or surface determined to have or suspected of having a microbial infection/film an antimicrobial agent in combination with a silver-containing compound (e.g., a silver salt). In some embodiments, a silver-containing compound can increase activity of the antimicrobial agent. In other embodiments, addition of a silver-containing compound to an antimicrobial agent can expand the antimicrobial spectrum of the antimicrobial agent such that the antimicrobial agent originally indicated for treatment of one microbial strain (e.g., Gram-positive microbes) becomes effective for treating additional microbial strains (e.g., Gram-negative microbes). Other aspects relating to methods and compositions for delivering an agent to a microbe by increasing the membrane permeability of the microbe are also provided herein.

16 Claims, 21 Drawing Sheets

(56) References Cited

OTHER PUBLICATIONS

Denoncin et al., "The Protein-disulfide Isomerase DsbC Cooperates with SurA and DsbA in the Assembly of the Essential β-Barrel Protein LptD", The Journal Biological Chemistry 285(38):29425-29433 (2010).

Dwyer et al., "Gyrase inhibitors induce an oxidative damage cellular death pathway in *Escherichia coli*", Molecular Systems Biology 3:91 (2007). (15 pages).

Feng et al., "A mechanistic study of the antibacterial effect of silver ions on *Escherichia coli* and *Staphylococcus aureus*", Journal of Biomedical Materials Research 52:662-668 (2000).

Gordon et al., "Silver Coordination Polymers for Prevention of Implant Infection: Thiol Interaction, Impact on Respiratory Chain Enzymes, and Hydroxyl Radical Induction", Antimicrobial Agents and Chemotherapy 54 (10):4208-4218 (2010).

Hiraoka et al., "Rapid Assessment of the Physiological Status of the Polychlorinated Biphenyl Degrader Comamonas testosteroni TK102 by Flow Cytometry", Applied and Environmental Microbiology 68(4):2031-2035 (2002).

Holt et al., "Interaction of Silver(I) Ions with the Respiratory Chain of *Escherichia coli*: An Electrochemical and Scanning Electrochemical Microscopy Study of the Antimicrobial Mechanism of Micromolar Ag+", Biochemistry 44 (39):13214-13223 (2005).

Jung et al. "Antibacterial Activity and Mechanism of Action of the Silver Ion in *Staphylococcus aureus* and *Escherichia coli*", Applied and Environmental Microbiology 74(7):2171-2178 (2008).

Klippstein et al., "Silver nanoparticles interactions with the immune system: implications for health and disease", Silver Nanoparticles (2010). (18 pages).

Kohanski et al., "A Common Mechanism of Cellular Death Induced by Bactericidal Antibiotics", Cell 130:797-810 (2007).

Kohanski et al., "Mistranslation of Membrane Proteins and Two-Component System Activation Trigger Antibiotic-Mediated Cell Death", Cell 135:679-690 (2008).

Kohanski et al., "How antibiotics kill bacteria: from targets to networks", Nature Reviews-Microbiology 8(6):423-435 (2010).

Korshunov et al., "Two sources of endogenous hydrogen peroxide in *Escherichia coli*", Molecular Microbiology 75 (6):1389-1401 (2010).

Li et al., "Colistin: the re-emerging antibiotic for multidrug-resistant Gram-negative bacterial infections", The Lancet Infectious Diseases 6:589-601 (2006).

Liau et al., "Interaction of silver nitrate with readily identifiable groups: relationship to the antibacterial action of silver ions", Letters in Applied Microbiology 25:279-283 (1997).

Lutz et al., "Independent and tight regulation of transcriptional units in *Escherichia coli* via the LacR/O, the TetR/O and AraC/I1-I2 regulatory elements", Nucleic Acids Research 25(6):1203-1210 (1997).

Matsumoto et al., "Roles of SecG in ATP- and SecA-dependent protein translocation", Proceedings of the National Academy of Sciences USA 95:13567-13572 (1998).

Novo et al., "Multiparameter Flow Cytometric Analysis of Antibiotic Effects on Membrane Potential, Membrane Permeability, and Bacterial Counts of *Staphylococcus aureus* and *Micrococcus luteus*", Antimicrobial Agents and Chemotherapy 44(4):827-834 (2000).

Novogrodsky et al., "Hydroxyl radical scavengers inhibit lymphocyte mitogenesis", Proceedings of the National Academy of Sciences USA 79:1171-1174 (1982).

Pages et al., "The porin and the permeating antibiotic: A selective diffusion barrier in Gram-negative bacteria", Nature Reviews-Microbiology 6:893-903 (2008).

Park et al., "Silver-ion-mediated reactive oxygen species generation affecting bactericidal activity", Water Research 43:1027-1032(2009).

Schwartz et al., "The cysteine desulfurase, IscS, has a major role in in vivo Fe-S cluster formation in *Escherichia coli*", Proceedings of the National Academy of Sciences 97(16):9009-9014 (2000).

Setsukinai et al., "Development of Novel Fluorescence Probes That Can Reliably Detect Reactive Oxygen Species and Distinguish Specific Species", The Journal of Biological Chemistry 278(5):3170-3175 (2003).

Slawson et al., "Bacterial interactions with silver", Biology of Metals 3:151-154 (1990).

Taubes, "The Bacteria Fight Back", Science 321:356-361 (2008).

Thurman et al., "The Molecular Mechanisms of Copper and Silver Ion Disinfection of Bacteria and Viruses", Critical Reviews in Environmental Control 18(4):295-315 (1989).

Touati et al., "Lethal Oxidative Damage and Mutagenesis Are Generated by Iron in delta fur Mutants of *Escherichia coli*: Protective Role of Superoxide Dismutase", Journal of Bacteriology 177(9):2305-2314 (1995).

Zheng et al., "Activation of the OxyR Transcription Factor by Reversible Disulfide Bond Formation", Science 279:1718-1721 (1998).

\* cited by examiner

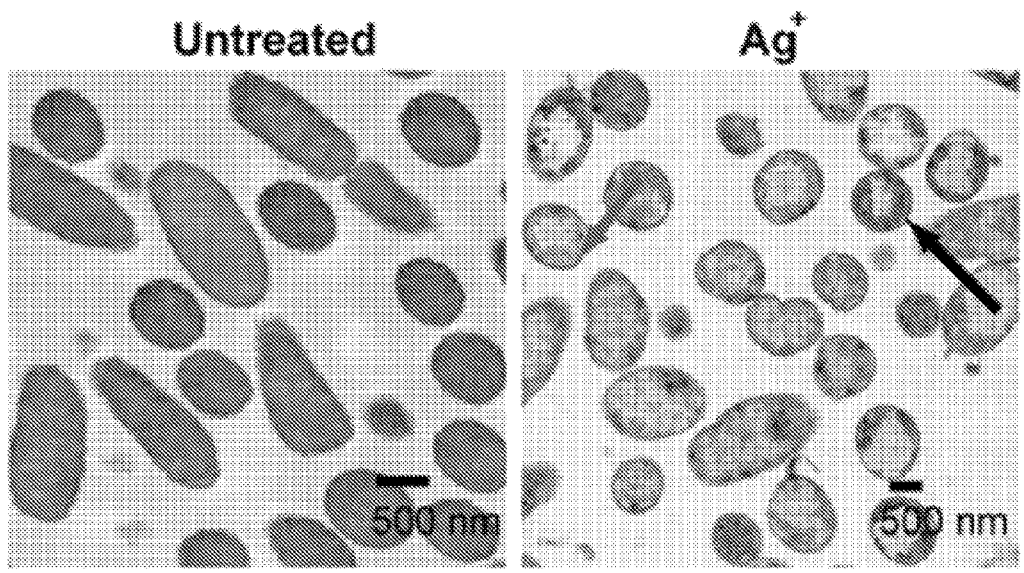
*FIG. 4A*
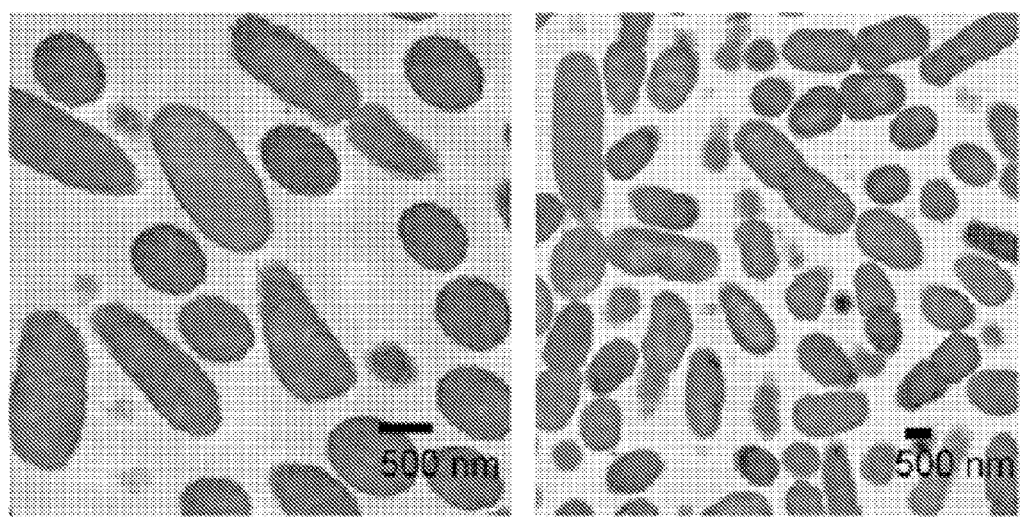
*FIG. 4B*  *FIG. 4C*

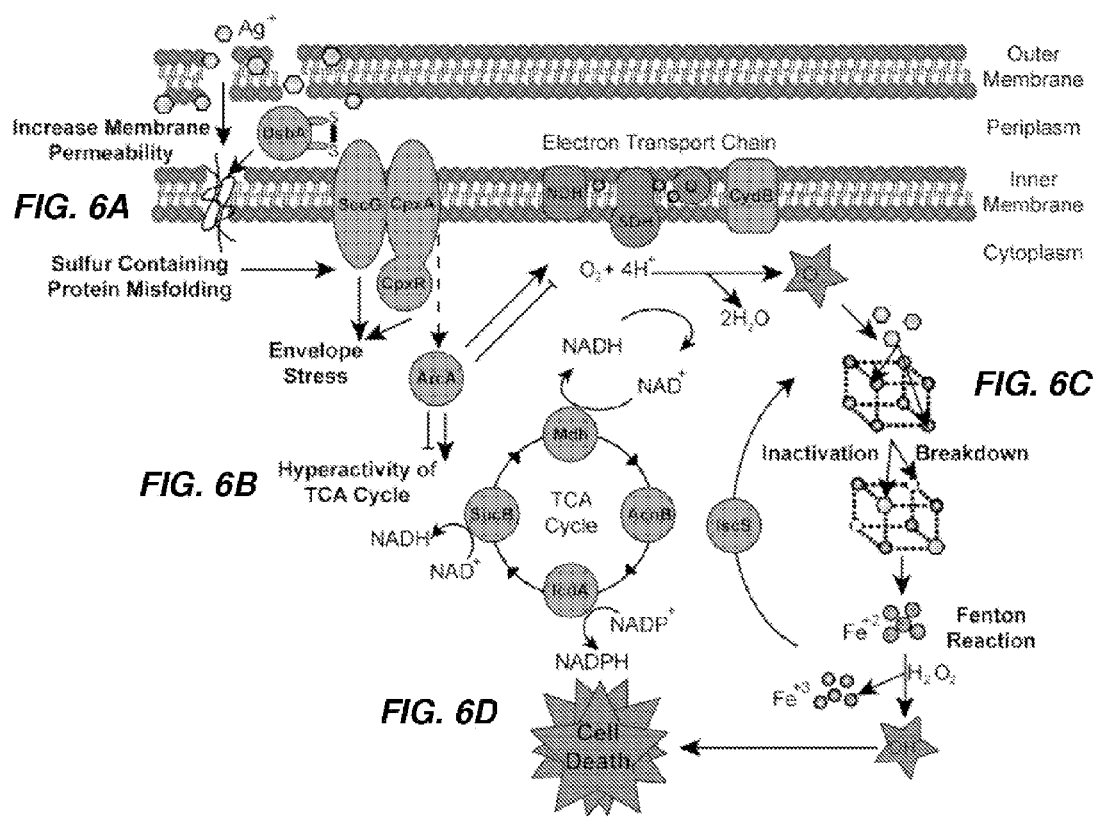

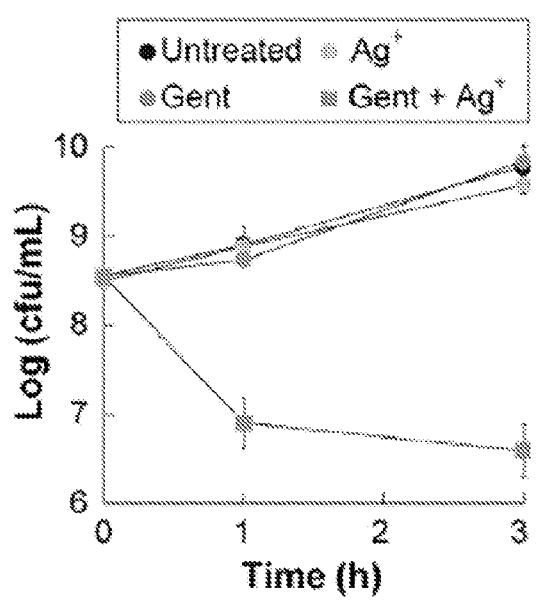
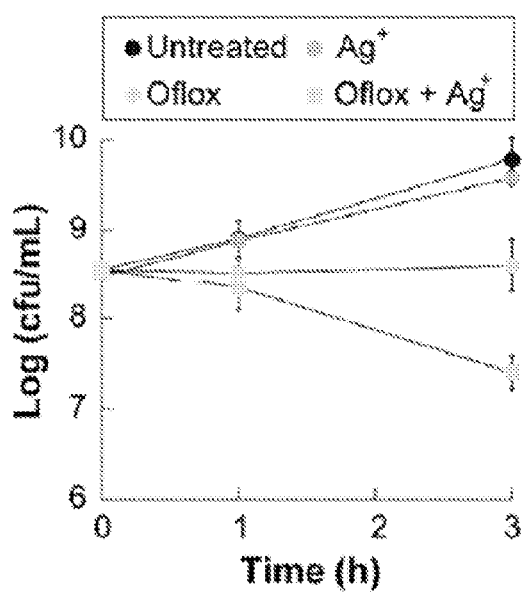
FIG. 7A                    FIG. 7B
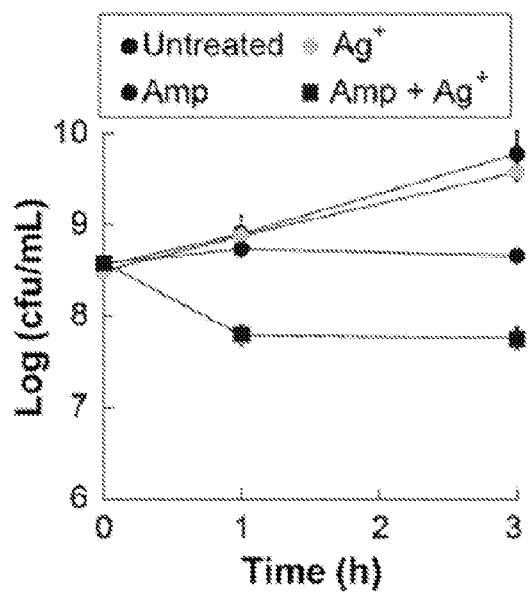
FIG. 7C

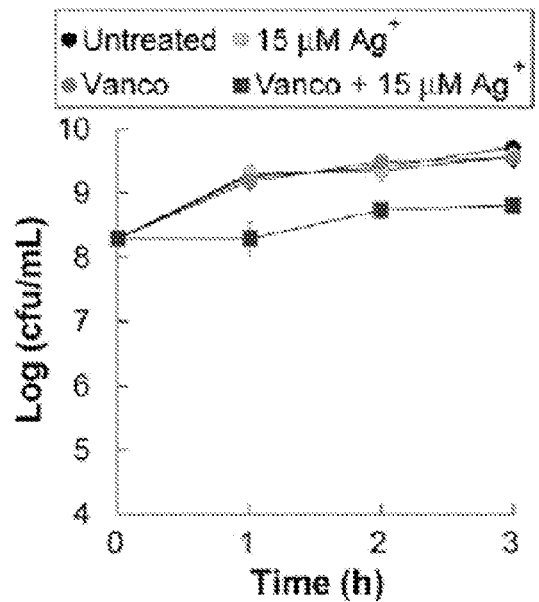 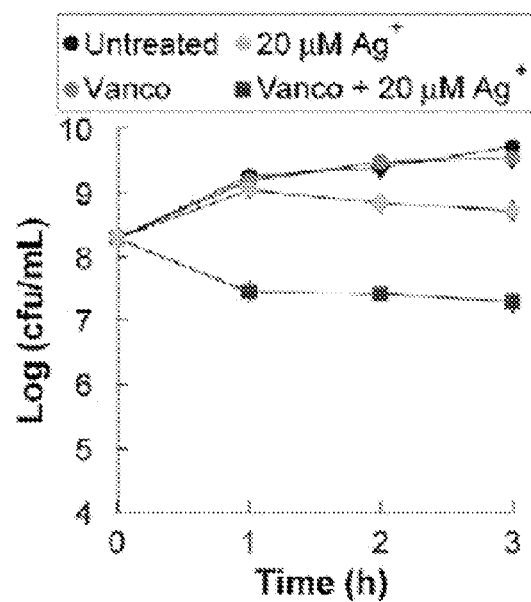
FIG. 8A  FIG. 8B
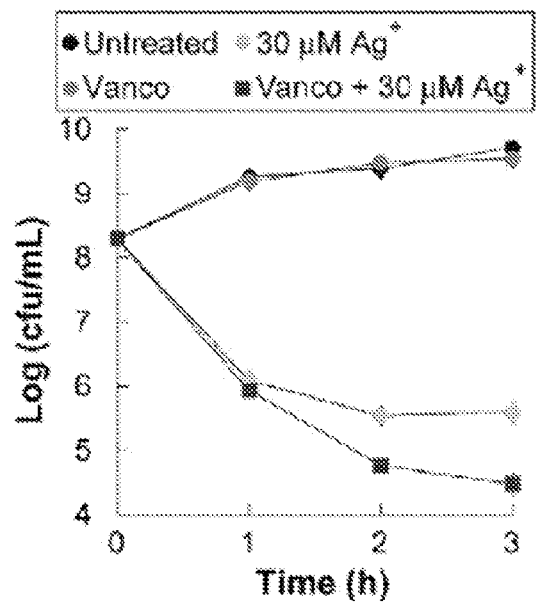
FIG. 8C

METHODS OF TREATING GRAM-NEGATIVE MICROBIAL INFECTIONS

CROSS-REFERENCE TO RELATED APPLICATIONS

This Application is a 35 U.S.C. § 371 National Phase Entry Application of International Application No. PCT/US2012/062138 filed Oct. 26, 2012, which designates the U.S., and which claims the benefit under 35 U.S. § 119(e) of U.S. Provisional Application No. 61/551,649 filed Oct. 26, 2011, the contents of each of which are incorporated herein by reference in their entireties.

GOVERNMENT SUPPORT

This invention was made with Government Support under Contract No. OD003644 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Jul. 28, 2017, is named 701586-071612-US_SL.txt and is 796bytes in size.

TECHNICAL FIELD OF THE DISCLOSURE

The inventions provided herein relates generally to methods and compositions for treating a microbial infection. Specifically, some embodiments relate to methods and compositions for treating a Gram-negative microbial infection.

BACKGROUND

There is a growing need to enhance the current antibacterial arsenal given the rising incidence of antibiotic resistance and the emergence of novel virulent pathogens [1, 2]. This is particularly true for infections caused by Gram-negative bacteria, which are difficult to treat because, unlike Gram-positive bacteria, Gram-negative bacteria possess a protective outer membrane consisting of lipopolysaacharides [11]. This outer membrane protects the Gram-negative bacteria from antibiotics, dyes, and detergents that would normally damage the inner membrane or cell wall (peptidoglycan). The outer membrane provides these bacteria with resistance to lysozyme and penicillin. While alternative antimicrobial agents such as lysozyme with EDTA and the antibiotics, e.g., ampicillin, chloramphenicol, streptomycin, and nalidixic acid, have been developed to combat the protective outer membrane of some pathogenic Gram-negative microbes, the Gram-negative microbes have been evolving and becoming more immune to existing antimicrobial agents such as antibiotics. As there is a declining pipeline of effective antimicrobial agents, it is imperious to develop more effective antimicrobial treatments, for example, to target Gram-negative microbes.

SUMMARY

Embodiments of the inventions are based on our discovery that a sub-inhibitory level of silver is capable of potentiating the activity of an antimicrobial agent in a sub-inhibitory amount to treat microbes, and/or expanding the spectrum of an antimicrobial agent to treat additional microbe groups or species. Although high doses of silver alone have been recognized in the art for its antimicrobial capability [3-10], the inventors have surprisingly discovered that not only can the addition of a sub-inhibitory dose of silver to an antibiotic treatment increase the activity of the antibiotic against the microbes, but that the silver also broadens the spectrum of an antibiotic so that an antibiotic that is indicated for treatment of one microbial strain (e.g., Gram-positive microbes) becomes effective for treating a different microbial strain (e.g., Gram-negative microbes such as *E. Coli*). These can broaden the effectiveness and/or indications of antimicrobial agents (e.g., antibiotics such as Gram-positive specific antibiotics), so that they can now be used against a range of microbes, e.g., Gram-negative microbes that were not previously used for.

Accordingly, in one aspect the invention provides a method for treating a patient having a bacterial infection. The method comprises administering an antibiotic and a silver-containing compound to the patient, where one or both of the antibiotic and silver-containing compound are administered at a dose below which would be effective alone. In accordance with this aspect, the invention further provides compositions comprising antibiotics, such as lipopeptide antibiotics (e.g., daptomycin or derivative thereof) and a silver-containing compound as described herein, wherein one or both are provided at a dose below which would be effective alone.

Accordingly, a second aspect provided herein relates to methods and compositions for treating an individual having a Gram-negative microbial infection. Non-limiting examples of Gram-negative microbes include *E. Coli, Salmonella, Shigella, Pseudomonas, Moraxella, Helicobacter, Stenotrophomonas, Bdellovibrio, Legionella, Acinetobacter, spirochaetes, Neisseria gonorrhoeae, Neisseria meningitides, Hemophilus influenzae, Klebsiella pneumoniae, Proteus mirabilis, Enterobacter, Serratia*, and any combinations thereof.

In such aspect, the method for treating an individual infected with a Gram-negative microbe comprises administering to an individual that has been determined to have a Gram-negative microbial infection an effective amount of a pharmaceutical composition comprising an agent (e.g., antibiotic) that is not effective for treatment of the Gram-negative microbial infection when used alone, and a potentiating amount of a silver-containing compound, thereby treating an individual having a Gram-negative microbial infection.

In some embodiments, the agent (e.g., antibiotic) that is not effective for treatment of the Gram-negative microbial infection when used alone can be an antimicrobial agent (e.g., antibiotic) that does not penetrate through an outer membrane of the Gram-negative microbe. In some embodiments, the agent (e.g., antibiotic) that is not effective for treatment of the Gram-negative microbial infection when used alone can be an agent (e.g., antibiotic) that treats a Gram-positive microbial infection. Exemplary antibiotics that can treat a Gram-positive microbial infection include, but are not limited to, vancomycin, teicoplanin, moenomycin, dicloxacillin, daptomycin, linezolid, oxacillin, nafcillin, or a combination thereof. In some embodiments, the antibiotic is a lipopeptide. In some embodiments, the antibiotic can be a cyclic lipopeptide, such as daptomycin or a similar agent.

In some embodiments, the potentiating amount of the silver-containing compound included in the pharmaceutical composition can be an amount below a threshold level required to effectively treat a Gram-negative microbial infection when used alone. In such embodiments, the potentiating amount of the silver-containing compound is not enough to be toxic by itself to a population of Gram-negative microbes, but is sufficient to expand the spectrum of the antimicrobial agent (e.g., antibiotic) against a different microbe group or species (e.g., use of Gram-positive specific antibiotics for treatment of Gram-negative microbial infection in accordance with some embodiments of the methods described herein). The potentiating amount of the silver-containing compound used in the method described herein can provide or comprise an antimicrobial amount of silver at a concentration of about 0.001 µM to about 100 µM, about 0.01 µM to about 80 µM, about 0.1 µM to about 50 µM, about 1 µM to about 30 µM, about 5 µM to about 25 µM, about 10 µM to about 25 µM, or about 15 µM to about 20 µM.

In some embodiments of any aspects described herein, the silver-containing compound can comprise silver in any form. In some embodiments, the silver-containing compound can comprise elemental silver. In other embodiments, the silver-containing compound can comprise a silver salt or ionic silver. Examples of the silver salt or ionic silver can include, without limitations, silver nitrate, silver acetate, silver benzoate, silver carbonate, silver iodate, silver iodide, silver lactate, silver laurate, silver oxide, silver palmitate, and silver sulfadiazine.

In some embodiments, the Gram-negative microbes can aggregate together and adhere to form a biofilm on a surface. In such embodiments, methods and compositions for treating a Gram-negative microbial biofilm are also provided herein. The method for treating a Gram-negative microbial biofilm comprises administering to a surface that has been determined to be infected with a Gram-negative microbial biofilm an effective amount of an antimicrobial composition comprising an agent that is not effective for treatment of the Gram-negative microbial infection when used alone, and a potentiating amount of a silver-containing compound, thereby treating a Gram-negative microbial biofilm.

The inventors have also discovered that silver can increase membrane permeability of microbes, e.g., Gram-negative microbes, thus enabling delivery of an agent that cannot be delivered otherwise into the microbes. Accordingly, another aspect provided herein relates to methods and compositions for delivering to a Gram-negative microbe an agent that does not normally penetrate across an outer membrane of the Gram-negative microbe when used alone. The method comprises contacting the Gram-negative microbe with an effective amount of a composition comprising the agent and a potentiating amount of a silver-containing compound, wherein the potentiating amount of the silver-containing compound is sufficient to increase membrane permeability of the Gram-negative microbe to the agent, thereby delivering the agent to the Gram-negative microbe.

In some embodiments, the agent can be an antimicrobial agent, e.g., an antibiotic specific for treatment of a Gram-positive microbial infection. Such embodiments can enable the use of Gram-positive specific antimicrobial agents to treat Gram-negative microbial infections.

In other embodiments, the agent can be an optical molecule, e.g., but not limited to, a diagnostic agent such as contrast agent or fluorescent molecules. Such embodiments can allow, for example, a contrast agent, to be delivered into a microbe, e.g., for visualization or diagnostic purposes.

To clarify, the methods described herein are different from those described in U.S. Pat. Nos. 5,374,432 and 6,582,719. For example, while both the '432 and '719 patents describe compositions for topical treatment of a microbial infection comprising silver or a silver salt and an antibiotic indicated to treat the microbial infection, neither the '432 patent nor the '719 patent teaches, suggests nor discusses the use of an antibiotic commonly indicated to treat a specific microbial infection to treat a different microbial infection, when the antibiotic is administered in combination with a silver-containing compound (e.g., a silver salt). Other distinctions will be apparent from the following detailed description of the invention.

BRIEF DESCRIPTION OF THE FIGURES

FIG. 1A shows kill curves for exponentially growing wildtype E. Coli treated with various concentrations of $AgNO_3$. FIG. 1B shows bright field and fluorescence microscopy of HPF-stained untreated E. Coli cells and cells treated with 30 µM silver nitrate ($AgNO_3$) after 1 h. FIG. 1C shows kill curves for exponentially growing wildtype E. Coli treated with 30 µM $AgNO_3$, 150 mM thiourea, or a combination of both, indicating that scavenging OH• within the cell during antibiotic treatment inhibits cell death.

FIG. 2A shows a GFP fluorescence histogram from the Fur reporter strain after 1 h treatment with 15 and 30 µM $AgNO_3$. The inset shows a schematic of the reporter strain which is based on activation of the Fur gene. FIG. 2B shows survival of iron homeostasis gene knockout mutants relative to wildtype when treated with 30 µM $AgNO_3$. FIG. 2C shows a change in fluorescence of the HPF-stained wildtype and ΔiscS strain after 1 h treatment with 30 µM $AgNO_3$. FIG. 2D shows free iron [$Fe^{+2}$] concentration in a cell lysate after 1 h treatment with heat (90° C.) or 30 µM $AgNO_3$. FIG. 2E shows that $Ag^+$ induces activation of soxS, indicating production of ROS. Change in GFP fluorescence from the soxS reporter strain after 1 h of the indicated treatments. Cells were treated with 30 µM $AgNO_3$, 0.5 mM $H_2O_2$, or a combination of both. Values shown are relative to fluorescence at time zero before treatment. The inset shows a schematic of the reporter strain, which is based on activation of the soxS promoter.

FIG. 3A shows survival of electron transport gene knockout mutant relative to wildtype when treated with 30 µM $AgNO_3$. FIG. 3B shows a GFP fluorescence histogram from the soxS reporter, incorporated into a wildtype and ΔcydB strain, after 1 h treatment with 30 µM $AgNO_3$. FIG. 3C shows results of survival assays performed between wild type E. Coli and knockout mutants of cytochrome bd (ΔcydB) and cytochrome bo (ΔcyoA). The ΔcydB mutant shows considerably less sensitivity to silver nitrate than wild type, indicating that cytochrome bd can be a source of superoxide. The ΔcyoA mutant shows greater sensitivity to silver nitrate, indicating that in the absence of cytochrome bo, cells can use cytochrome bd, which is more prone to losing electrons to oxygen. FIG. 3D shows that the indicated TCA cycle gene knockout strains (ΔicdA, ΔsucB, Δmdh, ΔacnB) are less sensitive to $Ag^+$ treatment than wildtype. The bars show percent change in fluorescence for HPF-stained wildtype and TCA cycle mutant strains treated for 1 h with 30 µM AgNO$_3$ relative to the HPF-stained untreated strains. The diamonds represent survival levels relative to wildtype after 3 h of treatment with 30 µM AgNO$_3$. Error bars represent mean±SEM for at least 3 biological replicates. FIG. 3E shows survival of TCA cycle gene knockout mutants relative to wildtype when treated with 30 µM AgNO$_3$.

FIGS. 4A-4F show that Ag$^+$ increases membrane permeability. FIG. 4A shows a set of transmission electron microscopy micrographs showing untreated (left) and 30 µM AgNO$_3$-treated E. coli. The red arrow indicates a cell showing outer membrane separation, which is indicative of membrane stress. The black arrow indicates a cell with significant protein aggregation. FIGS. 4B-4D show that Ag$^+$ induces moderate morphological changes and protein aggregate formation at sublethal concentrations. Transmission electron microscopy micrographs showing: (FIG. 4B) 0 µM; (FIG. 4C) 10 µM; and (FIG. 4D) 20 µM AgNO$_3$-treated E. coli. FIG. 4E shows Propidium Iodide (PI) fluorescence histogram for wildtype E. Coli after 1 h treatment with sublethal Ag$^+$ concentrations (20 µM). FIG. 4F shows bright field and fluorescence microscopy of PI-stained untreated cells and cells treated for 1 h with 30 µM AgNO$_3$.

FIG. 5A shows a schematic of the disulfide bond reporter construct. In the presence of intracellular H$_2$O$_2$, OxyR is activated via the formation of a disulfide bond. The activated OxyR then binds to and activates the dps promoter, which was ligated to GFP, to create a reporter construct that is sensitive to the formation of disulfide bonds. FIG. 5B shows a change in GFP fluorescence from the disulfide bond genetic reporter strain after 1 h of the following treatments: 30 µM AgNO$_3$, 0.5 mM H$_2$O$_2$, and the combination of both. Values shown are relative to fluorescence at time zero before treatment. The inset shows a schematic of the reporter strain, which is based on activation of the dps promoter. FIG. 5C shows that change in fluorescence of PI-stained wildtype and ΔdsbA strains after 1 h of untreated growth, indicating that impairment of disulfide bond formation leads to increased permeability of the cellular outer membrane. FIG. 5D shows survival of disulfide bond formation gene knockout mutants relative to wildtype when treated with 30 µM AgNO$_3$. FIG. 5E shows a change in fluorescence of PI-stained wildtype, ΔdsbA, and ΔsecG strains after 1 h treatment with 30 µM AgNO$_3$. FIG. 5F shows survival of protein secretion and membrane stress gene knockout mutants relative to wildtype when treated with 30 µM AgNO$_3$. Error bars represent mean±SEM for at least 3 biological replicates. FIG. 5G shows an increase in ROS levels of mutant strains leads to cell death. Change in fluorescence of the HPF-stained wildtype, ΔcpxA, ΔcpxR, ΔdsbA and ΔarcA strains after 1 h treatment with 30 µM AgNO$_3$. FIG. 5H shows survival of the ΔarcA strain relative to wildtype when treated with 30 µM AgNO$_3$, indicating that knockout of arcA delays Ag$^+$-induced cell death.

FIGS. 6A-6D show an exemplary multifaceted mechanism of Ag$^+$-induced cell death. Ag$^+$ (represented as yellow diamonds) targets multiple factors which contribute to increases in cell permeability and the overproduction of OH• which lead to cell death. FIG. 6A shows Ag$^+$ disruption of disulfide bonds induces protein misfolding. Translocation of misfolded proteins across the inner membrane leads to increased membrane permeability and envelope stress, which triggers the Cpx regulatory network. FIG. 6B shows that the Cpx system induces changes in key metabolic pathways (ETC and the TCA cycle) through the ArcA system, resulting in superoxide production from cytochrome bd. FIG. 6C shows that the superoxide production induces an intracellular oxidative environment that, in combination with a direct disruptive interaction of Ag$^+$ with Fe—S clusters, causes leakage of Fe$^{+2}$ from internal Fe—S clusters leading to a disruption in iron homeostasis. FIG. 6D shows that the conditions described in FIGS. 6A-6C fuel Fenton chemistry, which produces OH• in excessive amounts leading to cell death.

FIGS. 7A-7E show that Ag$^+$ potentiates bactericidal antibiotics in vitro. FIGS. 7A-7C show that kill curves of wildtype E. Coli after treatment with the following antibiotics: (FIG. 7A) 15 µM AgNO$_3$, 0.25 µg/mL gentamicin, and the combination of both; (FIG. 7B) 15 µM AgNO$_3$, 0.03 µg/mL ofloxacin, and the combination of both; and (FIG. 7C) 15 µM AgNO$_3$, 1 µg/mL ampicillin, and the combination of both, indicating that the addition of sublethal concentrations of Ag$^+$ potentiates bactericidal antibiotics. FIG. 7D shows a log change in cfu/mL, from time zero, of wildtype E. Coli after treatment for 3 h with 15 µM AgNO$_3$, 0.25 µg/mL gentamicin, 0.03 µg/mL ofloxacin, 1 µg/mL ampicillin, and combinations of AgNO$_3$ with the respective antibiotics. FIG. 7E shows changes in HPF fluorescence levels after 1 h of administering the treatments described in FIG. 7D.

FIGS. 8A-8E show that Ag$^+$ potentiates vancomycin antibiotics against E. Coli in vitro. FIGS. 8A-8C show kill curves of wildtype E. Coli after treatment with Ag$^+$, vancomycin and the combination of both, at the following concentrations: (FIG. 8A) 30 µg/mL vancomycin and 15 µM AgNO$_3$; (FIG. 8B) 30 µg/mL vancomycin and 20 µM AgNO$_3$; and (FIG. 8C), 30 µg/mL vancomycin and 30 µM AgNO$_3$, indicating that the addition of Ag$^+$ broadens the spectrum of vancomycin. FIG. 8D shows a log change in cfu/mL, from time zero, of wildtype E. Coli after treatment for 3 h with the indicated concentrations of AgNO$_3$ and 30 µg/mL vancomycin. FIG. 8E shows changes in PI fluorescence levels after 1 h of administering different concentrations of AgNO$_3$.

FIG. 10A show percentage of metabolically active human cell lines (keratinocytes, hepatocytes and neurons) after being treated in vitro with various Ag$^+$ concentrations. FIG. 10B shows survival of mice treated with: no treatment, 70 µM, 120 µM and 240 µM of AgNO$_3$.

DETAILED DESCRIPTION OF THE INVENTION

Figure 1A:
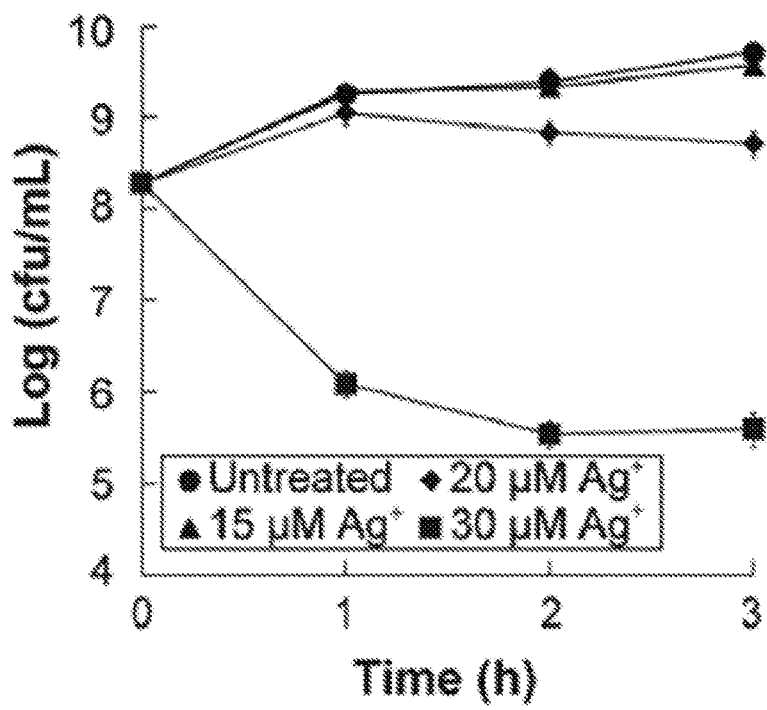
FIGS. 1A-1C show antimicrobial effects of a silver salt on exponentially growing E. Coli.

A declining pipeline of antimicrobial agents (e.g., antibiotics) has made it imperative that there is a strong need to develop more effective antimicrobial treatments. In particular, microbial infections caused by Gram-negative microbes are generally more difficult to treat than those caused by Gram-positive microbes, because the outer membrane possessed by the Gram-negative microbes can protect them from various antimicrobial agents. While silver has been recognized for its antimicrobial effect when a high dose (i.e. a dose toxic to microbes) is used, the bactericidal mode of action of silver remains unclear. In order to develop more effective antimicrobial compositions, the inventors have identified mechanistic effects of silver on Gram-negative bacteria, for example, silver can, at least partly, disrupt multiple bacterial cellular processes and pathways, including disulfide bond formation, central metabolism and/or iron homeostasis. These changes can lead to increases in membrane permeability and the production of reactive oxygen species (ROS). Accordingly, the inventors have discovered that, in one aspect, a low dose (e.g., a sub-inhibitory dose) of silver to induce oxidative stress can potentiate the efficacy of antimicrobial agents that utilize ROS as part of their microbicidal mechanism. In another aspect, the inventors have discovered that a low dose (e.g., a sub-inhibitory dose) of silver to increase membrane permeability of microbes can sensitize Gram-negative microbes to Gram-positive specific antimicrobial agents such as Gram-positive specific antibiotics, e.g., vancomycin, thus expanding the antimicrobial spectrum of Gram-positive specific antimicrobial agents to treat Gram-negative microbes. Further, the use of silver, whether at sub-lethal doses or higher, can increase the therapeutic window for antimicrobial agents that might otherwise have adverse effects to a patient, or for antimicrobial agents for which a target pathogen exhibits mild resistance.

Accordingly, in one aspect the invention provides a method for treating a patient having a bacterial infection. The method comprises administering an antibiotic and a silver-containing compound to the patient, where one or both of the antibiotic and silver-containing compound are administered at a dose below which would be effective alone. The antibiotic, embodiments of which are described herein, may be administered (e.g., co-formulated with) the silver-containing compound. For example, the antibiotic and silver-containing compound can be co-formulated for topical or intravenous administration, or other appropriate route. In other embodiments, the antibiotic and silver-containing compound are administered separately, by the same or different route. In some embodiments, aspects of the invention are applicable to antimicrobial agents not known to penetrate the outer membrane of gram-negative bacteria, and such agents include, but are not limited to, lipopeptides and cyclic lipopeptides, such as daptomycin for example. In other embodiments, aspects of the invention are applicable to antimicrobial agents with a narrow therapeutic window due to toxic effects on the host. In such embodiments, the MIC of the anti-microbial agent is lowered by providing an amount of silver sufficient to induce production of endogenous ROS in the target microbe.

In accordance with the inventions, one aspect provided herein relates to methods for treating an individual having a specific microbial infection (e.g., a Gram-negative or Gram-positive microbial infection) comprising administering to an individual that has been determined to have a specific microbial infection (e.g., a Gram-negative or Gram-positive microbial infection) an effective amount of a pharmaceutical composition comprising an agent (e.g., an antibiotic) that is not effective for treatment of the specific microbial infection (e.g., a Gram-negative or Gram-positive microbial infection) when used alone, and a potentiating amount of a silver-containing compound, wherein the potentiating amount of the silver-containing compound is sufficient to expand the spectrum of the agent (e.g., the antibiotic), but not enough to be toxic by itself to a population of the microbes.

In some embodiments, the method is directed to treating an individual having a Gram-negative microbial infection comprising administering to an individual that has been determined to have a Gram-negative microbial infection an effective amount of a pharmaceutical composition comprising an agent (e.g., an antibiotic) that is not effective for treatment of the Gram-negative microbial infection when used alone, and a potentiating amount of a silver-containing compound, wherein the potentiating amount of the silver-containing compound is sufficient to expand the spectrum of the agent (e.g., the antibiotic), but not enough to be toxic by itself to a population of the microbes. In alternative embodiments, the method can be used to treat an individual having a Gram-positive microbial infection comprising administering to an individual that has been determined to have a Gram-positive microbial infection an effective amount of a pharmaceutical composition comprising an agent (e.g., an antibiotic) that is not effective for treatment of the Gram-positive microbial infection when used alone, and a potentiating amount of a silver-containing compound, wherein the potentiating amount of the silver-containing compound is sufficient to expand the spectrum of the agent (e.g., the antibiotic), but not enough to be toxic by itself to a population of the microbes.

A microbial infection can be present anywhere and exist as single cells, in colonies, or in a film. In some embodiments, microbes can aggregate together and adhere on a surface to form a biofilm, which is generally more resistant to microbes present in single cells. In such embodiments, methods for treating a surface having a microbial biofilm (e.g., a Gram-negative microbial biofilm) are also provided herein. Such method comprises administering to a surface that has been determined to have a microbial biofilm (e.g., a Gram-negative microbial biofilm) an effective amount of a composition comprising an agent that is not effective for treatment of the microbial biofilm (e.g., a Gram-negative microbial biofilm) when used alone, and a potentiating amount of a silver-containing compound, wherein the potentiating amount of the silver-containing compound is sufficient to expand the spectrum of the agent, but not enough to be effective by itself to treat the biofilm.

In accordance with some aspects of the invention, a silver-containing compound can increase membrane permeability of a microbe. Thus, another aspect provided herein include methods for delivering to a microbe (e.g., a Gram-negative microbe) an agent that does not penetrate across an outer membrane of the Gram-negative microbe when used alone, the methods comprising contacting the microbe (e.g., a Gram-negative microbe) with an effective amount of a composition comprising the agent and a potentiating amount of a silver-containing compound, wherein the potentiating amount of the silver-containing compound is sufficient to increase membrane permeability of the microbe (e.g., the Gram-negative microbe) to the agent, thereby delivering the agent to the Gram-negative microbe.

As used herein, the term "effective amount" is generally meant an amount of an agent or a composition described herein effective to achieve an indicated effect, e.g., reducing the growth and/or number of the viable target microbes such as pathogenic bacteria, or reducing at least one symptom of a microbial or bacterial infection. In some embodiments, the composition comprising an antimicrobial agent as described herein and a silver containing compound is effective to substantially reduce or inhibit the growth and/or the number of viable target microbes, such as pathogenic bacteria. In various embodiments, the composition is effective to eliminate a bacterial infection or a detectable presence of a pathogen or target microbe. In some embodiments, the effective amount of the composition comprises an antimicrobial agent and a silver-containing compound, where one or both is present in an amount below a minimum amount required to treat a microbial infection if used individually.

In some embodiments, the effective amount is an amount of a composition comprising an agent as described herein and a silver-containing compound, effective to substantially increase the amount of the agent to be delivered into a microbe (e.g., a Gram-negative microbe), as compared to in the absence of the silver-containing compound. In some embodiments, the agent can be an optical molecule as described herein, enabling the optical molecule to be delivered into the microbe, e.g., to facilitate visualization and/or imaging of the microbe, e.g., for diagnosis purpose. In some embodiments, the agent can be an antimicrobial agent (e.g., an antimicrobial agent that cannot effectively enter or remain into the microbe in the absence of the silver-containing compound), e.g., for antimicrobial effect.

The terms "treatment" and "treating" as used herein, with respect to treatment of a disease (e.g., a microbial infection), means preventing the progression of the disease, or altering the course of the disorder (for example, but are not limited to, slowing the progression of the disorder), or reversing a symptom of the disorder or reducing one or more symptoms and/or one or more biochemical markers in a subject, preventing one or more symptoms from worsening or progressing, promoting recovery or improving prognosis. For example, in the case of treating a microbial infection, e.g., a Gram-negative microbial infection, therapeutic treatment refers to a reduction or elimination of the microbes after administration of the composition described herein. In another embodiment, the therapeutic treatment refers to alleviation of at least one symptom associated with a microbial infection, e.g., a Gram-negative infection. Measurable lessening includes any statistically significant decline in a measurable marker or symptom, such as measuring the number of white blood cells and/or levels of complements in a blood sample, and/or assessing the redness and/or swelling in an infected area after treatment. Other symptoms can include malaise, fever, and pain associated with a microbial infection. In various emodiments, the method results in the elmination of a bacterial infection in a patient.

In some embodiments, the efficacy of treatment can be measured as an improvement in morbidity or mortality (e.g., lengthening of survival curve for a selected population). Prophylactic methods (e.g., preventing or reducing the incidence of relapse) are also considered treatment.

In some embodiments, a silver-containing compound and an agent (e.g., an antibiotic) can be concurrently administered to an individual. In some embodiments, a silver-containing compound and an agent can each be individually administered to an individual, e.g., the silver-containing compound can be administered prior to or after administration of the agent.

Agents used in the methods described herein (e.g., antibiotics)

As used herein, the term "agent" generally means any entity or compound that is administered to an individual, applied to a surface, or delivered into a microbe, in combination with a silver-containing compound, for the purposes of the methods described herein, including, but are not limited to, for treatment of a microbial infection or a microbial biofilm, for visualization and/or imaging purposes, and/or for diagnostic purposes. Agents can be generally chemicals (e.g., synthetic or naturally-occurring), antimicrobial agents (e.g., antibiotics), optical molecules (e.g., fluorescent molecules or dyes), contrast agents, therapeutic agents, small molecules, nucleic acid, proteins, peptides, aptamers, antibodies or fragments thereof, vaccines, or any combinations thereof. Agents can be known to have a desired activity and/or property, or can be selected from a library of diverse compounds.

In some embodiments, the agent used in the methods for treatment of a microbial infection or a microbial biofilm described herein can be an antimicrobial agent. The term "antimicrobial agent" as used herein refers to any entity with antimicrobial activity, i.e. the ability to inhibit or reduce the growth and/or kill a microbe, for example, Gram positive- or Gram negative bacteria. In various embodiments, the antimicroial agent is a compound indicated for treatment of a bacterial infection in a human or veterinary patient.

In one embodiment, an antimicrobial agent is an agent that specifically targets one microbe group classified by a Gram stain test, e.g., Gram-positive vs. Gram-negative microbes. In some embodiments, an antimicrobial agent is an agent that specifically target one microbe genus (e.g., without limitations, *Staphylococcus* spp., or *Escherichia* spp.). In some embodiments, an antimicrobial agent is an agent that specifically target one microbe species (e.g., without limitations, *S. aureus* or *E. Coli*). In another embodiment, an antimicrobial agent can modify (i.e. inhibit or activate or increase) a pathway which is specifically expressed in microbes.

In some embodiments where the method is directed to treatment of a Gram-negative microbial infection or a Gram-negative microbial biofilm, an antimicrobial agent can exclude any agent that is generally used for treatment of the microbial infection or microbial biofilm associated with or caused by the Gram-negative microbes (e.g., Gram-negative bacteria). In some embodiments, the antimicrobial agent used in the methods described herein for treatment of a Gram-negative microbial infection or a Gram-negative microbial biofilm can be commonly indicated to treat other microbial infections other than the Gram-negative microbial infection (e.g., Gram-positive microbial infections).

An antimicrobial agent can be, for example, but not limited to, a small molecule, a peptide, a peptidomimetics, an antibody or a fragment thereof, a nucleic acid, an aptamer, a drug, a chemical or any entity that can inhibit the growth and/or kill a microbe.

In some embodiments, an antimicrobial agent or an agent can be an antimicrobial peptide, for example but not limited to, mefloquine, venturicidin A, antimycin, myxothiazol, stigmatellin, diuron, iodoacetamide, potassium tellurite hydrate, aDL-vinylglycine, N-ethylmaleimide, L-allyglycine, diaryquinoline, betaine aldehyde chloride, acivcin, psicofuraine, buthionine sulfoximine, diaminopemelic acid, 4-phospho-D-erythronhydroxamic acid, motexafin gadolinium and/or xycitrin or modified versions or analogues thereof.

Antibiotics: In some embodiments, an agent or an antimicrobial agent can be an antibiotic. As used herein, the term "antibiotic" is art recognized and includes antimicrobial agents naturally produced by microorganisms such as bacteria (including *Bacillus* species), actinomycetes (including *Streptomyces*) or fungi that inhibit growth of or destroy other microbes, or genetically-engineered thereof and isolated from such natural source. Substances of similar structure and mode of action can be synthesized chemically, or natural compounds can be modified to produce semi-synthetic antibiotics.

The antibiotic in various embodiments can be a bactericidal antibiotic or a bacteriostatic antibiotic. Bactericidals can kill bacteria directly where bacteriostatics can prevent them from dividing. Antibiotics can accomplish their antibacterial effect through several mechanisms of action which can be generally grouped as follows: (1) agents acting on the bacterial cell wall such as bacitracin, cephalosporins, cycloserine, fosfomycin, penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fucidin, lincomycin, puromycin, rifampicin, other streptomycins, and macrolide antibiotics such as erythromycin and oleandomycin; (4) agents affecting nucleic acid metabolism, e.g., the fluoroquinolones, actinomycin, ethambutol, fluorocytosine, griseofulvin, rifamycins; and (5) drugs affecting intermediary metabolism, such as the sulfonamides, trimethoprim, and the tuberculostatic agents isoniazid and paraaminosalicylic acid. Some agents can have more than one primary mechanism of action at higher concentrations. In addition, secondary changes in the structure or metabolism of the bacterial cell can often occur after the primary effect of the antibiotics.

Exemplary classes of antibiotics include, but are not limited to, (1) β-lactams, including the penicillins, cephalosporins monobactams, and carbapenems; (2) aminoglycosides, e.g., gentamicin, kanamycin, neomycin, tobramycin, netilmycin, paromomycin, and amikacin; (3) tetracyclines, e.g., doxycycline, minocycline, oxytetracycline, tetracycline, and demeclocycline; (4) sulfonamides (e.g., mafenide, sulfacetamide, sulfadiazine and sulfasalazine) and trimethoprim; (5) quinolones, e.g., ciprofloxacin, norfloxacin, and ofloxacin; (6) glycopeptides (e.g., vancomycin, telavancin, teicoplanin) and lipopeptides (e.g., daptomycin); (7) macrolides, which include for example, erythromycin, azithromycin, and clarithromycin; (8) carbapenems (e.g., ertapenem, doripenem, meropenem, and imipenem); (9) cephalosporins (e.g., cefadroxil, cefepime, and ceftobiprole); (10) lincosamides (e.g., clindamycin, and lincomycin); (11) monobactams (e.g., aztreonam); (12) nitrofurans (e.g., furazolidone, and nitrofurantoin); (13) Penicillins (e.g., amoxicillin, and Penicillin G); (14) polypeptides (e.g., bacitracin, colistin, and polymyxin B); and (15) other antibiotics, e.g., the polymycins, chloramphenicol, and drugs against mycobacteria (e.g., the ones causing diseases in mammals, including tuberculosis (*Mycobacterium tuberculosis*) and leprosy (*Mycobacterium leprae*).

In some embodiments of the methods described herein for treatment of a microbial infection or a microbial film, the antimicrobial agent (e.g., antibiotics) used in those methods can exclude an antimicrobial agent (e.g., antibiotics) that is commonly used to treat that specific microbial infection or microbial biofilm. Stated another way, in some embodiments of the methods described herein for treatment of an infection or a biofilm associated with or caused by one microbe group or species, the antimicrobial agent (e.g., antibiotics) used in those methods can be an antimicrobial agent (e.g., antibiotics) that is commonly used to treat an infection or a biofilm associated with or caused by another microbe group or species, rather than the microbe group or species that is causing the infection or biofilm.

For example, in some embodiments where the methods described herein are used for treatment of a Gram-negative infection or biofilm, the antibiotic used in those methods can exclude an antibiotic that is commonly used to treat a Gram-negative microbial infection or Gram-negative microbial biofilm, e.g., but not limited to, aminoglycosides (e.g., gentamicin, neomycin, and kanamycin). In some embodiments, the antibiotic used for those methods described herein can exclude broad-spectrum antibiotics (i.e., antibiotics that can treat more than one microbe group, such as both Gram-positive and Gram-negative bacteria), for example, but not limited to, carbapenems and cephalosporins.

In some embodiments, the antibiotic that can be used for the methods described herein for treatment of a Gram-negative microbial infection can be the ones that are not effective for treatment of a Gram-negative microbial infection by itself.

In some embodiments, the antibiotic used in the methods described herein for treatment of a Gram-negative microbial infection can be an antibiotic, of which a bacteriostatic or bacteriocidal amount of the antibiotic does not penetrate the outer membrane of the bacteria when the antibiotic is present at nanomolar or micromolar concentrations (or less).

In some embodiments, the antibiotic used in the methods described herein for treatment of a Gram-negative microbial infection can include the antibiotic that is commonly indicated to treat a Gram-positive microbial infection. In such embodiments, the antibiotic that is commonly indicated to treat a Gram-positive microbial infection can specifically inhibit or reduce the growth of Gram-positive microbes, and have little or no bactericidal or bacteriostatic effect on Gram-negative microbes when present at a nanomolar or micromolar concentration (or less), or when present at a level that is not substantially toxic to the host. Such exemplary antibiotics include, but are not limited to, glycopeptide antibiotics, lipopeptide antibiotics and oxazolidinones (e.g., linezolid). In some embodiments, antibiotics that are indicated to specifically treat a Gram-positive microbial infection can include vancomycin, teicoplanin, moenomycin, dicloxacillin, daptomycin, linezolid, oxacillin, nafcillin, rafampicin, telavancin, and any combinations thereof. Additional antibiotics specific for treatment of a Gram-positive microbial infection can include the ones describes in U.S. Pat. No. 5,516,905, and U.S. Pat. App. Nos.: US 2010/0285140 and US 2010/0247546. In some embodiments, antibiotics that are indicated to specifically treat a Gram-positive microbial infection include vancomycin, teicoplanin and moenomycin.

Methods for treatment of a Gram-positive microbial infection or a Gram-positive microbial microfilm involving the use of an antimicrobial agent specific for Gram-negative microbes in the presence of a silver-containing compound are also within the scope of the invention.

Without wishing to be bound by theory, the inventors have demonstrated that silver can increase membrane permeability of a microbe (e.g., a Gram-negative microbe such as *E. Coli*), thus enabling the delivery of, for example, Gram-positive specific antibiotics, into Gram-negative microbes (e.g., bacteria such as *E. Coli.*). Accordingly, some aspects described herein provided methods for delivery to a Gram-negative microbe an agent that does not generally penetrate across an outer membrane of the Gram-negative microbe by itself. Other than antimicrobial agents described herein, in some embodiments, the agent can be an optical molecule. As used herein, the term "optical molecule" refers to a molecule that produces a signal that can be optically detected by an optical instrument (e.g., microscopes, or medical imaging cameras) or by bare eyes. Exemplary optical molecules include, but are not limited to, fluorescent reporters and chemiluminescent groups. A wide variety of fluorescent reporter dyes are known in the art. Typically, the fluorophore is an aromatic or heteroaromatic compound and can be a pyrene, anthracene, naphthalene, acridine, stilbene, indole, benzindole, oxazole, thiazole, benzothiazole, cyanine, carbocyanine, salicylate, anthranilate, coumarin, fluorescein, rhodamine or other like compound. Suitable fluorescent reporters include xanthene dyes, such as fluorescein or rhodamine dyes, including, but not limited to, Alexa Fluor® dyes (InvitrogenCorp.; Carlsbad, Calif.), fluorescein, fluorescein isothiocyanate (FITC), Oregon Green™, rhodamine, Texas red, tetrarhodamine isothiocynate (TRITC), 5-carboxyfluorescein (FAM), 2'7'-dimethoxy-4'5'-dichloro-6-carboxyfluorescein (JOE), tetrachlorofluorescein (TET), 6-carboxyrhodamine (R6G), N,N,N,N'-tetramefhyl-6-carboxyrhodamine (TAMRA), 6-carboxy-X-rhodamine (ROX). Suitable fluorescent reporters also include the naphthylamine dyes that have an amino group in the alpha or beta position. For example, naphthylamino compounds include 1-dimethylamino-naphthyl-5-sulfonate, 1-anilino-8-naphthalene sulfonate, 2-p-toluidinyl-6-naphthalene sulfonate, and 5-(2'-aminoethyl)aminonaphthalene-1-sulfonic acid (EDANS). Other fluorescent reporter dyes include coumarins, such as 3-phenyl-7-isocyanatocoumarin; acridines, such as 9-isothiocyanatoacridine and acridine orange; N-(p (2-benzoxazolyl)phenyl)maleimide; cyanines, such as Cy2, indodicarbocyanine 3 (Cy3), indodicarbocyanine 5 (Cy5), indodicarbocyanine 5.5 (Cy5.5), 3-(-carboxy-pentyl)-3'ethyl-5,5'-dimethyloxacarbocyanine (CyA); 1H,5H,11H, 15H-Xantheno[2,3,4-ij:5,6,7-i'j']diquinolizin-18-ium, 9-[2 (or 4)-[[[6-[2,5-dioxo-1-pyrrolidinyl)oxy]-6-oxohexyl] amino]sulfonyl]-4(or 2)-sulfophenyl]-2,3,6,7,12,13,16, 17octahydro-inner salt (TR or Texas Red); BODIPY™ dyes; benzoxadiazoles; stilbenes; pyrenes; and the like. Many suitable forms of these fluorescent compounds are available and can be used.

Examples of fluorescent proteins suitable for use as imaging agents include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al, Mol. Microbiol, 55:1767-1781 (2005), the GFP variant described in Crameri et al, Nat. Biotechnol., 14:315319 (1996), the cerulean fluorescent proteins described in Rizzo et al, Nat. Biotechnol, 22:445 (2004) and Tsien, Annu. Rev. Biochem., 67:509 (1998), and the yellow fluorescent protein described in Nagal et al, Nat. Biotechnol., 20:87-90 (2002). DsRed variants are described in, e.g., Shaner et al, Nat. Biotechnol., 22:1567-1572 (2004), and include mStrawberry, mCherry, morange, mBanana, mHoneydew, and mTangerine. Additional DsRed variants are described in, e.g., Wang et al, Proc. Natl. Acad. Sci. U.S.A., 101:16745-16749 (2004) and include mRaspberry and mPlum. Further examples of DsRed variants include mRFPmars described in Fischer et al, FEBS Lett., 577:227-232 (2004) and mRFPruby described in Fischer et al, FEBS Lett, 580:2495-2502 (2006).

Very small particles, termed nanoparticles, also can be used as optical molecules to be delivered into a microbe (e.g., a Gram-negative microbe). These particles can range from 1-1000 nm in size and include diverse chemical structures such as gold and silver particles and quantum dots.

In some embodiments, the agent can be a diagnostic agent (e.g., a contrast agent), for example, to facilitate visualization of a microbe (e.g., a Gram-negative microbe).

In some embodiments, the antimicrobial agent can be administered at lower levels, when administered with a potentiating amount of a silver-containing compound, either for treatment of gram-negative or gram-positive microorganisms. For example, in some embodiments the antimicrobial agent is daptomycin, and the daptomycin is co-formulated with a silver-containing compound such as a silver salt or ionic silver (e.g., silver nitrate), which is present at less than 100 µM, less than 50 µM, less than 30 µM, or less than 20 µM or as described below. In such embodiments, the daptomycin is administered at less than about 4 mg/kg for intravenous administration, such as less than about 3.5 mg/kg, less than about 3.0 mg/kg, less than about 2.5 mg/kg, less than about 2.0 mg/kg, or about 1.0 mg/kg or less. In such embodiments, the daptomycin exhibits a reduced incidence of adverse side effects to the patient, in addition to rendering the combination broad spectrum.

In accordance with embodiments provided herein, a silver-containing compound is used in conjunction with (i.e., in combination with) at least one antimicrobial agent (e.g., at least 1, at least 2, at least 3, at least 4, at least 5 or more antimicrobial agents), and the silver-containing compound serves as an adjuvant to such antimicrobial agent. As used herein, the term "adjuvant" refers to an agent which significantly enhances the antimicrobial effect of another agent. In some embodiments, the silver-containing compounds can function as adjuvants to antimicrobial agents, such as, but not limited to antibiotics, by enhancing the effect of the antimicrobial agents.

As used herein, the phrases "enhances the antimicrobial effect of another agent" and "enhancing the effect of the antimicrobial agents" can include increasing the antimicrobial activity of an antimicrobial agent against a microbe, and/or increasing the antimicrobial activity of an antimicrobial agent that is indicated for treatment of a microbe type or species to become effective for treating a different microbe type or species. In some embodiments, the silver-containing compound can increase the antimicrobial activity of an antimicrobial agent that is indicated for treatment of a microbe type or species to become effective for treating a different microbe type. In some embodiments, the silver-containing compound can increase the activity of an antimicrobial agent (e.g., an antibiotic) that is indicated for treatment of a Gram-positive microbe to become effective for treating a Gram-negative microbe. In some embodiments, the silver-containing compound can increase the activity of an antimicrobial agent (e.g., an antibiotic) that is indicated for treatment of a Gram-negative microbe to become effective for treating a Gram-positive microbe.

As used herein, the phrase "activity of an antimicrobial agent" refers to microbicidal and/or microbiostatic effect of an antimicrobial agent against a microbe in the methods described herein when present at nanomolar or micromolar concentrations. The microbicidal effect can be instantaneous after administration of an antimicrobial agent or the maximum microbicidal effect can develop over a period of time (e.g., about 1 hr, about 2 hour, about 3 hours, about 6 hours, about 12 hours, about 1 day, about 2 days, about 3 days, about 1 week, about 2 weeks, about 3 weeks, about 1 month, about 2 months, about 3 months or longer, or after completion of a treatment regimen of any length recommended by a practitioner). The term "microbiostatic effect" as used herein is used in reference to the efficacy of an antimicrobial agent to reduce or inhibit the growth or proliferation of a microbe or a population of microbes.

In some embodiments, the potentiating amount of the silver-containing compound is an amount below a threshold amount of the silver-containing compound required to effectively treat a microbe when used alone. For example, silver alone has been known to have an antimicrobial effect when used in a dose high enough to be toxic to a population of the microbes. Such threshold amount of the silver-containing compound can be determined by measuring the minimum concentration of the silver-containing compound required to exert a toxic effect on a population of the microbes (e.g., reduce or inhibit the growth of a microbe by at least about 30% or higher, or to kill at least about 30% of the microbes, as compared to in the absence of a silver-containing compound) when used alone. One of ordinary skill in the art can readily perform an in vitro experiment to determine such threshold amount, for example, using the colony-forming unit measure as described in the Examples. For example, as shown in FIG. 1A, a silver-containing compound (e.g., a silver salt such as silver nitrate) comprising silver ions at a concentration of about 30 μM reduces or inhibits the growth of a microbe (e.g., *E. Coli*) by at least about 30% or higher, as compared to untreated microbes. Accordingly, in some embodiments, the potentiating amount of the silver-containing compound can be less than 30 μM or less than 25 μM.

Figure 8D:
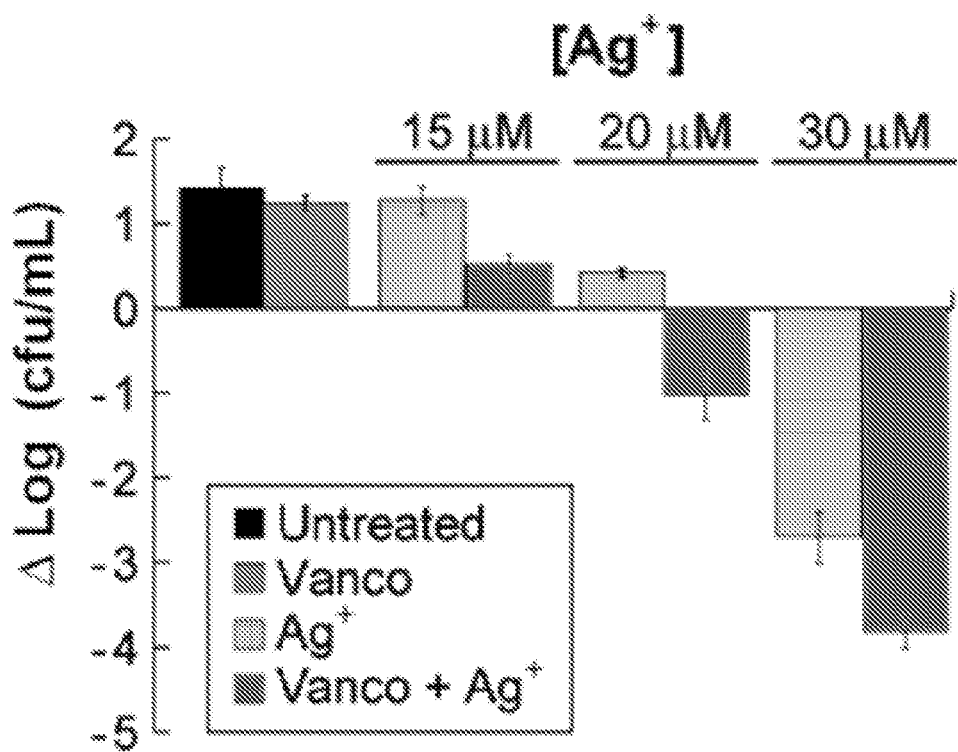

In some embodiments, the potentiating amount of the silver-containing compound is an amount sufficient to expand the spectrum of an antimicrobial agent (e.g., an antibiotic). As used herein, the term "spectrum" can refer to the activity of an antimicrobial agent against a population of the microbes or a microbial infection, and/or the number of microbe groups or species that the antimicrobial agent are indicated to treat. In other embodiments, the potentiating amount of the silver-containing compound can be an amount sufficient to confer an antimicrobial agent a new indication, for example, providing bacteriostatic or bacteriocidal effects for the antimicrobial agent at therapeutic concentrations against a microbe group or species that is otherwise not substantially effected by the antimicrobial agent alone. By way of example only, the potentiating amount of the silver-containing compound can be an amount sufficient to enable the use of an antimicrobial agent specifically indicated for treating a Gram-positive microbial infection to effectively treat a Gram-negative microbial infection. For example, as shown in FIG. 8D, an antibiotic specifically indicated for treatment of a Gram-positive microbial infection (e.g., vancomycin), in combination with a silver-containing compound (e.g., a silver salt such as silver nitrate) comprising silver ions at a concentration of about 15 μM, reduces the growth of Gram-negative microbes (e.g., *E. Coli*). Increasing the silver ion concentration can further increase the efficacy of the Gram-positive specific antimicrobial agent for treatment of a Gram-negative microbial infection.

Without wishing to be bound by theory, the potentiating effect of a silver-containing compound on an antimicrobial agent, is partly mediated through, an significant increase of membrane permeability of microbes (e.g., Gram-negative microbes) in the presence of the silver-containing compound. In some embodiments, the potentiating amount of a silver-containing compound can be an amount sufficient to increase membrane permeability of a microbe (e.g., a Gram-negative microbe) to an agent described herein (e.g., but not limited to, an antimicrobial agent and an optical molecule), for example, an increase in membrane permeability of a microbe to an agent by at least about 2-fold, at least about 3-fold, at least about 4-fold, at least about 5-fold, or higher, as compared to the membrane permeability of the microbes in the absence of the silver-containing compound. An ordinary skill in the art can adjust the potentiating amount of the silver-containing compound so that the membrane permeability of a microbe to an agent can be optimized. Such adjustment or optimization can be based on various factors such as the microbe type or species, the size of an agent to be delivered, the concentrations of a silver-containing compound and/or an agent to be delivered. Methods for measuring membrane permeability of a microbe are well known in the art, e.g., by measuring membrane potential, assessing diffusion of different-sized molecules across the membrane of a microbe, and/or using a HPLC-based method described in Bellido et al (1991) Antimicrobial Agents and Chemotherapy 35 (1): 68-72.

In some embodiments of any aspects described herein, the amount of the silver-containing compound present or provided for potentiation of the antimicrobial agent is present at a concentration of about 0.001 μM to about 100 μM, about 0.01 μM to about 80 μM, about 0.1 μM to about 50 μM, about 1 μM to about 30 μM, about 5 μM to about 25 μM, about 10 μM to about 25 μM, or about 15 μM to about 20 μM. In some embodiments, the potentiating amount of the silver-containing compound is present at a concentration of about 1 μM to about 30 μM, about 5 μM to about 25 μM, about 5 μM to about 20 μM, about 10 μM to about 20 μM, or about 15 μM to about 20 μM. In some embodiments, the silver-containing compound is present at less than 25 μM, or less than 20 μM, or less than 10 μM.

To achieve the potentiating concentration for in vivo administration, in some embodiments, the potentiating amount of the silver-containing compound is administered to an individual in the range of about 0.01 mg/kg to about 100 mg/kg, about 0.05 mg/kg to about 50 mg/kg, about 0.1 mg/kg to about 40 mg/kg, about 0.5 mg/kg to about 25 mg/kg, or about 1 mg/kg to about 15 mg/kg. In some embodiments, the potentiating amount of the silver-containing compound can be about 0.5 mg/kg to about 4 mg/kg. In some embodiments, the potentiating amount of the silver-containing compound can be about 6 mg/kg or lower. Such amounts can be delivered by any appropriate route described herein, including intravenous, topical, or oral, and can be co-formulated with the antimicrobial agent or antibiotic in some embodiments.

Silver can exist in any form within the silver-containing compound. In some embodiments, the silver-containing compound can comprise elemental silver. In some embodiments, the elemental silver can be prepared in the form of colloidal silver. The term "colloidal silver" as used herein relates to any preparation of elemental silver that is sufficiently finely dispersed to form a colloid solution when dispersed in water. The average silver particle size is generally in the range from 1 to 100 nanometers, typically 1 to 10 nanometers, corresponding to generally less than $10^9$ silver atoms per particle. Several different methods for the preparation of silver colloids are known in the art, including, but not limited to, mechanical milling, electrolytic processes, and chemical reduction of silver salts in solution, and any art-recognized method. The colloid can be provided in the form of a powder or of an aqueous dispersion ("colloid solution"). In some embodiments, colloidal silver can also contain a certain proportion of ionic silver in addition to elemental silver due to redox reactions on the surface of the silver particles. In other embodiments, the elemental silver can be prepared in the form of silver nanoparticles. As used herein, the term "silver nanoparticle" can include nanoparticles of silver metal, a silver metal alloy, oxidized silver or silver alloy or silver oxide. The term "silver metal" or "silver alloy" refers to those which have not yet been oxidized. In some embodiments, the "silver nanoparticles" can contain at least some silver oxide and are referred to herein as "silver oxide nanoparticles". In such embodiments, the silver oxide nanoparticles can comprise a core of silver or silver alloy surrounded by a layer of the oxide. Alternatively, the silver oxide nanoparticles can consist entirely of silver oxide.

In some embodiments, the silver-containing compound can comprise a silver salt or ionic silver. The term "ionic silver" as used herein, can encompass both the cationic form of silver, $Ag^+$, and the anionic silver thiosulfate complex, and other silver metal complexes. In particular embodiments, ionic silver is in the cationic form of silver, i.e., $Ag^+$. The cationic form silver can be present in various silver salts. Examples of silver salts include, but are not limited to, silver nitrate, silver benzoate, silver carbonate, silver iodate, silver iodide, silver lactate, silver laurate, silver palmitate, silver oxide, silver bromide, silver fluoride, silver chloride, silver sulfate, silver dihydrogen citrate, silver alkylcarboxylate, silver sulphadiazine or silver arylsulfonate. Silver alkyl carboxylates are the silver salts of alkylcarboxylic acids preferably having from 1-12 aliphatic carbon atoms, or from 1-4 aliphatic carbon atoms, e.g. silver acetate. The aryl group of the arylsulfonate salts is an aromatic radical, e.g., optionally substituted phenyl or naphthyl, preferably alkaryl having 1 to 12 aliphatic carbon atoms, or alkylphenyl having from 1 to 4 aliphatic carbon atoms, e.g., p-toluenesulfonate. In some embodiments, a silver salt can be silver sulfadiazine. In some embodiments, a silver salt used in the method described herein is silver nitrate.

Compositions used in the methods described herein, and administration thereof

Pharmaceutical compositions: For administration to an individual or a subject, the compositions comprising an agent (e.g., an antimicrobial agent such as an antibiotic or an optical molecule) and a silver-containing compound described herein can be provided in pharmaceutically acceptable compositions. These pharmaceutically acceptable compositions comprise an agent (e.g., antimicrobial agent such as an antibiotic) and a silver-containing compound formulated together with one or more pharmaceutically acceptable carriers (additives) and/or diluents. In some embodiments, an agent and a silver-containing compound within the pharmaceutical composition can be each formulated in different or the same pharmaceutically-acceptable carriers (additives) and/or diluents. In some embodiments, an agent and a silver-containing compound that are each individually formulated can be prepared in separate packagings. In some embodiments, an agent and a silver-containing compound within a pharmaceutical composition can be formulated together as a whole in the same pharmaceutically acceptable carriers (additives) and/or diluents.

As described in detail below, the pharmaceutical compositions of the present invention can be specially formulated for administration in solid or liquid form, including those adapted for the following: (1) oral administration, for example, drenches (aqueous or non-aqueous solutions or suspensions), gavages, lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960, content of all of which is herein incorporated by reference.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Pharmaceutical compositions can be administered to a subject by any known route. By way of example, the composition can be administered by a mucosal, pulmonary, topical, or other localized or systemic route (e.g., enteral and parenteral). The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection, infusion and other injection or infusion techniques, without limitation. The phrases "systemic administration," "administered systemically", "peripheral administration" and "administered peripherally" as used herein mean the administration of the composition as disclosed herein such that it enters the animal's system and, thus, is subject to metabolism and other like processes, for example, subcutaneous administration.

In some embodiments, the pharmaceutical composition described can be administered via a systemic route to a subject. In some embodiments, the pharmaceutical composition described herein can be applied topically to a target area of a subject, e.g., a burn wound.

Suitable choices in amounts and timing of doses, formulation, and routes of administration can be made with the goals of achieving a favorable response in the subject with a microbial infection or infection with a microbe for example, a favorable response is killing or elimination of the microbe or bacteria, or control of, or inhibition of growth of the microbial infection in the subject or a subject at risk thereof (i.e., efficacy), and avoiding undue toxicity or other harm thereto (i.e., safety). Therefore, "efficacy" can refer to such choices that involve routine manipulation of conditions to achieve a desired effect or favorable response.

In some embodiments, the pharmaceutical composition can be administered to a subject as a bolus over a short time, such as once a day is a convenient dosing schedule. Alternatively, the effective daily dose can be divided into multiple doses for purposes of administration, for example, two to twelve doses per day. Dosage levels of active ingredients in a pharmaceutical composition can also be varied so as to achieve a transient or sustained concentration of the composition in the subject, especially in and around the area of the microbial infection or infection with a microbe, and to result in the desired therapeutic response or protection. It is also within the skill of the art to start doses at levels lower than required to achieve the desired therapeutic effect and to gradually increase the dosage until the desired effect is achieved.

The amount of the pharmaceutical compositions to be administered to a subject is dependent upon factors known to a persons of ordinary skill in the art such as bioactivity and bioavailability of the antimicrobial agent and silver-containing compound (e.g., half-life in the body, stability, and metabolism of the antimicrobial agent or silver-containing compound); chemical properties of the antimicrobial agent (e.g., molecular weight, hydrophobicity, and solubility); types of microbial strains, severity of the microbial infection, physical condition of a subject, and/or route and scheduling of administration. It will also be understood that the specific dose level of the composition comprising antimicrobial agents and a silver-containing compound as disclosed herein to be achieved for any particular subject can depend on a variety of factors, including age, gender, health, medical history, weight, combination with one or more other drugs, and severity of disease, and microbial strain or microorganism the subject is infected with, such as infection with multi-resistant bacterial strains.

Dosages, formulations, dosage volumes, regimens, and methods for analyzing results aimed at reducing the number of viable bacteria and/or activity can vary. Thus, minimum and maximum effective dosages vary depending on the method of administration. Suppression of the clinical changes associated with microbial infections or infection with a microbe can occur within a specific dosage range, which, however, varies depending on the microbe receiving the dosage, the route of administration, whether the antimicrobial agents are administered in conjunction with the silver-containing compound as disclosed herein, and in some embodiments with other co-stimulatory molecules, and the specific regimen administration. For example, in general, nasal administration requires a smaller dosage than oral, enteral, rectal, or vaginal administration.

In some embodiments, the pharmaceutical composition described herein can be used ex vivo. For example, blood products such as infected blood or blood suspected of having a microbial contamination can be treated with the pharmaceutical compositions described herein, prior to blood transfusion to a subject.

In some embodiments, the pharmaceutical compositions described herein can be adapted for use in wound dressing.

In some embodiments, the pharmaceutical composition can be formulated in an emulsion or a gel. The gel pharmaceutical composition can be placed on or implanted to a region of infected area.

The compositions can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE", 17th edition, 1985, incorporated herein by reference, may be consulted to prepare suitable preparations, without undue experimentation. With respect to compositions of the invention, however, any vehicle, diluent, or additive used should have to be biocompatible with cardiac stem cells.

The pharmaceutical compositions can be isotonic, i.e., they can have the same osmotic pressure as blood and lacrimal fluid. The desired isotonicity of the compositions of the invention can be accomplished using sodium chloride, or other pharmaceutically acceptable agents such as dextrose, boric acid, sodium tartrate, propylene glycol or other inorganic or organic solutes. In one embodiment, sodium chloride is used in buffers containing sodium ions.

Other exemplary compositions: Another aspect provided herein relates to compositions for treatment of a microbial biofilm or prevention of microbial contamination on a surface of a physical object, e.g., a medical device or equipment. In such embodiments, the compositions can further comprise any sterilizing chemicals such as detergents, disinfectants, and ammonium-based chemicals (e.g. quaternary ammonium compounds such as QUATAL, which contains 10.5% N-alkyldimethyl-benzlammonium HCl and 5.5% gluteraldehyde as active ingredients, Ecochimie Ltée, Quebec, Canada). Such sterilizing chemicals are typically used in the art for sterilizing industrial work surfaces (e.g. in food processing, or hospital environments), and are not suitable for administration to an animal.

In some embodiments where the compositions are used to coat a surface of a physical object, e.g., for prevention of a microbial contamination, the compositions can be formulated in coating compositions, e.g., comprising binders, organic solvents, and/or a solidifying agent, such that the composition applied on a surface of a physical object will form a coating on the surface of the physical object. One of skill in the art will readily know other ingredients that can be included in the coating compositions. When the physical objects are used in vivo (e.g., a medical device such as catheter), such compositions should be biocompatible and/or pharmaceutically acceptable.

Viscosity of the compositions can be maintained at the selected level using a thickening agent (e.g., pharmaceutically acceptable thickening agent depending on various applications). In one embodiment, methylcellulose is used because it is readily and economically available and is easy to work with. Other suitable thickening agents include, for example, xanthan gum, carboxymethyl cellulose, hydroxypropyl cellulose, carbomer, and the like. The preferred concentration of the thickener will depend upon the agent selected. The important point is to use an amount which will achieve the selected viscosity. Viscous compositions are normally prepared from solutions by the addition of such thickening agents.

Typically, any additives (in addition to an agent and/or a silver-containing compound described herein) can be present in an amount of 0.001 to 50 wt % solution in phosphate buffered saline, and the active ingredient is present in the order of micrograms to milligrams to grams, such as about 0.0001 to about 5 wt %, about 0.0001 to about 1 wt %, about 0.0001 to about 0.05 wt % or about 0.001 to about 20 wt %, about 0.01 to about 10 wt %, and about 0.05 to about 5 wt %. For any therapeutic composition to be administered to a subject in need thereof, and for any particular method of administration, it is preferred to determine toxicity, such as by determining the lethal dose (LD) and LD50 in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan.

Those skilled in the art will recognize that the components of the compositions should be selected to be biocompatible with respect to the active agent, e.g., an agent (e.g., antibiotic) and/or a silver-containing compound. This will present no problem to those skilled in chemical and pharmaceutical principles, or problems can be readily avoided by reference to standard texts or by simple experiments (not involving undue experimentation).

The compositions of the invention can be prepared by mixing the ingredients following generally-accepted procedures. For example, a composition comprising an agent described herein and a silver-containing compound can be re-suspended in an appropriate pharmaceutically acceptable carrier and the mixture can be adjusted to the final concentration and viscosity by the addition of water or thickening agent and possibly a buffer to control pH or an additional solute to control tonicity. Generally the pH can vary from about 3 to about 7.5. In some embodiments, the pH of the composition can be about 6.5 to about 7.5. Compositions can be administered in dosages and by techniques well known to those skilled in the medical and veterinary arts taking into consideration such factors as the age, sex, weight, and condition of the particular patient, and the composition form used for administration (e.g., liquid). Dosages for humans or other mammals can be determined without undue experimentation by a skilled artisan.

Selection of subjects or individuals amenable to the methods described herein.

In some embodiments, a subject selected for the method described herein or for the administration of a composition comprising at least one antimicrobial agent (e.g., an antibiotic) and a silver-containing compound can be a subject diagnosed with or at risk of a microbial infection. In some embodiments, a subject selected for the method described herein or for the administration of a composition described herein can be a subject diagnosed with or at risk of a Gram-negative microbial infection.

In some embodiments, the subject diagnosed with a microbial infection can be previously treated with at least one antimicrobial agent, for example, including at least two antimicrobial agents, at least three antimicrobial agents, at least four antimicrobial agents, at least five antimicrobial agents or more.

In some embodiments, the subject previously treated with at least one antimicrobial agent can be non-responsive to the prior antimicrobial agent. In such embodiments, the subject can be administered with a pharmaceutical composition comprising the same antimicrobial agent that was previously administered and a silver-containing compound. In other embodiments, the subject can be administered with a pharmaceutical composition comprising a different antimicrobial agent and a silver-containing compound.

In some embodiments, the subject currently being treated for a microbial infection can be selected and administered with a pharmaceutical composition described herein, e.g., to potentiate the antimicrobial effect. In some embodiments, the subject can be administered with a pharmaceutical composition in combination with his/her current treatment regimen.

Diagnosing a subject for a systemic microbial infection is known to one of ordinary skill in the art. For example, blood cultures are generally used to detect the presence of microbes such as bacteria or yeasts in the blood, to identify the microbe(s) present, and then to provide corresponding treatment.

In some embodiments, if a subject is diagnosed positive in a blood culture, the subject can be administered with a pharmaceutical composition described herein. In some embodiments, if blood cultures are positive (i.e., microbes are found in a blood culture), other diagnostic tests such as a complete blood count and/or a chemical test can be performed to confirm if the tested subject is afflicted with a microbial infection. A complete blood count can also be used to indicate or confirm whether a subject is suffering from a microbial infection or at risk of a microbial infection. For example, a complete blood count showing an increased number of white blood cells, e.g., a white blood cell count of a subject's blood sample above a normal range, e.g., by at least about 5%, or at least about 10%, can indicate a microbial infection. A blood sample showing an increased level of complements, such as C3, can indicate a microbial infection. Other than a blood culture, a urine, sputum, and/or cerebrospinal fluid (CSF) culture can also be performed to indicate a possible source of microbial infection that may have spread to the blood.

In some embodiments, if the subject is suspected of having a microbial infection, the subject can be administered with a pharmaceutical composition. In some embodiments, the subject suspected of having a microbial infection and waiting for further test results for confirmation can be administered with a pharmaceutical composition described herein. In such embodiments, when the test results become available, the subject can stop taking the current pharmaceutical composition if he or she is determined to be clear of a microbial infection. On the other hand, if the subject is determined to have a microbial infection, the subject can be continuously administered with the same prior pharmaceutical composition, e.g., in the same or a different administration schedule, or the subject can be administered with a different pharmaceutical composition described herein, e.g., based on the types of microbes determined in the blood cultures and/or its anticipated antibiotic susceptibilities.

In some embodiments, a subject showing a clinical presentation or symptom of a microbial infection (e.g., a microbial infection on skin) recognized by a skilled practitioner can be administered with a pharmaceutical composition described herein.

In some embodiments, a subject with an open wound can be administered with a pharmaceutical composition, e.g., to treat and/or prevent a microbial infection. In some embodiments, a subject with an open wound infected with or at risk of being infected with a Gram-negative microbe can be administered with a pharmaceutical composition.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In certain embodiments of the aspects described herein, the subject is a mammal, e.g., a primate, e.g., a human. The terms, "individual" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with microbes. In addition, the methods and compositions described herein can be used to treat domesticated animals and/or pets.

Microbes or microbial infections

The term "infection" or "microbial infection" which are used interchangeably herein refers to, in its broadest sense, any infection caused by a microorganism or a microbe and includes bacterial infections, fungal infections, yeast infections, protozomal infections, and any combinations thereof.

As used herein, the term "microbes" generally refers to Gram-positive and Gram-negative microorganisms, including bacteria, fungi, protozoan, archaea, protists, e.g., algae, and a combination thereof. The term "microbes" also includes pathogenic microbes, e.g., but not limited to, bacteria causing diseases such as plague, tuberculosis and anthrax; protozoa causing diseases such as malaria, sleeping sickness and toxoplasmosis; and fungi causing diseases such as ringworm, candidiasis or histoplasmosis.

In some embodiments, the term "microbes" can also encompass drug-resistant microbes (e.g., drug-resistant bacteria). The term "drug-resistant microbes" as used herein refers to microbes that are resistant to at least one antimicrobial agent such as an antibiotic in one or more classes of antibiotics. This includes those microbes that are resistant to at least two, at least three, at least four or more antimicrobial agents such as antibiotics in one or more classes of antibiotics.

In some embodiments, the term "microbes" can also encompass persistent microbes (e.g., persistent bacteria). The term "persistent microbes" is used herein in reference to a metabolically dormant subpopulation of microbes, for example, bacteria, which are not sensitive to antimicrobial agents such as antibiotics. Persistent microbes (e.g., persistent bacteria) typically are not responsive (i.e. are not killed by the antibiotics) as they have non-lethally down-regulated the pathways on which the antimicrobial agents act, i.e., the persistent microbes have down-regulated the pathways which are normally inhibited or corrupted by the antimicrobial agents, such as the transcription, translation, DNA replication and cell wall biosynthesis pathways. Persistent microbes can develop at non-lethal (or sub-lethal) concentrations of the antimicrobial agent.

In certain embodiments, the term "microbes" refers to Gram-negative bacteria. A Gram negative bacterium is a bacterium with a cell wall structure that does not retain the methyl violet component of Gram's stain after elution with an organic solvent such as ethyl alcohol. See, e.g., Salton M J R, Kim K S (1996). Structure. in: Baron's Medical Microbiology (Baron S et al., eds.) (4th ed.). The pink counterstain makes the Gram-negative bacteria appear pink. Gram negative bacteria are characterized by two cellular membranes separated by a periplasmic space. The periplasmic space is external to the inner, cytoplasmic membrane. On the other side of the periplasm is an outer membrane comprising lipopolysaccharide (LPS) and capsular polysaccharide. Porin proteins typically are present on the outer LPS layer. Gram negative bacteria include, without limitation, *Escherichia* spp. (e.g., *E. Coli*); *Salmonella* spp. (e.g., *S. typhimurium*); *Pseudomonas* spp. (e.g., *P. aeruginosa*); *Burkholderia* spp.; *Neisseria* spp. (e.g., *N. meningitides, N. gonorrhoeae*); *Haemophilus* spp. (*H. influenzae*); *Shigella* spp. *Bacterioides* spp.; *Campylobacter* spp.; *Brucella* spp.; *Vibrio* spp.; *Yersinia* spp.; *Helicobacter* spp.; *Calymmatobacterium* spp.; *Legionella* spp.; *Leptospira* spp.; *Borrelia* spp., *Bordetella* spp.; *Klebsiella* spp. (e.g., *K. pneumoniae*); *Treponema* spp.; *Francisella* spp.; *Moraxella* spp.; *Stenotrophomonas* spp.; *Bdellovibrio* spp.; *Acinetobacter* spp.; *Spirochaetes; Proteus* spp. (e.g., *Proteus microbilis*); *Enterobacter; Serratia* spp. (e.g., *S. plymuthica, S. liquefaciens, S. rubidaea*, and *S. odoriferae*); *Gardnerella* spp., and any combinations thereof. Many of these organisms are known to be pathogenic to animals and/or plants, including mammals such as humans, and can cause diseases and disorders such as enteritis, septicaemia, meningitis, enteric fever, pneumonia, epiglottitis, cellulitis, diarrhea and sexually transmitted diseases. For example, Gram-negative cocci include three microorganisms, which cause a sexually transmitted disease (e.g., *Neisseria gonorrhoeae*), a meningitis (e.g., *Neisseria meningitidis*), and respiratory symptoms (e.g., *Moraxella catarrhalis*). Some of Gram-negative bacilli can cause respiratory problems (e.g., *Hemophilus influenzae, Klebsiella pneumoniae, Legionella pneumophila, Pseudomonas aeruginosa*), urinary problems (e.g., *Escherichia coli, Proteus mirabilis, Enterobacter cloacae, Serratia marcescens*), and gastrointestinal problems (e.g., *Helicobacter pylori, Salmonella enteritidis, Salmonella typhi*). Gram-negative bacteria associated with nosocomial infections can also include, but are not limited to, *Acinetobacter baumannii*, which cause bacteremia, secondary meningitis, and ventilator-associated pneumonia in intensive-care units of hospital establishments.

In certain embodiments, the term "microbes" refers to Gram-positive bacteria. Due to structural differences in bacterial cell walls, Gram-positive bacteria generally retain the methyl violet component of Gram's stain after elution with an organic solvent such as ethyl alcohol. Thus, Gram-positive bacteria are bacteria that are stained dark blue or violet by Gram staining. Gram-positive organisms are able to retain the crystal violet stain because of the high amount of peptidoglycan in the cell wall. Gram-positive cell walls typically lack the outer membrane found in Gram-negative bacteria. Exemplary Gram-positive microorganisms include, but are not limited to, *Staphylococcus aureus, Staphylococci, Streptococci, Enterococci, Carynebacteria, Clostrid-* rium, *Listeria* and *Bacillus* species. Many of these Gram-positive bacteria are known to be pathogenic and can cause diseases in a subject.

In some embodiments, the microbes are Gram-positive or Gram-negative fungi, e.g., yeast, molds. Exemplary fungi and yeast include, but are not limited to, *Cryptococcus neoformans, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Aspergillus fumigatus, Aspergillus flavus, Aspergillus clavatus, Cryptococcus neoformans, Cryptococcus laurentii, Cryptococcus albidus, Cryptococcus gattii, Histoplasma capsulatum, Pneumocystis jirovecii* (or *Pneumocystis carinii*), *Stachybotrys chartarum*, and any combination thereof. One of skilled in the art can determine whether a fungus is Gram-positive or Gram-negative by performing an art-recognized Gram stain test.

In some embodiments, the microbial infection that can be treated with methods and compositions described herein can be caused by gram-negative bacterium, for example, *P. aeruginosa, A. bumannii, Salmonella* spp, *Klebsiella pneumonia, Shigella* spp. and/or *Stenotrophomonas maltophilia*. Examples of microbial infections include bacterial wound infections, mucosal infections, enteric infections, septic conditions, pneumonia, trachoma, onithosis, trichomoniasis and salmonellosis, especially in veterinary practice.

Examples of infections caused by *P. aeruginosa* include, without limitations: A) Nosocomial infections: 1. Respiratory tract infections in cystic fibrosis patients and mechanically-ventilated patients; 2. Bacteraemia and sepsis; 3, Wound infections, particularly in burn wound patients; 4. Urinary tract infections; 5. Post-surgery infections on invasive devises; 6. Endocarditis by intravenous administration of contaminated drug solutions; 7, Infections in patients with acquired immunodeficiency syndrome, cancer chemotherapy, steroid therapy, hematological malignancies, organ transplantation, renal replacement therapy, and other situations with severe neutropenia. B) Community-acquired infections: 1. Community-acquired respiratory tract infections; 2. Meningitis; 3. Folliculitis and infections of the ear canal caused by contaminated waters; 4. Malignant otitis externa in the elderly and diabetics; 5. Osteomyelitis of the caleaneus in children; 6. Eye infections commonly associated with contaminated contact lens; 7. Skin infections such as nail infections in people whose hands are frequently exposed to water; 8. Gastrointestinal tract infections; 9. Muscoskeletal system infections.

Examples of infections caused by *A. baumannii* can include, without limitation: A) Nosocomial infections: 1. Bacteraemia and sepsis, 2. Respiratory tract infections in mechanically ventilated patients; 3. Post-surgery infections on invasive devices; 4. Wound infectious, particularly in burn wound patients; 5. Infection in patients with acquired immunodeficiency syndrome, cancer chemotherapy, steroid therapy, hematological malignancies, organ transplantation, renal replacement therapy, and other situations with severe neutropenia; 6. Urinary tract infections; 7. Endocarditis by intravenous administration of contaminated drug solutions; 8. Cellulitis. B) Community-acquired infections: 1. Community-acquired pulmonary infections; 2. Meningitis; 3. Cheratitis associated with contaminated contact lens; 4. War-zone community-acquired infections. C) Atypical infections, e.g., chronic gastritis.

Examples of infections caused by *Stenotrophomas maltophilia* can include B acteremia, pneumonia, meningitis, wound infections and urinary tract infections. Some hospital-acquired infections can be caused by contaminated disinfectant solutions, respiratory devices, monitoring instruments and ice machines. Infections usually occur in debilitated patients with impaired host defense mechanisms.

Examples of infections caused by *Klebsiella pneumoniae* can include community-acquired primary lobar pneumonia, (e.g., in people with compromised pulmonary function and alcoholics). It can also cause, e.g., wound infections, soft tissue infections and urinary tract infections.

Examples of infections caused by *Salmonella* app. Can be acquired by eating contaminated food products. Infections include enteric fever, enteritis and bacteremia.

Examples of infections caused by *Shigella* spp. include, but not limited to, gastroenteritis (shigellosis).

Microbial infection or contamination can be present anywhere. In some embodiments, the microbial infection can be present in a subject. In some embodiments, the microbial infection or contamination can be present on a surface of a physical object (e.g., medical device). In some embodiments, the microbial infection or contamination can be present on an environmental surface (e.g., a building surface, and plant surface).

Treatment of microbial biofilms using the methods and compositions described herein A biofilm is an aggregate of microbes which adhere to each other and/or to a surface, and can form on living or non-living surfaces in various settings. Biofilms form in response to many factors, which can include cellular recognition of specific or non-specific attachment sites on a surface, nutritional cues, or in some cases, by prior exposure of microbes to sub-inhibitory concentrations of antibiotics. In some cases, microbes can form a biofilm if left untreated.

Biofilms are typically less susceptible to conventional antibiotics, antimicrobials, and biocides. In some cases, microbes (e.g., bacteria) in a biofilm can be up to 4,000 times more resistant (i.e., less susceptible) than the same microbe in a single-cell state.

The inventors have demonstrated that the use of a silver-containing compound in combination with an antimicrobial agent (e.g., an antibiotic) can increase the activity of the antimicrobial agent, and/or can also enable the antimicrobial agent to treat or target additional microbial strains. Accordingly, methods for treating a surface determined to have or suspected of having a microbial biofilm (e.g., a Gram-negative microbial biofilm) are also provided herein. In some embodiments, the method comprises administering to a surface that has been determined to have a microbial biofilm (e.g., a Gram-negative microbial biofilm) an effective amount of a composition comprising an antimicrobial agent and a potentiating amount of a silver-containing compound. In some embodiments, the antimicrobial agent can be an antimicrobial agent that is not effective for treatment of the microbial biofilm by itself. In some embodiments, the effective amount of the composition can comprise an antimicrobial agent and a silver-containing compound, each of which is present in a sub-inhibitory concentration by itself.

A person having skill in the art would recognize that many microbes (e.g., bacteria) form biofilms. Wolcott et al., 2008 and James et al., 2008. For example, a Gram-negative bacteria *Pseudomonas aeruginosa* is known to form biofilms and is an important causative agent of emerging nosocomial infections (also known as hospital-acquired infection such as catheter-associated urinary tract infection). Dental plaque is a biofilm on the surfaces of the teeth and can consist of Gram-negative or Gram-positive bacterial cells (e.g., *Streptococcus mutans* and *Streptococcus sanguis*), salivary polymers and bacterial extracellular products.

Gram-negative *Legionella* bacteria are known to grow under certain conditions in biofilms, in which they are protected against disinfectants. Gram-negative *Neisseria gonorrhoeae* is a human pathogen that has been demonstrated as forming biofilms on glass surfaces and over human cells (e.g., in sexually transmitted infection gonorrhea). Other types of bacteria that form biofilms include *Staphylococcus aureus* and *Enterococcus* sp.

Biofilms are known to be involved in a wide variety of microbial infections in the body of a subject. Infectious processes in which biofilms have been implicated include common problems such as urinary tract infections, catheter infections, middle-ear infections, formation of dental plaque, gingivitis, coating contact lenses, endocarditis, and infections in cystic fibrosis. Biofilms can also be formed on the inert surfaces of medical devices such as catheters, prosthetic cardiac valves and intrauterine devices. Microbial biofilms can also impair wound healing (e.g., cutaneous wound healing) and reduce topical antibacterial efficiency in healing or treating infected skin wounds.

Biofilms on medical devices can be composed of gram-positive or gram-negative microbes (e.g., bacteria or yeasts). Bacteria commonly found on the medical devices include the gram-positive *Enterococcus faecalis* (*E. faecalis*), *Staphylococcus epidermidis* (*S. epidermidis*), *Staphylococcus aureus* (*S. aureus*), *Streptococcus viridans* (*St. viridans*); and the gram-negative *Escherichia coli* (*E. Coli*, *Klebsiella pneumoniae* (*K. pneumoniae*), *Proteus mirabilis* (*P. mirabilis*) and *Pseudomonas aeruginosa* (*P. aeruginosa*) (Donlan, R. M., Emerging Infectious Diseases, 7:277-281, 2001). The microbes most commonly found in urinary catheter biofilms are *Staphylococcus epidermidis*, *Enterococcus faecalis*, *E. Coli*, *Proteus mirabilis*, *Pseudomonas aeruginosa* and *Klebsiella pneumoniae*. In the case of vascular catheters, *Staphylococcus aureus* and *Staphylococcus epidermidis* account for almost 70-80% of all infectious organisms. *Candida albicans* accounts for about 10-15% of catheter infections. Gram-negative bacilli account for almost 60-70%, enterococci for about 25% and *Candida albicans* for about 10% of cases of urinary tract infections.

Additional examples of bacteria that can produce biofilms (biofilm bacteria) include bacteria such as *Staphylococcus epidermidis*, *Enterococcus faecalis*, *E. Coli*, *Proteus mirabilis*, *Pseudomonas aeruginosa*, *Klebsiella pneumoniae*, *Staphylococcus aureus*, and *Streptococcus* viridans. These bacteria are commonly found associated with medical devices including catheters. Other bacteria that form biofilms include *Klebsiella oxytoca, Staphylococcus saprophyticus, Providencia stuartii, Citrobacter freundii* and *Serratia marcescens*.

Preventing formation of microbial biofilms on medical devices is also within the scope of the invention. For example, methods for preventing formation of a microbial biofilm on a surface (e.g., a surface of a medical device or equipment) are also provided herein. The method comprises coating a surface with an effective amount of a composition comprising an antimicrobial agent and a potentiating amount of a silver-containing compound. In some embodiments, the antimicrobial agent can be an antimicrobial agent that is not effective for treatment of the microbial biofilm by itself. In some embodiments, the effective amount of the composition can comprise an amount of an antimicrobial agent and a silver-containing compound, each of which is present in a sub-inhibitory amount by itself.

Examples of medical devices that can be protected and coated using some embodiments of the compositions described herein include tubings and other surface medical devices, such as urinary catheter, mucous extraction catheter, suction catheter, umbilical cannula, contact lenses, intrauterine devices, intravaginal and intraintestinal devices, endotracheal tubes, bronchoscopes, dental prostheses and orthodontic devices, surgical instruments, dental instruments, tubings, dental water lines, dental drain tubes, fabrics, paper, indicator strips (e.g., paper indicator strips or plastic indicator strips), adhesives (e.g., hydrogel adhesives, hot-melt adhesives, or solvent-based adhesives), bandages, tissue dressings or healing devices and occlusive patches, and any other surface devices used in the medical field. The devices may include electrodes, external prostheses, fixation tapes, compression bandages, and monitors of various types. Medical devices can also include any device which can be placed at the insertion or implantation site such as the skin near the insertion or implantation site, and which can include at least one surface which is susceptible to colonization by microbe-embedded biofilms. In some embodiments, the composition of the invention can be integrated into an adhesive, such as tape, thereby providing an adhesive, which can prevent growth or proliferation of a microbe-embedded biofilm on at least one surface of the adhesive. Medical devices can also include surfaces of equipment in operating rooms, emergency rooms, hospital rooms, clinics, and bathrooms.

The methods and compositions as disclosed herein comprising an antimicrobial agent can also be used in various fields as where antiseptic treatment or disinfection of materials is required, for example, surface disinfection, including for use in bioremediation, such as industry settings, including cleaning of heating and cooling systems, such as HVAC systems.

By way of example only, *Legionella* species are the causative agent of the human Legionnaires' disease and the lesser form, Pontiac fever. *Legionella* transmission is via aerosols—the inhalation of mist droplets containing the bacteria. Common sources include cooling towers, domestic hot-water systems, fountains, and similar disseminators that tap into a public water supply. Natural sources of *Legionella* include freshwater ponds and creeks. Once inside a host, incubation may take up to two weeks. Initial symptoms are flu-like, including fever, chills, and dry cough. Advanced stages of the disease cause problems with the gastrointestinal tract and the nervous system and lead to diarrhea and nausea. Other advanced symptoms of pneumonia may also present. However, the disease is generally not a threat to most healthy individuals, and tends to lead to harmful symptoms only in those with a compromised immune system and the elderly. Consequently, it should be actively checked for in the water systems of hospitals and nursing homes. Accordingly, some embodiments of the present invention can be also used to treat and reduce bacterial infections in all transmitting parts of HVAC systems possibly to being contaminated, as well as the entire water distribution and storage system.

Embodiments of the various aspects described herein can be illustrated by the following numbered paragraphs.

1. A method for treating an individual having a Gram-negative microbial infection comprising administering to an individual that has been determined to have a Gram-negative microbial infection an effective amount of a pharmaceutical composition comprising an antibiotic that is not effective for treatment of the Gram-negative microbial infection when used alone, and a potentiating amount of a silver-containing compound, wherein the potentiating amount of the silver-containing compound is sufficient to expand the spectrum of the antibiotic, but not enough to be toxic by itself to a population of the microbes.

2. The method of paragraph 1, wherein the antibiotic that is not effective for treatment of the Gram-negative microbial infection when used alone is an antibiotic that does not penetrate through an outer membrane of the Gram-negative microbe.

3. The method of paragraph 1 or 2, wherein the antibiotic that is not effective for treatment of the Gram-negative microbial infection when used alone is an antibiotic that treats a Gram-positive microbial infection.

4. The method of any of paragraphs 1-3, wherein the antibiotic that treats a Gram-positive microbial infection is vancomycin, teicoplanin, moenomycin, dicloxacillin, daptomycin, linezolid, oxacillin, nafcillin, or a combination thereof.

5. The method of any of paragraphs 1-4, wherein the potentiating amount of the silver-containing compound is an amount below a threshold level required to effectively treat a Gram-negative microbial infection when used alone.

6. The method of paragraph 5, wherein the potentiating amount of the silver-containing compound comprises silver in a concentration of about 1 µM to about 30 µM.

7. The method of paragraph 6, wherein the potentiating amount of the silver-containing compound comprises silver in a concentration of about 5 µM to about 20 µM.

8. The method of paragraph 7, wherein the potentiating amount of the silver-containing compound comprises silver in a concentration of about 15 µM to about 20 µM.

9. The method of any of paragraphs 1-8, wherein the silver-containing compound comprises elemental silver.

10. The method of any of paragraphs 1-9, wherein the silver-containing compound comprises a silver salt or ionic silver.

11. The method of paragraph 10, wherein the silver salt or ionic silver is selected from the group consisting of silver nitrate, silver acetate, silver benzoate, silver carbonate, silver iodate, silver iodide, silver lactate, silver laurate, silver oxide, silver palmitate, silver sulfadiazine, and any combinations thereof.

12. The method of any of paragraphs 1-11, wherein the Gram-negative microbe is selected from the group consisting of *E. Coli, Salmonella, Shigella, Pseudomonas, Moraxella, Helicobacter, Stenotrophomonas, Bdellovibrio, Legionella, Acinetobacter, spirochaetes, Neisseria gonorrhoeae, Neisseria meningitides, Hemophilus influenzae, Klebsiella pneumoniae, Proteus mirabilis, Enterobacter, Serratia*, and any combinations thereof.

13. A method for delivering to a Gram-negative microbe an agent that does not penetrate across an outer membrane of the Gram-negative microbe when used alone, comprising contacting the Gram-negative microbe with an effective amount of a composition comprising the agent and a potentiating amount of a silver-containing compound, wherein the potentiating amount of the silver-containing compound is sufficient to increase membrane permeability of the Gram-negative microbe to the agent, thereby delivering the agent to the Gram-negative microbe.

14. The method of paragraph 13, wherein the agent is an antibiotic specific for treatment of a Gram-positive microbial infection.

15. The method of paragraph 13, wherein the agent is an optical molecule.

16. A method for treating a surface having a Gram-negative microbial biofilm comprising administering to a surface that has been determined to have a Gram-negative microbial biofilm an effective amount of a composition comprising an agent that is not effective for treatment of the Gram-negative microbial biofilm when used alone, and a potentiating amount of a silver-containing compound, wherein the potentiating amount of the silver-containing compound is sufficient to expand the spectrum of the agent, but not enough to be effective by itself to treat the biofilm.

17. A method for treating a patient having a bacterial infection, comprising, administering an antibiotic and a silver-containing compound to the patient, where one or both of the antibiotic and silver-containing compound are administered at a dose below which would be effective alone.

18. The method of paragraph 17, wherein the bacterial infection is a gram-negative bacterial infection.

19. The method of paragraph 17 or 18, wherein the antibiotic is daptomycin, vancomycin, teicoplanin, moenomycin, dicloxacillin, linezolid, oxacillin, nafcillin, or a combination thereof.

20. The method of any of paragraphs 17 to 19, wherein the potentiating amount of the silver-containing compound is an amount below a threshold level required to effectively treat a Gram-negative microbial infection when used alone.

21. The method of paragraph 20, wherein the potentiating amount of the silver-containing compound comprises or provides silver in a concentration of about 1 µM to about 30 µM.

22. The method of paragraph 21, wherein the potentiating amount of the silver-containing compound comprises or provides silver in a concentration of about 5 µM to about 20 µM.

23. The method of paragraph 21, wherein the potentiating amount of the silver-containing compound comprises or provides silver in a concentration of about 15 µM to about 20 µM.

24. The method of any of paragraphs 17 to 23, wherein the silver-containing compound comprises elemental silver.

25. The method of any of paragraphs 17 to 23, wherein the silver-containing compound comprises a silver salt or ionic silver.

26. The method of any one of paragraphs 17 to 23, wherein the silver salt or ionic silver is selected from silver nitrate, silver acetate, silver benzoate, silver carbonate, silver iodate, silver iodide, silver lactate, silver laurate, silver oxide, silver palmitate, silver sulfadiazine, and any combinations thereof.

27. The method of any of paragraphs 18 to 26, wherein the Gram-negative microbe is selected from *E. Coli, Salmonella, Shigella, Pseudomonas, Moraxella, Helicobacter, Stenotrophomonas, Bdellovibrio, Legionella, Acinetobacter, spirochaetes, Neisseria gonorrhoeae, Neisseria meningitides, Hemophilus influenzae, Klebsiella pneumoniae, Proteus mirabilis, Enterobacter, Serratia*, and any combinations thereof.

28. The method of any of paragraphs 17 to 27, wherein the antibiotic is daptomycin.

29. The method of paragraph 28, wherein the daptomycin is co-formulated with the silver-containing compound.

30. The method of paragraph 29, wherein the daptomycin and silver-containing compound are administered intravenously.

31. The method of paragraph 30, wherein the daptomycin is administered at less than 4 mg/kg.

32. The method of any of paragraphs 17 to 31, wherein the daptomycin and silver-containing compound are administered separately.

33. A pharmaceutical combination comprising a therapeutically effective amount of daptomycin, and a potentiating amount of a silver-containing compound.

Some Selected Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

The articles "a" and "an" are used herein to refer to one or to more than one (i.e., at least one) of the grammatical object of the article. By way of example, "an element" means one element or more than one element. Thus, in this specification and the appended claims, the singular forms "a," "an," and "the" include plural references unless the context clearly dictates otherwise. Thus, for example, reference to a composition comprising "an agent" includes reference to two or more agents.

In one respect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of" This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The terms "increase" or "potentiate" as used in the context of the activity of an antimicrobial agent or membrane permeability of a microbe generally means an increase in the efficacy of the antimicrobial agent or membrane permeability of a microbe by a statically significant amount relative to in the absence of the silver-containing compound. For example, a potentiated activity can be at least 2-fold, at least 3-fold, at least 4-fold, at least 5-fold, at least 10-fold increase or greater as compared to in the absence of the silver-containing compound.

As used herein, the term "administering" and "introducing" are used interchangeably and refer to the placement of a composition described herein into an individual or a surface infected by a microbe, by a method or route which results in at least partial localization of the composition at a desired site such that desired effect is produced. Routes of administration suitable for the methods of the invention include, but are not limited to, topical administration or systemic administration. The compositions described herein can be administered by any appropriate route which can results in an indicated effect as described herein.

The term "contacting" as used herein refers to any suitable means for delivering, or exposing, an agent to at least one microbe. Exemplary delivery methods include, but are not limited to, direct delivery to cell culture medium, delivery to a substrate (e.g., agar substrate) in which microbes are located, e.g., via perfusion or injection, or other delivery method well known to one skilled in the art. In one embodiment, a composition comprising an agent to be delivered to the microbe and a silver-containing compound can be added to the cell culture medium or the substrate in which microbes are cultured.

As used herein, the term "peptidomimetic" refers to a molecule capable of folding into a defined three-dimensional structure similar to a natural peptide

EXAMPLES

The examples presented herein relate to methods for treating Gram-negative microbes, e.g., *E. Coli*, with a silver-containing compound (e.g., silver nitrate), alone or in combination with an antibiotic. In particular embodiments, a silver-containing compound (e.g., silver nitrate) can broaden the spectrum of activity of an antibiotic specific for Gram-positive microbes for treatment of Gram-negative microbes. Throughout this application, various publications are referenced. The disclosures of all of the publications and those references cited within those publications in their entireties are hereby incorporated by reference into this application in order to more fully describe the state of the art to which this invention pertains. The following examples are not intended to limit the scope of the paragraphs to the invention, but are rather intended to be exemplary of certain embodiments. Any variations in the exemplified methods which occur to the skilled artisan are intended to fall within the scope of the present invention.

Example 1

Figure 1B:
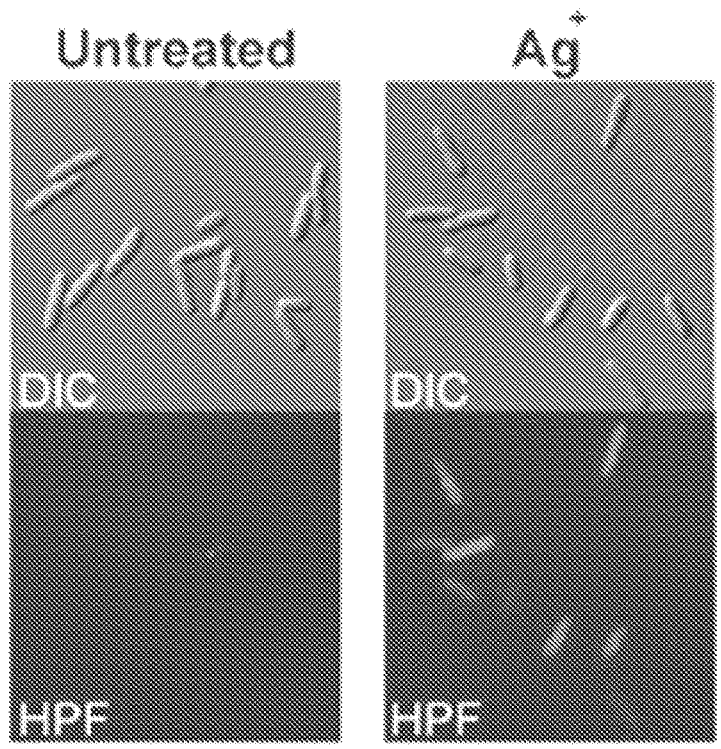
Figure 1C:
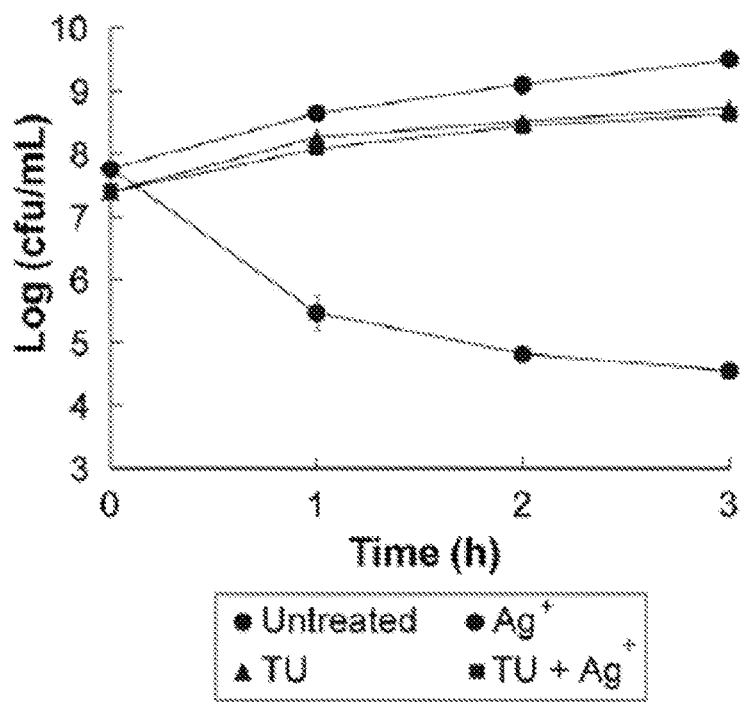

Identification of the Mechanistic Effects of Ionic Silver on Gram-Negative Bacteria Ionic silver ($Ag^+$) in a silver nitrate salt ($AgNO_3$) was used as a model silver salt to investigate the mechanistic effects of silver on Gram-negative bacteria. Silver nitrate demonstrated significant bactericidal activity at 30 µM against exponentially growing *E. coli*, a model Gram-negative bacterium (FIG. 1A). Production of reactive oxygen species (ROS), such as hydroxyl radicals (OH•), has been previously discussed to be part of a common mechanism of cell death induced by bactericidal antibiotics [13, 14]. Accordingly, it was sought to determine if ionic silver could affect the production of ROS. Hydroxyl radicals were measured in untreated *E. coli* cells and in cells treated with $Ag^+$ for one hour, using 3'-(p-hydroxyphenyl) fluorescein dye [15]. $Ag^+$-treated cells exhibited detectable increases in fluorescence compared to untreated cells, indicating increased OH• production (FIG. 1B). Moreover, addition of thiourea, an ROS scavenger [16], inhibited $Ag^+$-induced bacterial cell death, further supporting that ROS production is, at least partly, required for the bactericidal activity (FIG. 1C).

Figure 2A:
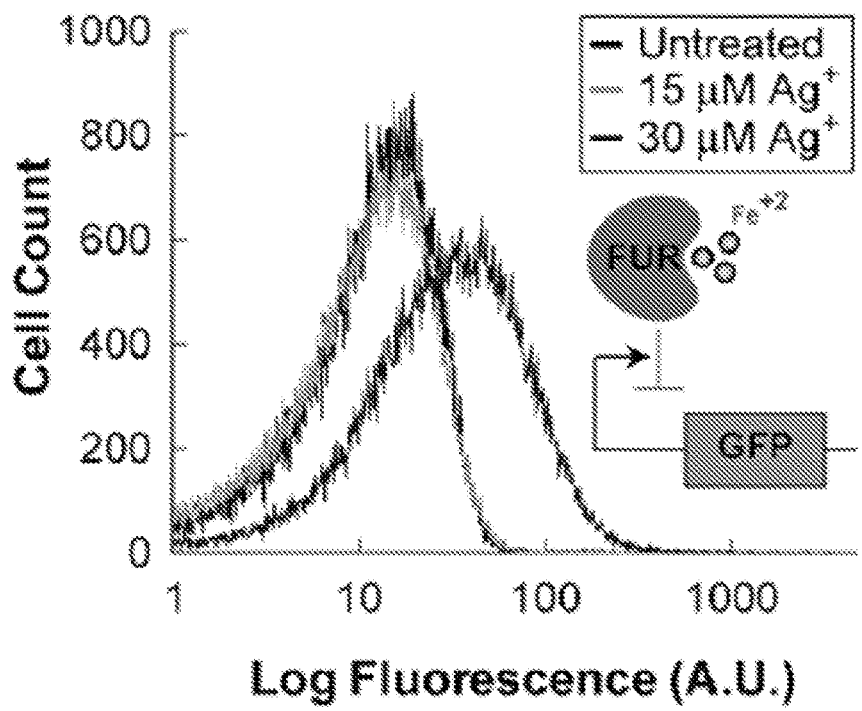
FIGS. 2A-2E show that $Ag^+$ induces OH• production through iron misregulation. Direct interaction between $Ag^+$ and Fe—S clusters leads to iron misregulation, leaking of $Fe^{+2}$ and the overproduction of OH• radicals.
Figure 2B:
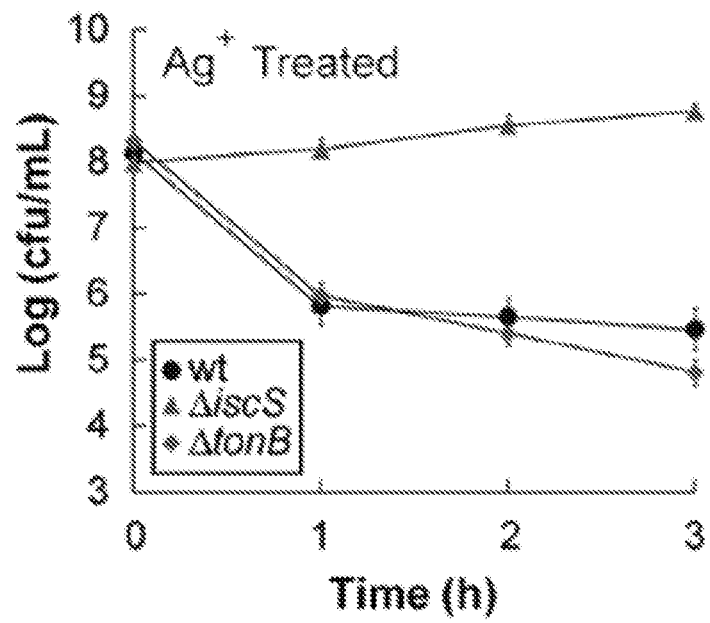
Figure 2C:
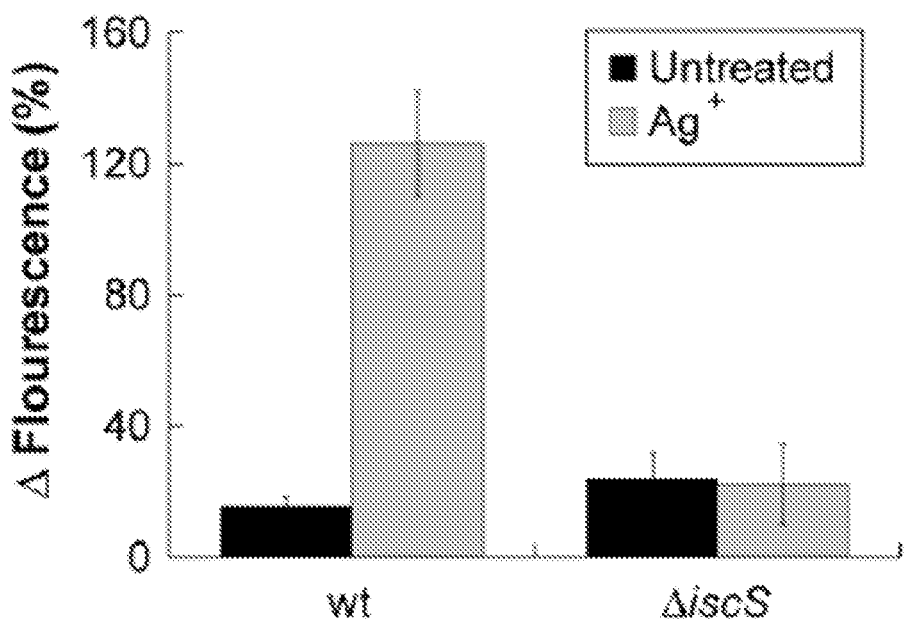

Hydroxyl radicals are a product of Fenton chemistry, where free iron plays a key role [17]. Accordingly, the effect of $Ag^+$ on iron homeostasis was measured by using an engineered promoter strain that produces the green fluorescent protein (GFP) in response to Fur, a master regulator of iron metabolism [18]. After one hour of $Ag^+$ treatment, the reporter strain exhibited significantly increased fluorescence relative to untreated cells (FIG. 2A), indicating a disruption in iron levels within the cell. The effect of $Ag^{3o}$ on iron regulation was investigated using two mutant strains with impaired iron regulation: a ΔtonB strain which has a blocked exogenous iron uptake system [19] and an ΔiscS strain which exhibits a smaller number of internal Fe—S clusters [20]. ΔtonB had similar sensitivity to $Ag^+$ as the wildtype strain, whereas ΔiscS exhibited a bacteriostatic phenotype when subjected to $Ag^+$ treatment (FIG. 2B). ΔiscS also exhibited significantly lower OH• production in response to $Ag^+$ treatment compared to wildtype cells (FIG. 2C). These findings indicate that internal iron from Fe—S clusters can, in part, play an important role in $Ag^+$-mediated cell death.

Figure 2D:
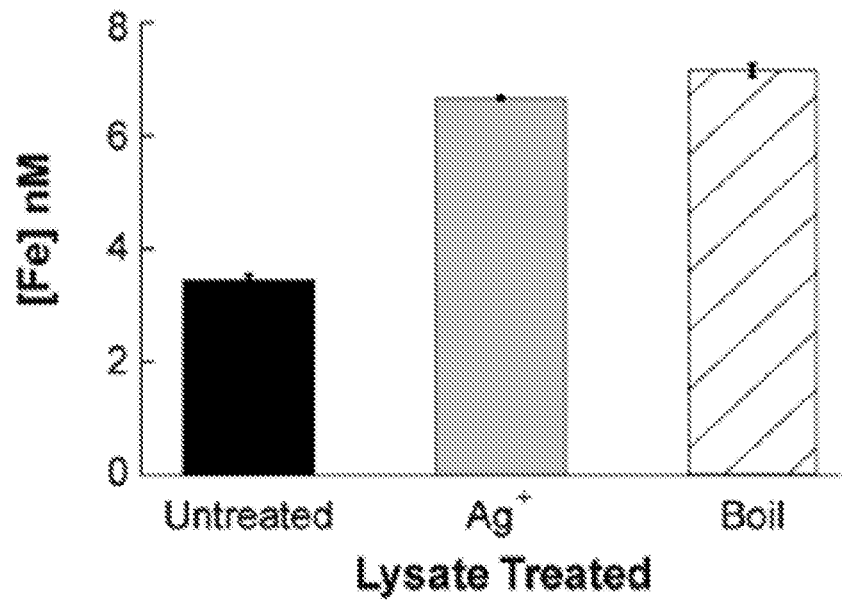
Figure 2E:
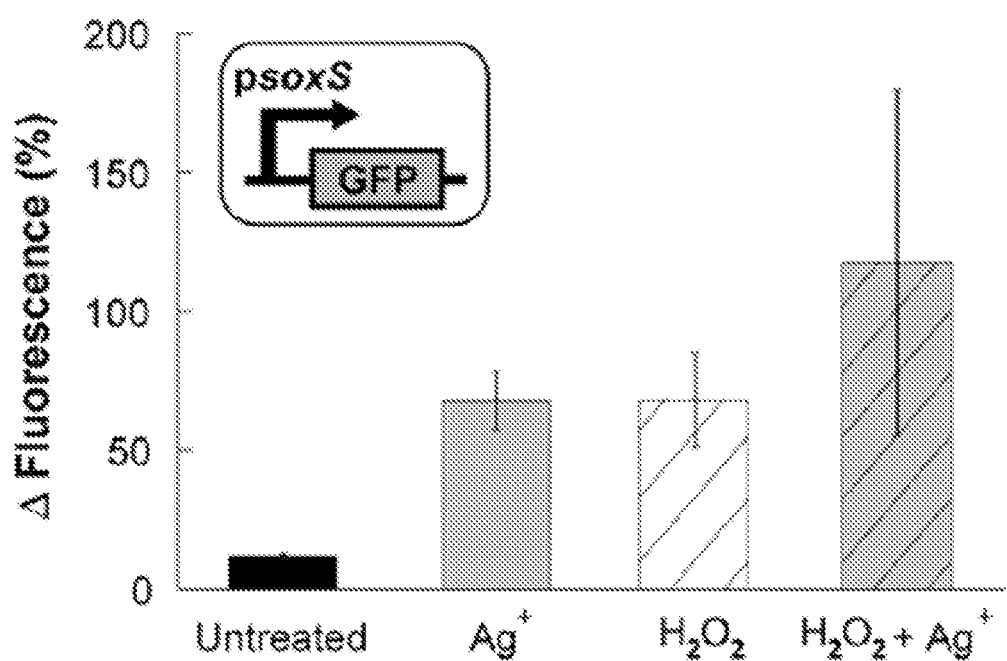

Transition metals, such as copper and zinc, can break down or inactivate Fe—S clusters [21] and cause leakage of $Fe^{+2}$. As silver is a transition metal, it was sought to determine if silver could disrupt Fe—S clusters and cause leakage of $Fe^{+2}$. The $Fe^{+2}$ levels were measured using Ferene-S, a colorimetric dye [22], in an $Ag^+$-treated *E. Coli* cell lysate. The levels of absorbance was compared to a positive control (e.g., a cell lysate heated to 90° C. to disrupt Fe—S clusters), and a negative control (e.g., an untreated lysate). $Ag^+$-treated lysates were determined to have higher $Fe^{+2}$ levels relative to the untreated lysate (FIG. 2D), indicating that $Ag^+$ can directly interact and disrupt Fe—S clusters. As stress-induced superoxide is also previously known to disrupt Fe—S clusters [18], the response of a soxS reporter strain to $Ag^+$ treatment was measured and indicated that $Ag^+$ can induce superoxide production (FIG. 2E). This finding indicates that $Ag^+$ can also indirectly lead to $Fe^{+2}$ leakage, for example, by stimulating the production of superoxide. Together these findings indicate that $Ag^+$ can disturb internal iron homeostasis, at least partly, by directly and indirectly disrupting intracellular Fe—S clusters.

Figure 3A:
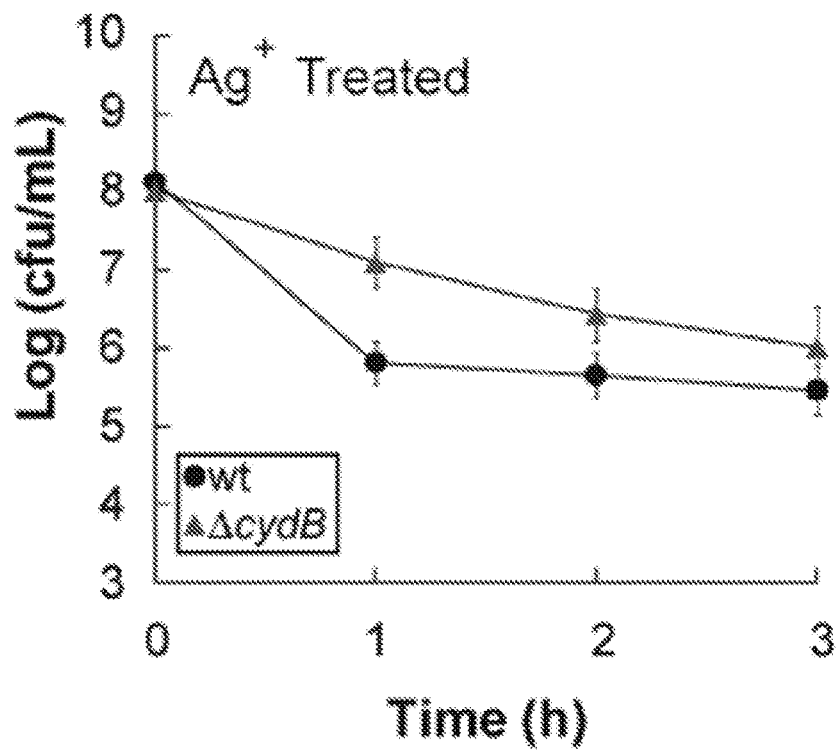
FIGS. 3A-3E show that $Ag^+$ induces OH• production through a metabolic cascade.
Figure 3B:
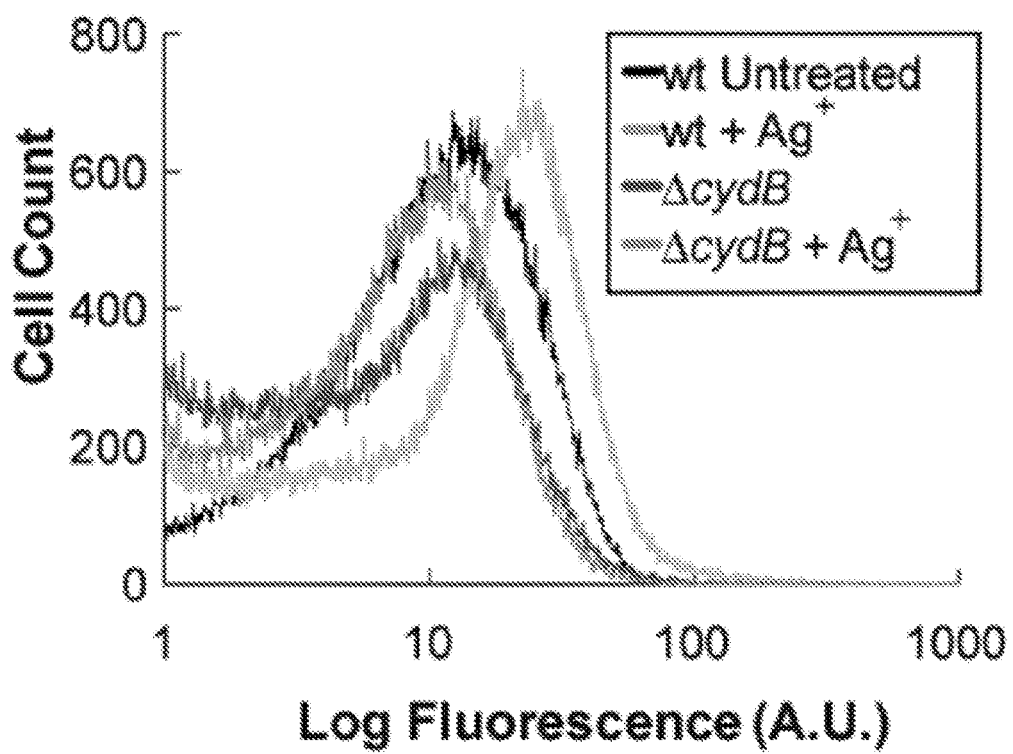
Figure 3C:
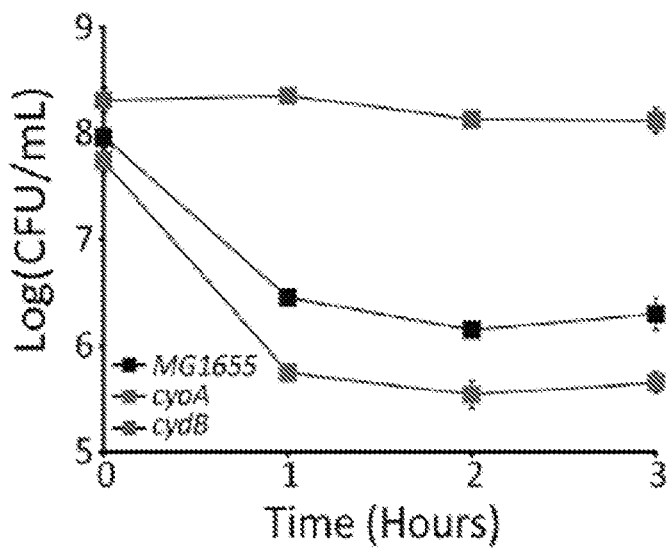

Superoxide is formed as a biochemical by-product of electron transfer through the electron transport chain (ETC); however, few of the enzymatic sources of superoxide are known [23]. The ETC component cytochrome bd-I oxidase has been previously discussed to be involved in superoxide production under conditions of stress [24]. Accordingly, it was sought to investigate whether cytochrome bd is one of the sources of $Ag^+$-mediated superoxide production. It was determined that a cytochrome bd knockout strain (ΔcydB) was less sensitive to $Ag^+$ treatment than wildtype (FIG. 3A) and exhibited lower levels of superoxide in response to the treatment (FIG. 3B), indicating that cytochrome bd can be a source of $Ag^+$-mediated superoxide production.

Figure 3D:
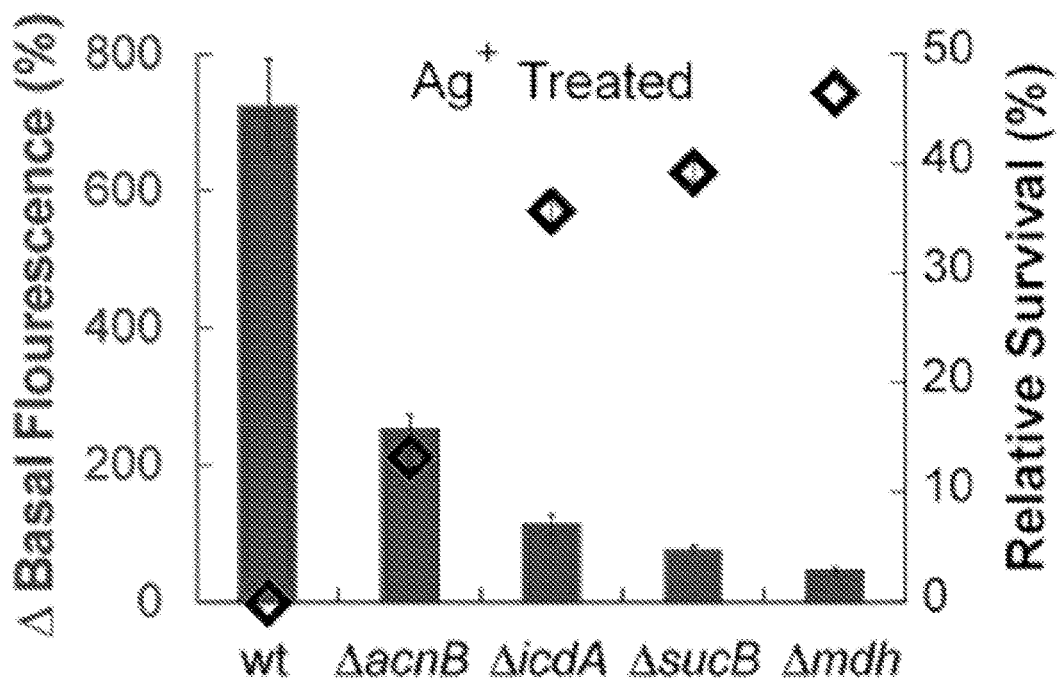
Figure 3E:
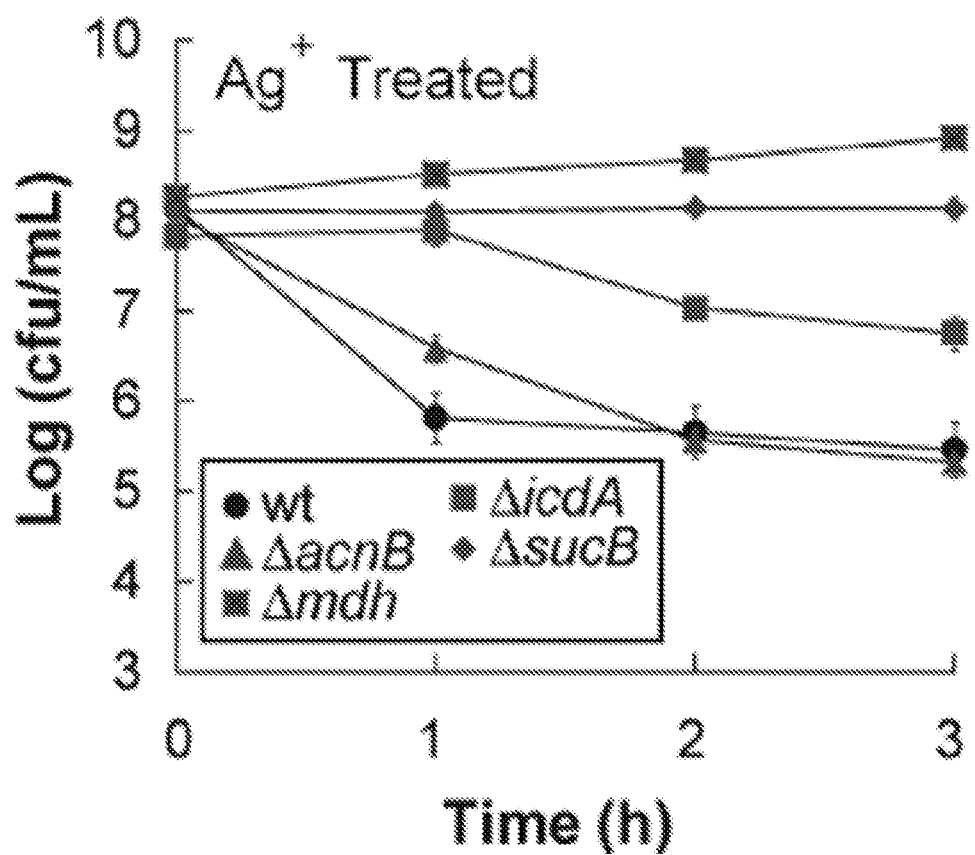

The role of the TCA cycle, a metabolic pathway that feeds the ETC, in $Ag^+$-induced cell death was also investigated. Cell viability and OH• production were examined in $Ag^+$-treated TCA cycle gene knockout strains (ΔicdA, ΔsucB, Δmdh, ΔacnB), and all the knockouts were determined to be less sensitive to $Ag^+$ treatment than wildtype (FIG. 3D). Additionally, there was a distinct correlation between the $Ag^+$-induced percent change in OH• production in the mutant strains and their susceptibility to $Ag^+$ (FIG. 3E), indicating that a functional TCA cycle can facilitate $Ag^+$-mediated OH• production. These findings indicate that $Ag^+$ can, at least partly, disrupt metabolic pathways that drive Fenton chemistry and can lead to the overproduction of OH• and cell death.

Figure 4D:
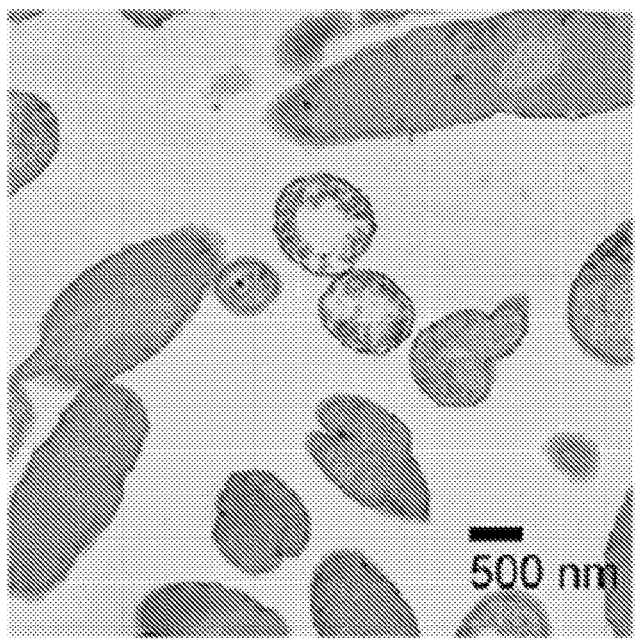
Figure 4E:
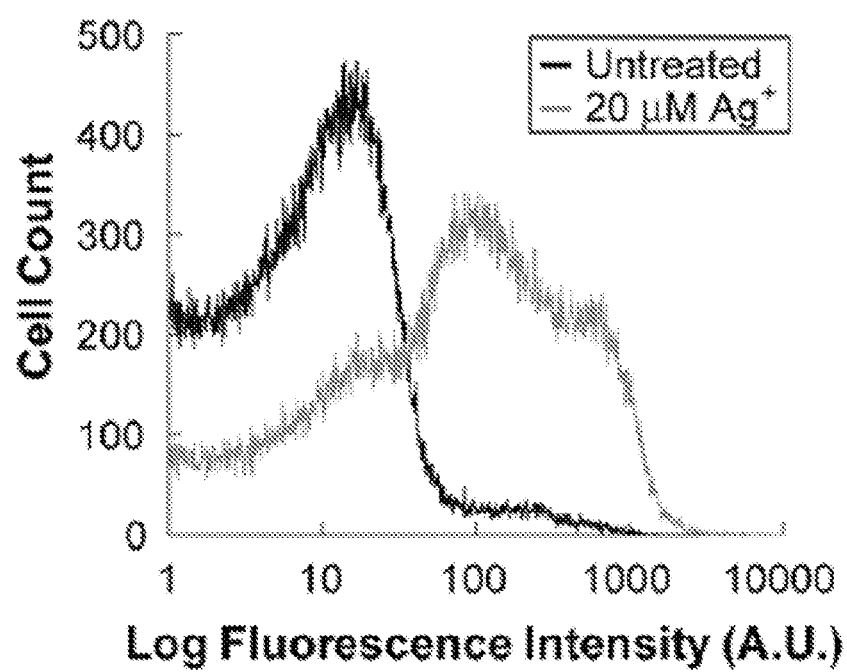
Figure 4F:
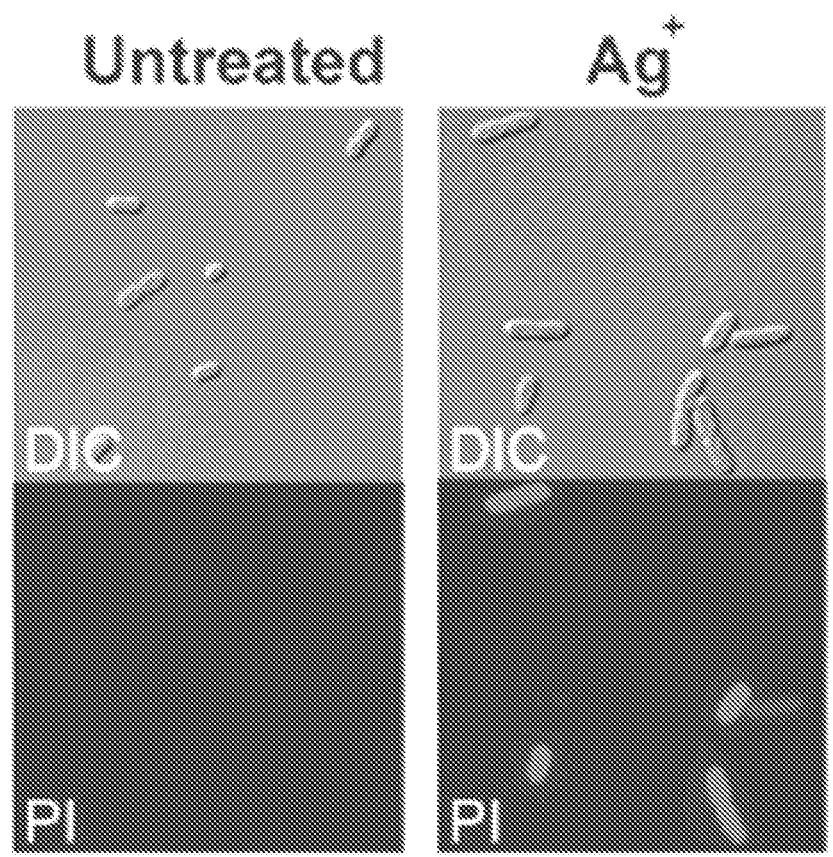

The physical changes that occur to bacterial cells as a result of $Ag^+$ treatment (FIGS. 2*a* and Supplementary 4*a-c*) were determined with transmission electron microscopy (TEM). $Ag^+$ treatment at bactericidal concentrations caused protein aggregation and drastic morphological changes in the cell envelope. Without wishing to be bound by theory, the resultant $Ag^+$-induced physical alterations in cell morphology can be, in part, indicative of an overall increase in outer membrane permeability. To assess this, propidium iodide (PI), a membrane-impermeable fluorescent dye, was used to detect permeation of the cell membrane (FIG. 4E). $Ag^+$-treated cells demonstrated significantly increased PI fluorescence relative to untreated cells, indicating destabilization of the cellular envelope and increased membrane permeability (FIG. 4F).

Figure 5A:
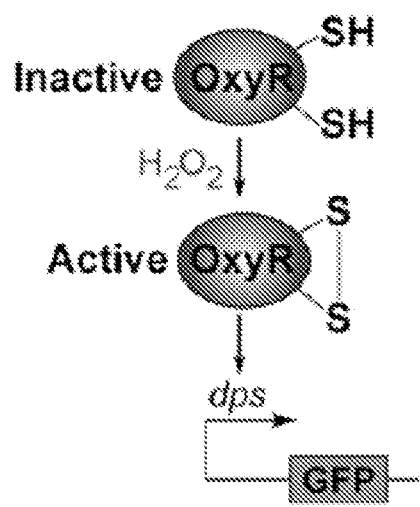
FIGS. 5A-5H show that Ag$^+$ increases membrane permeability through disruption of disulfide bond formation and secretion of misfolded proteins.
Figure 5B:
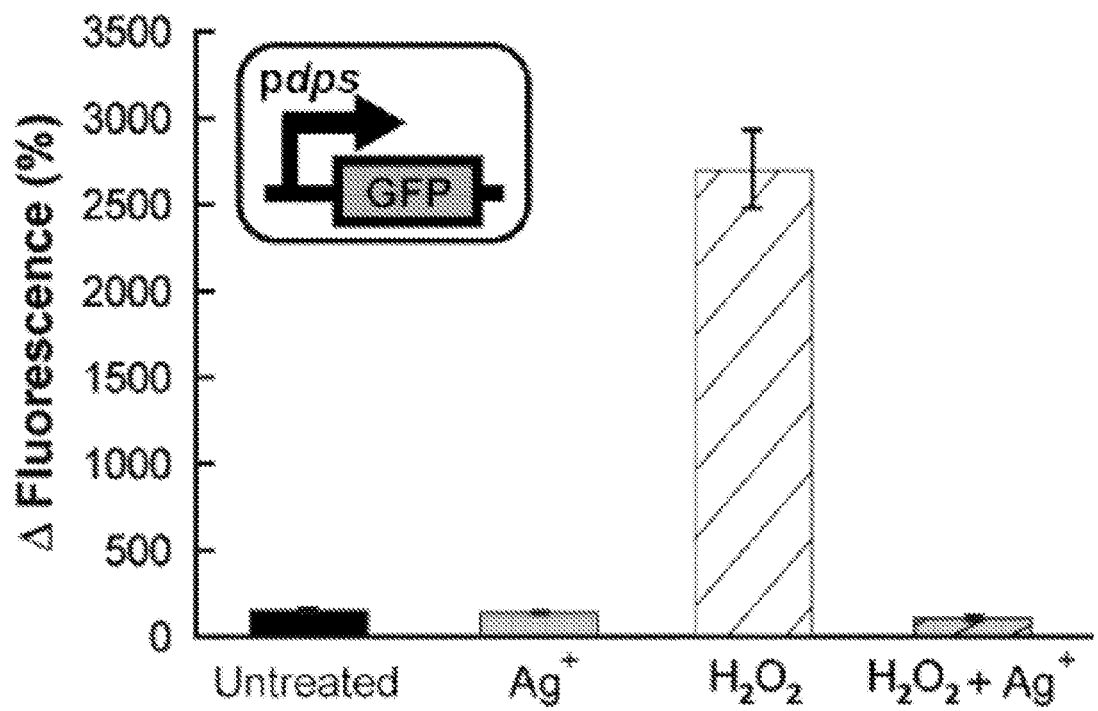

The protein aggregates observed in the TEM images of $Ag^+$-treated cells indicate the occurrence of protein misfolding. $Ag^+$ is capable of strongly interacting in vitro with sulphydryl (—SH) groups found in a variety of proteins [25]. These functional groups can form disulfide bonds in many proteins, which can contribute to their overall shape, functionality and stability. Accordingly, it was assessed whether $Ag^+$ can disrupt disulfide bond formation in vivo, which could contribute to protein misfolding and aggregation. To monitor disulfide bond formation during $Ag^+$ treatment, a dps reporter strain (FIG. 5A) that expresses GFP when the protein OxyR forms a disulfide bond in the presence of $H_2O_2$ [26] was used. The reporter strain was treated with $H_2O_2$, $Ag^+$, or a combination of both (FIG. 5B). Cells treated with $H_2O_2$ showed significantly increased fluorescence relative to untreated cells. The addition of $Ag^+$ to the $H_2O_2$ treatments reduced the fluorescence back to untreated levels, indicating that $Ag^+$ can be capable of inhibiting or disrupting protein disulfide bond formation in vivo.

Figure 5C:
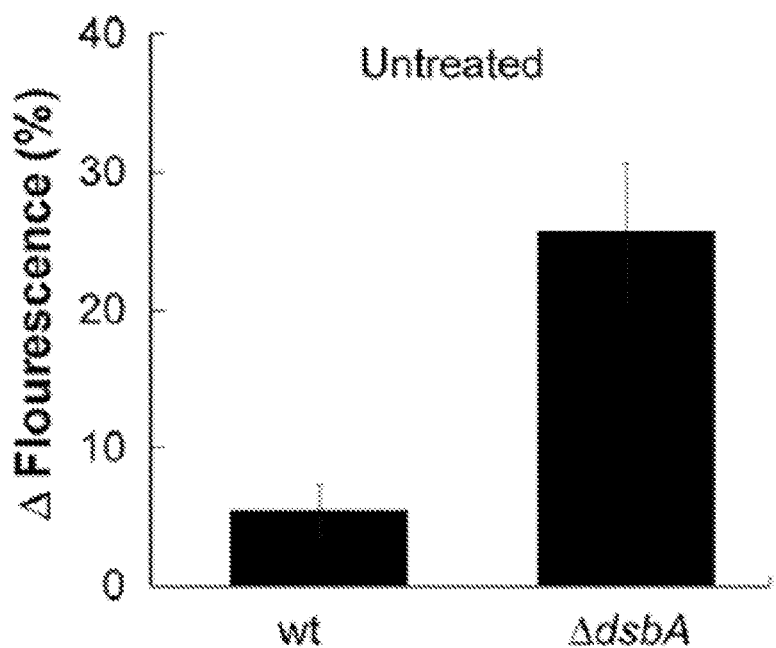

It was next assessed whether disrupting protein disulfide bond formation can affect membrane permeability. Disulfide bond formation is mediated by DsbA, a disulfide oxidoreductase. An untreated ΔdsbA strain was determined to be more permeable than an untreated wildtype strain (FIG. 5C), indicating that impairment of disulfide bond formation can be sufficient for increasing permeability. Furthermore, the effect of $Ag^+$ on the ΔdsbA strain was assessed, as the ΔdsbA strain exhibits a higher frequency of proteins with exposed sulphydryl groups [27]. It was determined that the ΔdsbA strain was more sensitive (FIG. 5D) and more permeable (FIG. 5E) than the $Ag^+$-treated wildtype strain.

Figure 5D:
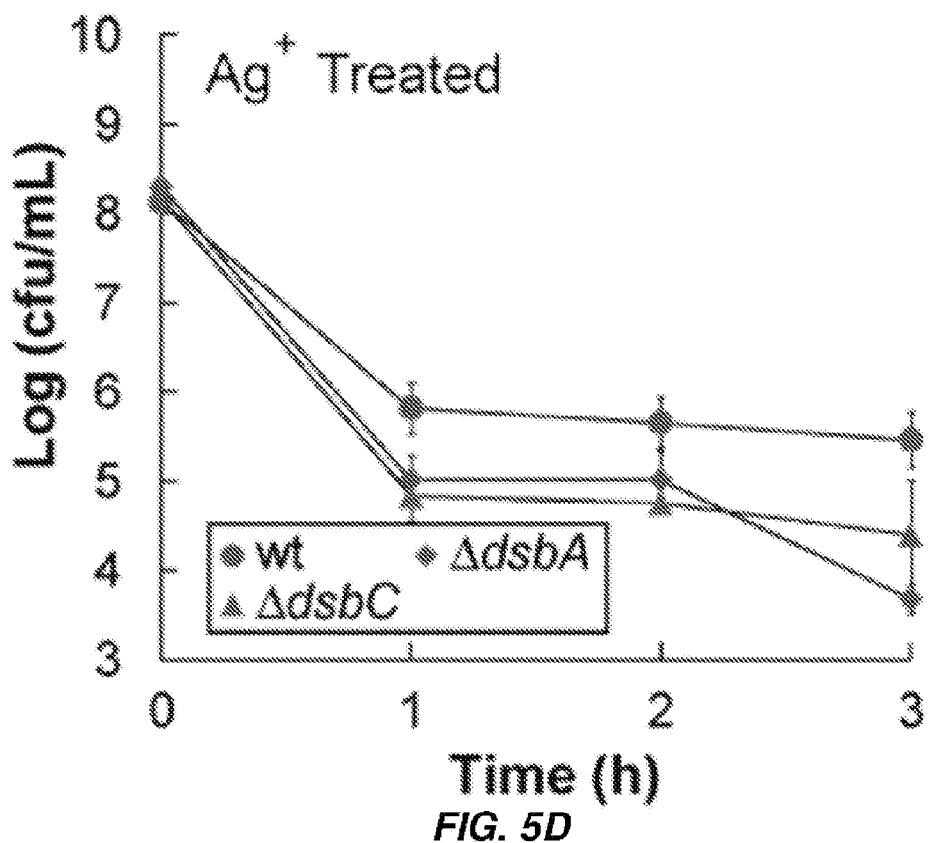
Figure 5E:
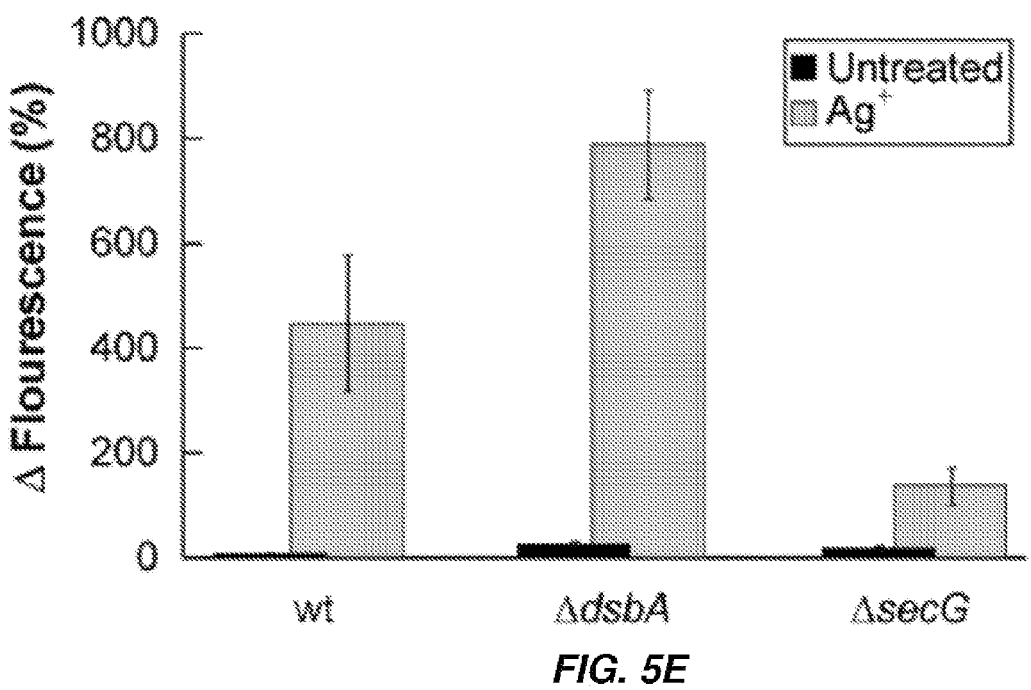

Knocking out DsbC, the enzyme responsible for disulfide bond repair, resulted in a phenotype similar to that exhibited by ΔdsbA (FIG. 5D).

Figure 5F:
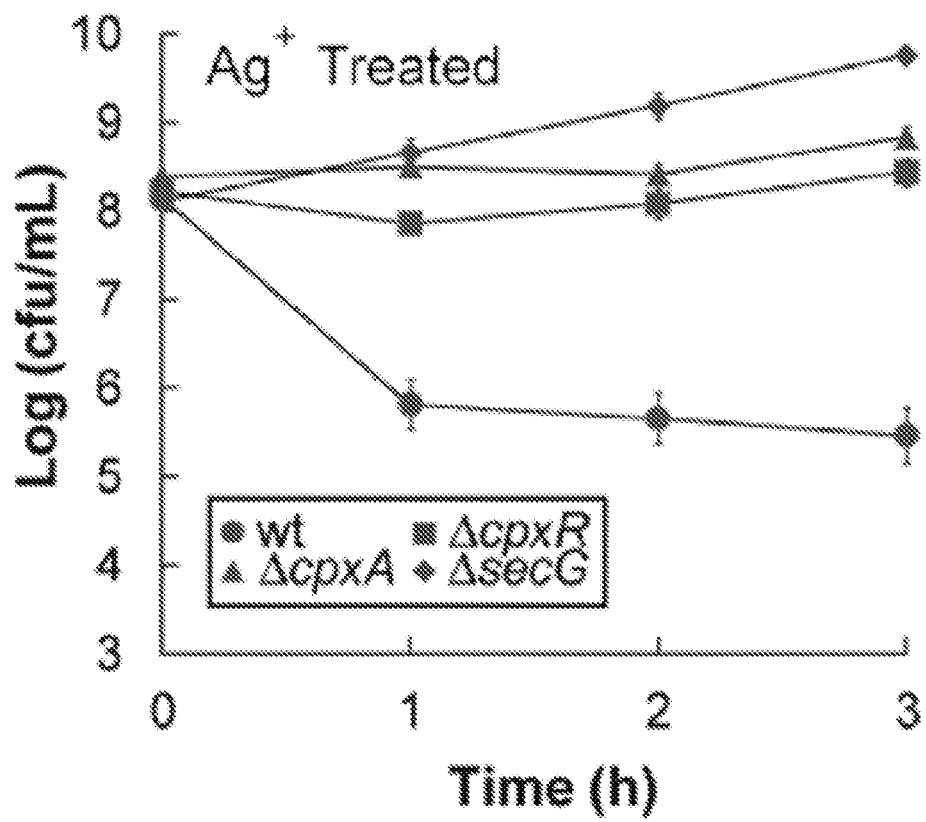

Without wishing to be bound by theory, in some embodiments, $Ag^+$-induced misfolded proteins that are secreted from the cytoplasm and transported to the outer membrane can lead to the observed membrane destabilization and increased permeability [28]. The effect of $Ag^+$ on a ΔsecG strain, which exhibits an impaired protein translocation machinery [29], was evaluated. The ΔsecG strain was less permeable (FIG. 5E) and less susceptible to $Ag^+$ treatment (FIG. 5F) compared to wildtype. These results indicate that the translocation of misfolded proteins can contribute to $Ag^+$-mediated cellular membrane permeability.

Figure 5G:
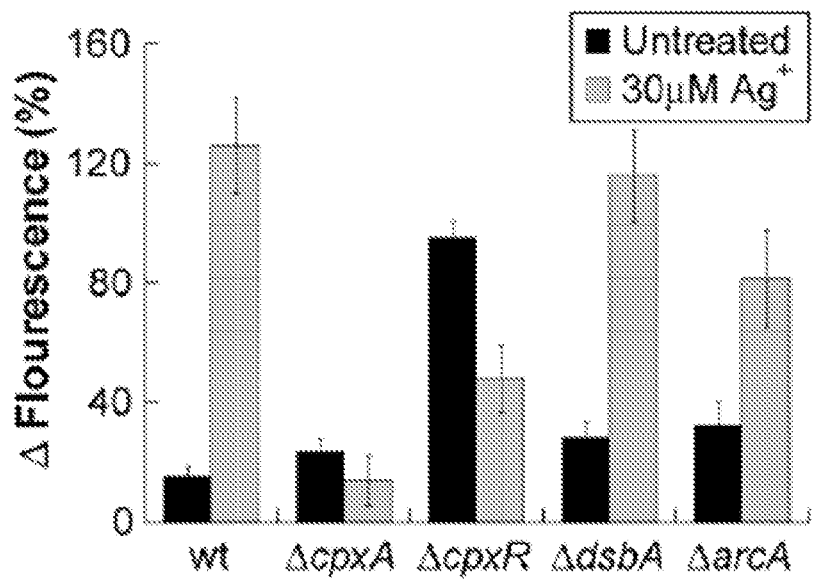
Figure 5H:
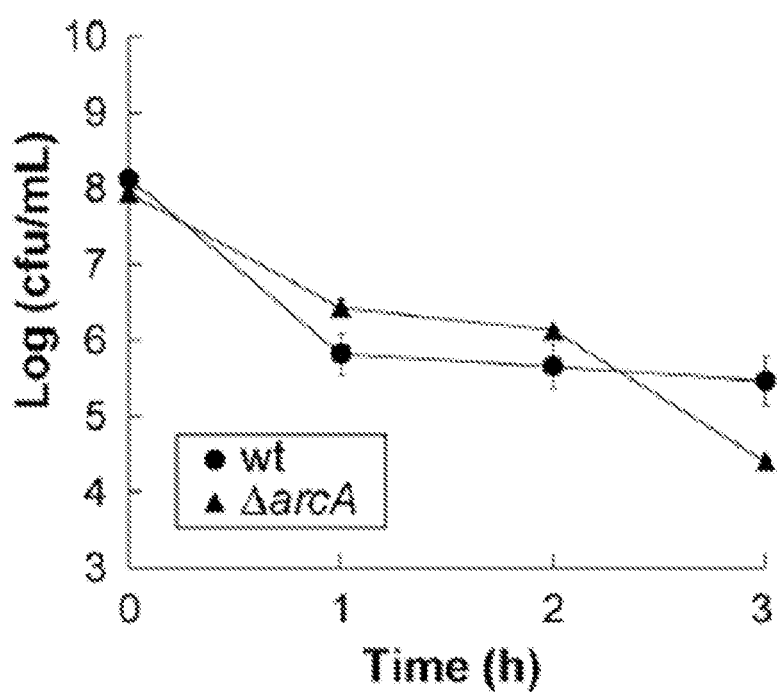

It was next sought to determine a link between the physical damage observed in the cell membrane and the biochemical cascade that leads to OH• production. The Cpx envelope stress response system monitors the fidelity of membrane integrity and can trigger metabolic changes via cross-talk with ArcA [30, 31]. ΔcpxA and ΔcpxR strains were determined herein to be less sensitive to $Ag^+$ treatment than wildtype (FIG. 5F), exhibiting bacteriostatic phenotypes. These mutants were also determined to exhibit lower levels of hydroxyl radical production in response to the treatment (FIG. 5G). These findings indicate that $Ag^+$ requires an intact Cpx signaling pathway to induce bacteria killing. Furthermore, a ΔarcA strain displayed lower hydroxyl radical production (FIG. 5G) and lower sensitivity (FIG. 5H) to $Ag^+$ treatment compared to wildtype; this finding indicates that the ArcA system can play a role in $Ag^+$-mediated cell death.

The findings presented herein indicate that $Ag^+$ targets and disrupts multiple cellular processes. In some embodiments, without wishing to be bound by theory, a multifaceted mechanism for $Ag^+$-mediated cell death can occur as follows, on the basis of theses findings. $Ag^+$ can induce protein misfolding through disruption of disulfide bonds. Translocation of these misfolded proteins across the inner membrane can lead to increases in membrane permeability and triggers stress response systems such as the Cpx regulatory network (FIG. 6A). The Cpx system can induce ETC- and TCA cycle-dependent respiratory changes through cross-talk with the ArcA system, resulting in superoxide production from cytochrome bd (FIG. 6B). The oxidative stress generated within the cell can cause leakage of $Fe^{+2}$ from internal Fe—S clusters, as does $Ag^+$ directly through disruptive interactions with Fe—S clusters; these effects together can lead to iron misregulation (FIG. 6C). These conditions can fuel Fenton chemistry that produces OH• in excessive amounts, leading to cell death (FIG. 6D).

Example 2

Figure 7D:
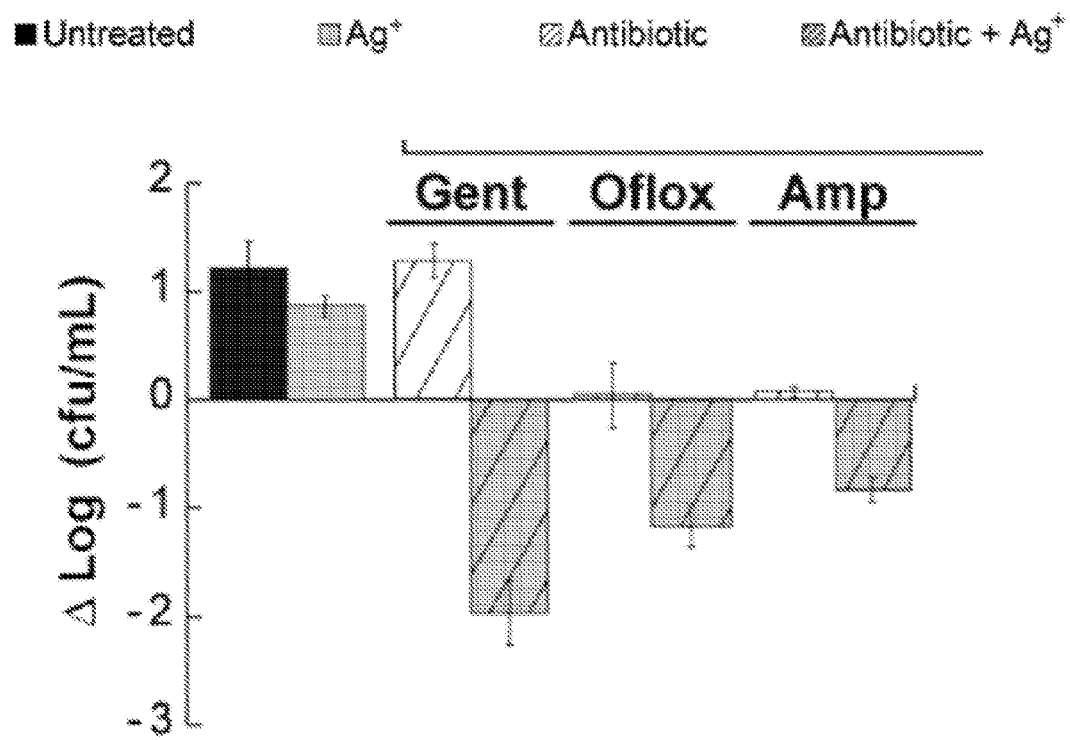
Figure 7E:
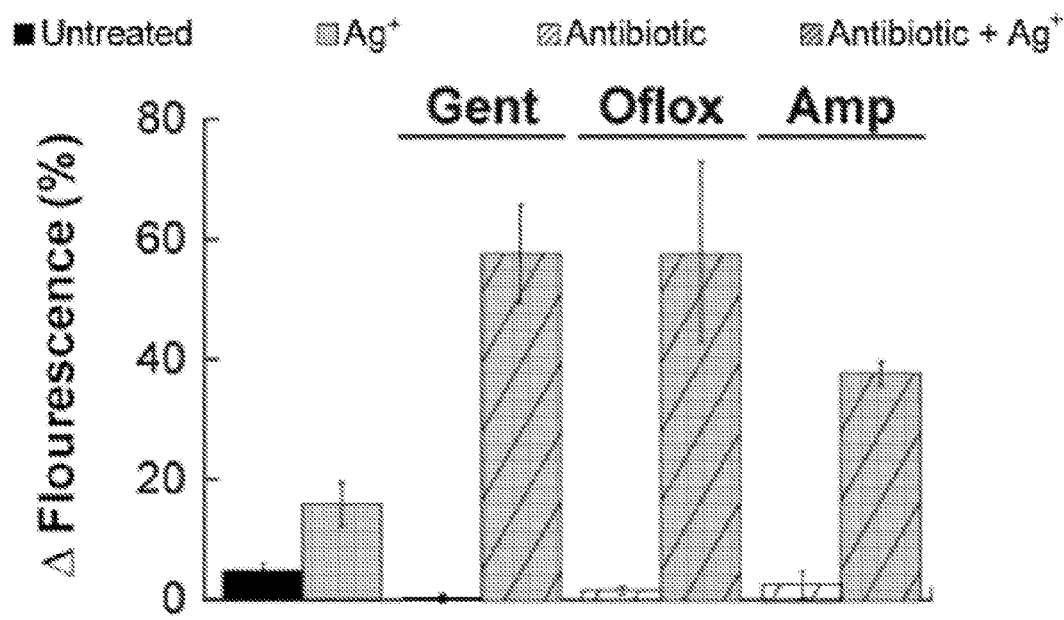

Potentiation of Antibiotic Activity Against Gram-Negative Bacteria with a Silver-Containing Compound As $Ag^+$ has been determined herein to disrupt metabolic processes as well as iron homeostasis, it was next sought to determine if these different mechanistic features of mode of action induced by $Ag^+$ could enable it to potentiate bactericidal antibiotics that, partly, share a common mechanism of action involving hydroxyl radical production [14]. To evaluate the possibility of utilizing $Ag^+$ as an antibiotic adjuvant, a model Gram-negative bacteria, *E. Coli*, was treated with low, sublethal concentrations of gentamicin (an aminoglycoside antibiotic), ampicillin (a beta-lactam antibiotic), and ofloxacin (a quinolone antibiotic). When low, sublethal concentrations of $Ag^+$ were added to these antibiotic treatments, significantly enhanced bactericidal activity was demonstrated (FIGS. 7A-7D). OH• was also measured in the treated cells and no detectable increases in ROS production was detected resulting from the sublethal antibiotic treatments (FIG. 7E). However, the addition of sublethal doses of $Ag^+$ to the antibiotic treatments induced dramatic increases in ROS, indicating that $Ag^+$ can prime cells for ROS production (FIG. 7E). Together, these findings indicate that the multifaceted ability of $Ag^+$ to stimulate Fenton chemistry (FIGS. 6A-6D) can be harnessed to potentiate antibiotics that utilize ROS as part of their bactericidal mechanism.

Figure 10A:
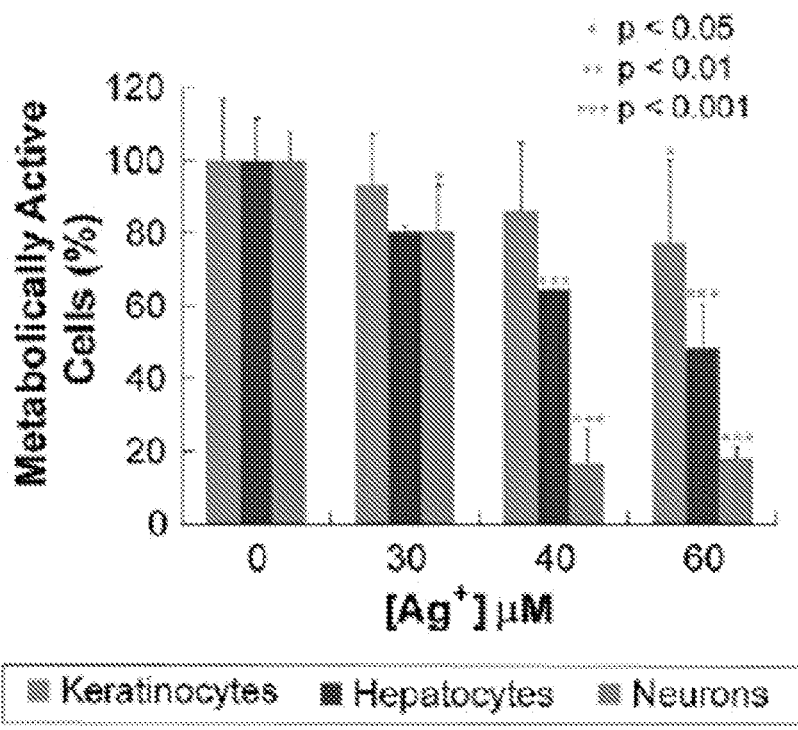
FIGS. 10A-10B show toxicity studies of Ag$^+$ showing that low levels of Ag$^+$ are not cytotoxic.
Figure 10B:
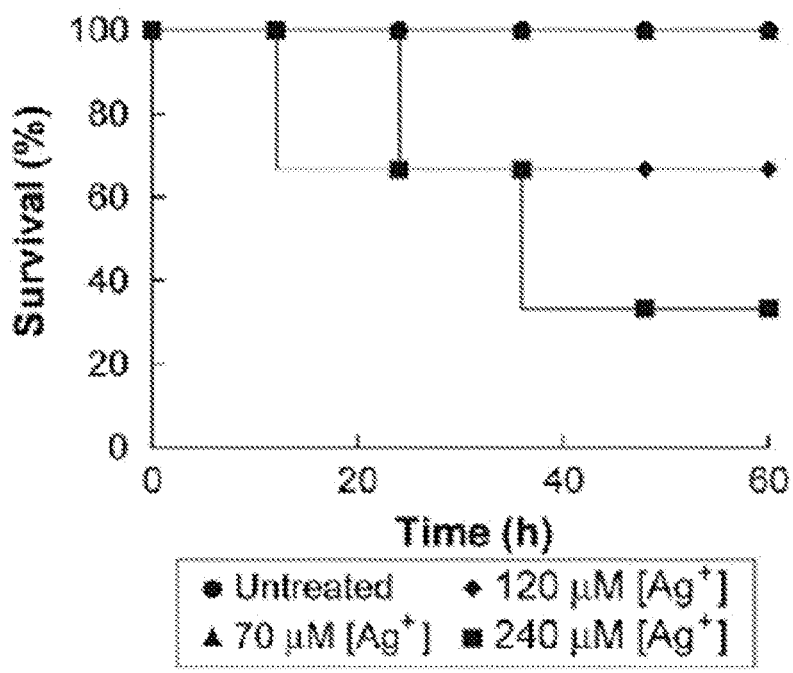

To determine clinical relevance of the use of $Ag^+$ as a therapeutic adjuvant to potentiate antibiotics, its potential toxicity was measured in vitro, in three human cell lines (primary keratinocytes, primary hepatocytes and neurons) and in vivo, in mice. $Ag^+$ showed no significant toxicity in any of the cell lines at concentrations up to 30 μM (FIG. 10A) and no effect on mice at concentrations up to 12 mg $AgNO_3$/kg (70 μM) (FIG. 10B). Given that 30 μM $Ag^+$ has significant bactericidal activity in vitro against exponentially growing *E. Coli* (FIG. 1A), in some embodiments, 30 μM $Ag^+$ was the optimal therapeutic dose to use in the animal studies. In some embodiments, a concentration of $Ag^+$ lower than 30 μM can be used as the optimal therapeutic dose to use in the animal studies.

Example 3

Figure 8E:
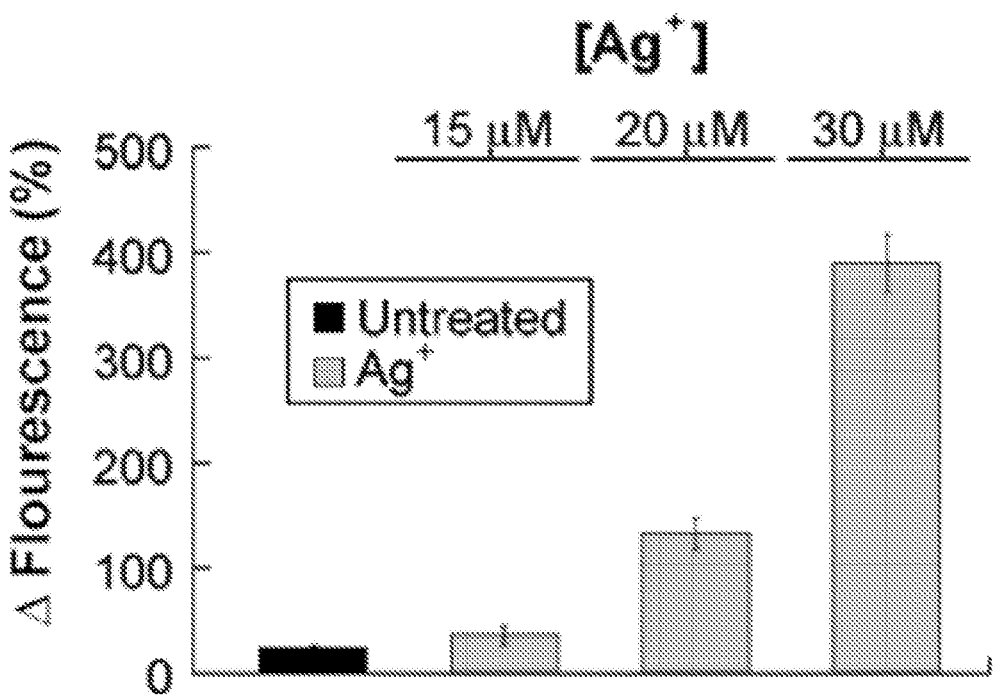

Treatment of Gram-Negative Bacterial Infection with a Gram-Positive-Specific Antibiotic in Combination with a Silver-Containing Compound Infections caused by Gram-negative bacteria are often difficult to treat [1]. These bacteria have a protective outer membrane that prevents the entry of a variety of large, bulky antibiotics, such as the glycopeptide vancomycin [11]. As shown in Example 1, treating *E. Coli* with $Ag^+$ can increase outer membrane permeability. Accordingly, it was assessed herein whether the increased outer membrane permeability induced by $Ag^+$ can be used to enable vancomycin activity against Gram-negative bacteria, thereby broadening its antibacterial spectrum and clinical utility. *E. Coli* was treated with low doses of $Ag^+$ and vancomycin individually and in combination. Surprisingly, the combination treatments resulted in significantly higher levels of cell death relative to treatments with $Ag^+$ or vancomycin alone (FIGS. 8A-8D). Moreover, the increased cell death correlated with increases in membrane permeability resulting from the application of $Ag^+$ (FIG. 8E). These results indicate that $Ag^+$ can be combined with vancomycin to form a therapeutic cocktail that, at least partly, harnesses $Ag^+$-induced permeability of the outer membrane to enable vancomycin to become effective against Gram-negative bacteria.

Figure 9:
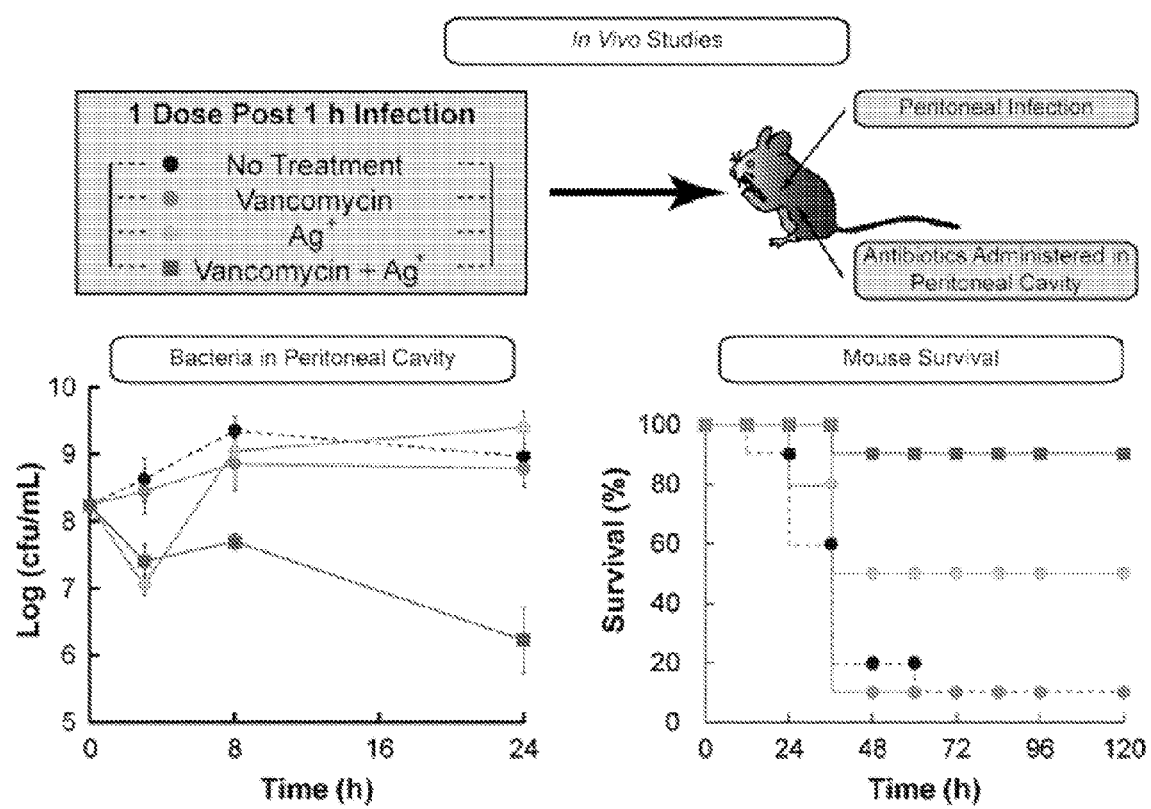
FIG. 9 shows that Ag$^+$ potentiates vancomycin antibiotics against E. Coli in vivo. The top panel shows a schematic of the in vivo mice experiments. The bottom left panel shows kill curves of wildtype E. Coli within the peritoneal cavity after treatment with: no treatment, 30 mg vancomycin/kg body weight, 6 mg AgNO$_3$/kg body weight (35 µM), and 30 mg vancomycin/kg body weight in combination with 6 mg AgNO$_3$/kg body weight. The bottom right panel shows survival of mice treated as described in the top panel. Error bars represent mean±SEM for at least 3 biological replicates. 10 mice per treatment group were used for the survival studies.

Whether $Ag^+$ could potentiate vancomycin activity in vivo was also evaluated. The effects of $Ag^+$ and vancomycin individually and in combination were analyzed in a mouse intraperitoneal infection model. The infection was induced in the peritoneal cavity of mice through the injection of $5 \times 10^6$ *E. Coli* cells suspended in a mucine aqueous solution (FIG. 9). Post-infection, the mice received either no treatment or intraperitoneal-administered treatment with vancomycin, $Ag^+$ or vancomycin plus $Ag^+$. Two aspects of the infection—the *E. Coli* cell counts within the peritoneal cavity and mouse survival—were monitored. Treatment with vancomycin or Ag$^+$ alone resulted in no effect on peritoneal *E. Coli* cell counts after 24 hours, whereas treatment with vancomycin plus Ag$^+$ reduced the cell counts by 100-fold (FIG. 9). Additionally, 90% of mice treated with the vancomycin-plus-Ag$^+$ combination survived (after 5 days), compared with 50% of mice treated with Ag$^+$ alone and 10% of mice treated with vancomycin alone or just the vehicle (FIG. 9). These in vivo findings demonstrate the clinical efficacy of using Ag$^+$ to enable the activity of vancomycin against Gram-negative pathogens.

Presented herein is the capability of Ag$^+$, an ancient antibacterial agent, to disrupt multiple bacterial cellular networks and processes, resulting in the destabilization of the cellular envelope and the production of ROS. Without wishing to be bound by theory, these mechanistic effects can be used to potentiate a broad range of antibiotics, thus establishing Ag$^+$ as a potent adjuvant therapy. The ability of Ag$^+$ to permeabilize the outer membranes of Gram-negative bacteria, in particular embodiments, can turn out to be a new weapon in the current antibacterial arsenal. Multidrug-resistant Gram-negative bacteria are an important cause of nosocomial infections, and provided herein are combination therapies for treatment of Gram-negative bacterial infection involving Ag$^+$ and large antibiotics such as vancomycin or any antibiotics specific for Gram-positive bacteria.

Exemplary materials and methods

Antibiotics and chemicals: All experiments presented herein were performed in Luria Bertani (LB) medium (Fisher Scientific). Exemplary concentrations that were used for the antibacterial experiments with *E. Coli* are shown as follows: 10 µM, 20 µM or 30 µM silver nitrate (Fisher Scientific), 1 µg/mL ampicillin (Fisher Scientific), 0.25 µg/mL gentamicin (Fisher), 0.03 µg/mL ofloxacin (Sigma), and 30 µg/mL vancomycin (MP Pharmaceuticals). Additional chemicals that were used in the Examples include: phosphate buffer saline (PBS) (Sigma), Tris/HCl buffer pH 7.5 (Sigma), ferene-S(Fisher Scientific), 3'-p-hydroxyphenyl fluorescein dye (Invitrogen), propidium iodide (Invitrogen), and thiourea (Fluka).

Media and growth conditions: The growth and survival of untreated exponential-phase *E. coli* strains were compared with the antibiotic-treated strains. Briefly, cultures from frozen stock were grown overnight. The overnight culture was diluted 1:250 with 25 mL of LB medium in 250 mL flasks and incubated at 37° C., 300 rpm, and 80% humidity. Cells were then grown until an OD$_{600\ nm}$ of 0.3. For antibiotic treatments, 500 µL samples were taken from the flasks and transferred to a 24-well plate incubated at 37° C., 900 rpms, and 80% humidity. For the hydroxyl radical (OH•) quenching experiments, thiourea (150 mM) was added simultaneously with the silver salt (e.g., AgNO$_3$). Measurements of OD$_{600\ nm}$ were taken using a SpectraFluor Plus (Tecan). For measuring the colony forming unit (cfu) per milliliter (mL), 100 µL of culture was collected and then serially diluted in PBS (pH 7.2). A 5 µL portion of each dilution was plated in LB-agar plates and incubated overnight at 37° C. The colonies were counted and cfu/mL was calculated using the following formula:

((number of colonies)*(dilution factor))/(amount plated).

Strains: All *E. Coli* experiments were performed with MG1655 (ATCC 700926)-derived strains. The knockouts were constructed using P1 phage transduction and derived from the Keio single-gene knockout collection [32].

Removal of the kanamycin resistance cassette was accomplished using the pcp20 plasmid and confirmed by PCR prior to experimentation.

Transmission electron microscopy: Samples analyzed with transmission electron microscopy were prepared using the following procedure: 100 µL samples were taken, centrifuged and resuspended in 1×PBS twice. To fix the bacterial cells, the samples were centrifuged and resuspended in 1 mL of 2.5% glutaraldehyde solution in PBS for 30 min. The cells were then dehydrated by exposing them for 10 min to a series of ethanol concentration solutions (50, 60, 80, 90 and 100% ethanol/PBS solutions). The cells were finally embedded into Spurr resin and left to polymerize in an oven at 60° C. for 24 h. The polymerized samples were sectioned into slices of thickness of ~60 nm using a microtome. The sliced samples were analyzed in a Jeol 1200EX-80 kV.

Iron detection Ferene S colorimetric assay: The release of protein-bound iron in an *E. Coli* cell lysate was measured using a Ferene-S assay. The lysate was prepared by first growing 150 mL of cells to an OD$_{600\ nm}$ of 0.7. The cells were then lysed by sonication in 20 mM Tris/HCl pH 7.2 buffer. The samples were centrifuged and the supernatants containing the cell lysates were collected. Lysates were treated either with heat (90° C. for 20 min) or with 30 µM AgNO$_3$ (for 1 hr). 10 mM Ferene-S was added to each sample and samples were then incubated at room temperature for 1 h. Absorbance at 593 nm was then measured.

Iron misregulation superoxide production and disulfide bond formation measurements: Iron regulation and superoxide production were measured using previously constructed genetic reporter strains [18]. A disulfide bond formation sensor was constructed based on activation of the OxyR protein, which forms a disulfide bond in the presence of H$_2$O$_2$. The disulfide bond formation sensor was constructed by PCR-amplifying the native dps promoter and cloning it into the BamHI and XhoI restriction sites of the pZE21 vector [33]. The forward primer for PCR was GCGCCTCGAGCCGCTTCAATGGGGTCTACGCT (SEQ ID NO: 1), and the reverse primer was GGCCGGATCCTCGGAGACATCGTTGCGGGTAT (SEQ ID NO: 2). The data were collected using a Becton Dickinson FACSCalibur flow cytometer with a 488-nm argon laser and a 515-545 nm emission filter (FL1) at high flow rate. Calibrite beads (Becton Dickinson) were used for instrument calibration. FlowJo was used to process flow cytometric data.

OH• production measurements: The fluorescent reporter dye, for example, 3'-(p-hydroxyphenyl fluorescein (HPF), which is oxidized by hydroxyl radicals with high specificity, was used for radical detection. Overnight cultures were diluted 1:250 with 25 mL of LB medium in 250 mL flasks and incubated at 37° C., 300 rpms, and 80% humidity. Cells were grown until reaching an OD$_{600\ nm}$~0.3. 500 µL samples were taken from the flasks and transferred to a 24-well plate for treatments. After 1 h of treatment, 100 µL samples were collected, centrifuged at 10,000 rpm, and the media was removed and replaced with PBS containing 5 mM HPF. Samples were incubated in the dark at room temperature for 15 min and then centrifuged at 10,000 rpm. The supernatant was removed and replaced with 1×PBS for flow cytometry measurements. The fluorescence data were collected using the FL1 filter of the Becton Dickinson FACSCalibur flow cytometer described previously. The following equation was used to determine percentage change in fluorescence of the dye (e.g., HPF) due to increase in cell permeability:

$$((|\text{Fluorescence}_{HPF} - \text{Fluorescence}_{no\ HPF}|)/(\text{Fluorescence}_{no\ HPF}))*(100).$$

These values were compared with the same formula between treated and non-treated samples to obtain a percent change. FlowJo was used to process flow cytometric data.

Membrane permeability measurements: The fluorescent reporter dye, for example, propidium iodide (PI), was used to monitor membrane permeability. Increased PI fluorescence is correlated with increased membrane permeability [34, 35]. Overnight cultures were diluted 1:250 with 25 mL of LB medium in 250 mL flasks and incubated at 37° C., 300 rpms and 80% humidity. Cells were grown until reaching an $OD_{600\ nm}$~0.3. 500 µL samples were taken from the flasks and transferred to a 24-well plate for treatments. After 1 hour of treatment, 100 µL samples were collected, centrifuged at 10,000 rpm, and the media was removed and replaced with PBS containing 1 mM PI. Samples were incubated in the dark at room temperature for 15 min and then centrifuged at 10,000 rpm. The supernatant was removed and replaced with 1×PBS for flow cytometry measurements. The fluorescence data were collected using the FL2 filter of the Becton Dickinson FACSCalibur flow cytometer described previously. The following equation was used to determine percentage change in fluorescence of the dye (e.g., PI) due to increase in cell permeability:

$$((|Fluorescence_{PI} - Fluorescence_{no\ PI}|)/(Fluorescence_{no\ PI}))*(100).$$

These values were compared with the same formula between treated and non-treated samples to obtain a percent change. FlowJo was used to process flow cytometric data.

Peritoneal mouse infection model

Minimum lethal dose (MLD) of *E. coli* for peritonitis mouse model: For all animal experiments, 6-week-old C57BL6 male mice (body weight, ~20 g) were used. Serial dilutions of *E. Coli* ranging from $1×10^6$-$1×10^9$ cfu/mouse were introduced into the peritoneal cavity of the mice in 500 µL aliquots of sterile saline supplemented with 8% mucine. The animals were observed for seven days. The MLD was determined to be $5×10^6$ cfu/mouse by measuring the lowest concentration of *E. Coli* that killed 100% of the recipient mice.

Mouse Peritonitis Model: Inbred, wildtype male C57BL/6 mice (6 weeks; ~20 g) were used. After one week of quarantine, inoculation was performed by intraperitoneal (i.p.) injection of 500 µL of the MLD *E. Coli* inoculum using a 26-gauge syringe. The inoculum was delivered in suspension with 8% (w/v) mucine in sterile saline. 1 h after introduction of the inoculum, the untreated control group (t=0) was euthanized. Subsequently, antibacterial therapy was initiated by intraperitoneal injection. Ten mice per group received antibacterial treatments. At time 0 (control only), 8, 16 and 24 h, mice were euthanized. Peritoneal washes were performed by injecting 1.0 mL of sterile saline in the intraperitoneal followed by a massage of the abdomen. Subsequently, the abdomen was opened and 200 µL of peritoneal fluid (PF) was recovered from the peritoneum for analysis of *E. Coli* cfu/mL.

Survival Assays: Male C57BL6 6-week old mice (weighing ~20 g) received intraperitoneal injections of the MLD of *E. Coli* in a volume of 500 µL with 8% mucine. After 1 h, ten mice per group received either vehicle (PBS) only or infusions of the antibacterial treatments. The mice were observed for 5 days to evaluate survival.

Tissue Culture

Exemplary cells: Primary human keratinocytes were obtained from neonatal foreskins as described previously [36]. Briefly, neonatal foreskins were trypsinized overnight at 4° C. The keratinocytes were maintained in a serum-free basal medium made of MCDB-153 plus the following amino acids: L-tryptophan (60 µM), L-tyrosine (90 µM), L-phenylalanine (120 µM), L-methionine (120 µM), L-isoleucine (770 µM), and L-histidine (320 µM). The basal medium was further supplemented with 0.15 mM calcium, 3 µg/mL bovine pituitary extract, 25 ng/mL EGF and 5 µg/mL prostaglandin E1, to make complete medium. For initial plating of cells, complete medium was supplemented with 0.1 µg/mL cholera toxin and 200 ng/mL of hydrocortisone. Cells were fed with complete medium three times per week and passaged using trypsin/EDTA.

SH-SY5Y human neuroblastoma cell line (Lonza) was cultured in DMEM/F12 plus 10% FBS. Cells were fed three times per week and passaged using trypsin/EDTA.

Human primary hepatocytes (CryoHepatocytes, BD Biosciences) were prepared using the Cryopreserved Hepatocyte Purification Kit: Two Steps (BD Bioscience) per the manufacturer's instruction. The cells were plated at a concentration of $4×10^5$ cells per well in 24-well plates coated with rat tail collagen I (BD Biosciences). Cells were fed with HepatoSTIM media (BD Biosciences) three times per week.

MTT Assay: Mitochondrial dehydrogenase enzyme activity is used as a proxy for metabolic activity. The assay tests the ability of cells to enzymatically convert 3-(4,5-Dimethyl-2-thiazolyl)-2,5-diphenyl-2H-tetrazolium (MTT) to formazan. Formazan is an insoluble colorimetric indicator that can be detected by measuring absorbance at 570 nm. All three cell types were seeded in 24-well plates at a concentration of $4×10^4$ cells per well. SH-SY5Y cells were differentiated using 10 µM retinoic acid for 72 h prior to $AgNO_3$ treatment. Hepatocytes were plated on collagen I and incubated with HepatoSTIM (BD Biosciences) 24 h prior to $AgNO_3$ treatment to induce differentiation.

Primary human keratinocytes, differentiated SH-SY5Y human neuronal cells and differentiated primary human hepatocytes were treated with vehicle alone or 30 µM, 40 µM, 60 µM $AgNO_3$. 24 h after treatment, MTT assay was performed. MTT was prepared at a concentration of 1 mg/mL in PBS. Media was aspirated out of each well and replaced with 400 µL of the MTT solution plus 1600 µL of DMEM without phenol red. The MTT-treated cells were incubated for 4 h at 37° C., 5% $CO_2$. MTT was removed from each well and replaced with 800 µL DMSO plus 200 µL of Sorenson's glycine buffer (0.1 M glycine, 0.1 M NaCl, pH 10.5). The plates were incubated at room temperature for 5 min. Absorbance was measured at 570 nm, with a reference wavelength of 630 nm to quantify the amount of formazan produced by the metabolically active cells.

REFERENCES

1. Li, J. et al. Colistin: the re-emerging antibiotic for multidrug-resistant Gram-negative bacterial infections. Lancet Infectious Diseases 6, 589-601 (2006).
2. Taubes, G. The bacteria fight back. Science 321, 356-361 (2008).
3. Morones, J. R. et al. The bactericidal effect of silver nanoparticles. Nanotechnology 16, 2346-2353 (2005).
4. Thurman, R. B. & Gerba, C. P. The molecular mechanisms of copper and silver ion disinfection of bacteria and viruses. CRC Critical Reviews in Environmental Control 18, 295-315 (1988).
5. Feng, Q. L. et al. A mechanistic study of the antibacterial effect of silver ions on *Escherichia coli* and *Staphylococcus aureus*. Journal of Biomedical Materials Research 52, 662-668 (2000).

6. Jung, W. K. et al. Antibacterial activity and mechanism of action of the silver ion in *Staphylococcus aureus* and *Escherichia coli*. Applied and Environmental Microbiology 74, 2171-2178 (2008).
7. Slawson, R. M., Lee, H. & Trevors, J. T. Bacterial Interactions with Silver. Biology of Metals 3, 151-154 (1990).
8. Holt, K. B. & Bard, A. J. Interaction of silver(I) ions with the respiratory chain of *Escherichia coli*: An electrochemical and scanning electrochemical microscopy study of the antimicrobial mechanism of micromolar Ag. Biochemistry 44, 13214-13223 (2005).
9. Park, H. J. et al. Silver-ion-mediated reactive oxygen species generation affecting bactericidal activity. Water Research 43, 1027-1032 (2009).
10. Gordon, O. et al. Silver coordination polymers for prevention of implant infection: Thiol interaction, impact on respiratory chain enzymes, and hydroxyl radical induction. Antimicrobial Agents and Chemotherapy 54, 4208-4218.
11. Pages, J. M., James, C. E. & Winterhalter, M. The porin and the permeating antibiotic: a selective diffusion barrier in Gram-negative bacteria. Nature Reviews Microbiology 6, 893-903 (2008).
12. Magner, L. N. Hippocrates and the Hippocratic Tradition. A History of Medicine (ed. Duffy, J.) (Marcel Dekker, Inc, NYC, 1992).
13. Kohanski, M. A., Dwyer, D. J. & Collins, J. J. How antibiotics kill bacteria: from targets to networks. Nature Reviews Microbiology 8, 423-435 (2010).
14. Kohanski, M. A., Dwyer, D. J., Hayete, B., Lawrence, C. A. & Collins, J. J. A common mechanism of cellular death induced by bactericidal antibiotics. Cell 130, 797-810 (2007).
15. Setsukinai, K., Urano, Y., Kakinuma, K., Majima, H. J. & Nagano, T. Development of novel fluorescence probes that can reliably detect reactive oxygen species and distinguish specific species. Journal of Biological Chemistry 278, 3170-3175 (2003).
16. Novogrodsky, A., Ravid, A., Rubin, A. L. & Stenzel, K. H. Hydroxyl radical scavengers inhibit lymphocyte mitogenesis. Proceedings of the National Academy of Sciences of the United States of America-Biological Sciences 79, 1171-1174 (1982).
17. Imlay, J. A., Chin, S. M. & Linn, S. Toxic DNA damage by hydrogen peroxide through the Fenton reaction in vivo and in vitro. Science 240, 640-642 (1988).
18. Dwyer, D. J., Kohanski, M. A., Hayete, B. & Collins, J. J. Gyrase inhibitors induce an oxidative damage cellular death pathway in *Escherichia coli*. Molecular Systems Biology 3 (2007).
19. Touati, D., Jacques, M., Tardat, B., Bouchard, L. & Despied, S. Lethal oxidative damage and mutagenesis are generated by iron in delta fur mutants of *Escherichia coli*: protective role of superoxide dismutase. Journal of Bacteriology 177, 2305-2314 (1995).
20. Schwartz, C. J., Djaman, O., Imlay, J. A. & Kiley, P. J. The cysteine desulfurase, IscS, has a major role in in vivo Fe—S cluster formation in *Escherichia coli*. Proceedings of the National Academy of Sciences of the United States of America 97, 9009-9014 (2000).
21. Chillappagari, S. et al. Copper stress affects iron homeostasis by destabilizing iron-sulfur cluster formation in *Bacillus subtilis*. Journal of Bacteriology 192, 2512-2524.
22. Eskelinen, S., Haikonen, M. & Raisanen, S. Ferene-S as the chromagen for serum determinations. Scandinavian Journal of Clinical & Laboratory Investigation 43, 453-455 (1983).
23. Korshunov, S. & Imlay, J. A. Two sources of endogenous hydrogen peroxide in *Escherichia coli*. Molecular Microbiology 75, 1389-1401.
24. Lindqvist, A., Membrillo-Hernandez, J., Poole, R. K. & Cook, G. M. Roles of respiratory oxidases in protecting *Escherichia coli* K12 from oxidative stress. Antonie Van Leeuwenhoek International Journal of General and Molecular Microbiology 78, 23-31 (2000).
25. Liau, S. Y., Read, D. C., Pugh, W. J., Furr, J. R. & Russell, A. D. Interaction of silver nitrate with readily identifiable groups: Relationship to the antibacterial action of silver ions. Letters in Applied Microbiology 25, 279-283 (1997).
26. Zheng, M., Aslund, F. & Storz, G. Activation of the OxyR transcription factor by reversible disulfide bond formation. Science 279, 1718-1721 (1998).
27. Kadokura, H., Katzen, F. & Beckwith, J. Protein disulfide bond formation in prokaryotes. Annual Review of Biochemistry 72, 111-135 (2003).
28. Denoncin, K., Vertommen, D., Paek, E. & Collet, J. F. The protein-disulfide isomerase DsbC cooperates with SurA and DsbA in the assembly of the essential b-barrel protein LptD. Journal of Biological Chemistry 285, 29425-29433.
29. Matsumoto, G., Mori, H. & Ito, K. Roles of SecG in ATP- and SecA-dependent protein translocation. Proceedings of the National Academy of Sciences of the United States of America 95, 13567-13572 (1998).
30. Cotter, P. A., Melville, S. B., Albrecht, J. A. & Gunsalus, R. P. Aerobic regulation of cytochrome d oxidase (cydAB) operon expression in *Escherichia coli*: Roles of Fnr and ArcA in repression and activation. Molecular Microbiology 25, 605-615 (1997).
31. Kohanski, M. A., Dwyer, D. J., Wierzbowski, J., Cottarel, G. & Collins, J. J. Mistranslation of Membrane Proteins and Two-Component System Activation Trigger Antibiotic-Mediated Cell Death. Cell 135, 679-690 (2008).
32. Baba, T. et al. Construction of *Escherichia coli* K-12 in-frame, single-gene knockout mutants: the Keio collection. Molecular Systems Biology 2 (2006).
33. Lutz, R. & Bujard, H. Independent and tight regulation of transcriptional units in *Escherichia coli* via the LacR/O, the TetR/O and AraC/I-1-I-2 regulatory elements. Nucleic Acids Research 25, 1203-1210 (1997).
34. Hiraoka, Y. & Kimbara, K. Rapid assessment of the physiological status of the polychlorinated biphenyl degrader *Comamonas testosteroni* TK102 by flow cytometry. Applied and Environmental Microbiology 68, 2031-2035 (2002).
35. Novo, D. J., Perlmutter, N. G., Hunt, R. H. & Shapiro, H. M. Multiparameter flow cytometric analysis of antibiotic effects on membrane potential, membrane permeability, and bacterial counts of *Staphylococcus aureus* and *Micrococcus luteus*. Antimicrobial Agents and Chemotherapy 44, 827-834 (2000).
36. Chen, T. C., Persons, K., Liu, W. W., Chen, M. L. & Holick, M. F. The antiproliferative and differentiative activities of 1,25-dihydroxyvitamin D-3 are potentiated by epidermal growth-factor and attenuated by insulin in cultured human keratinocytes. Journal of Investigative Dermatology 104, 113-117 (1995).

SEQUENCE LISTING (SEQ ID NO: 1)
GCGCCTCGAGCCGCTTCAATGGGGTCTACGCT (SEQ ID NO: 2)
GGCCGGATCCTCGGAGACATCGTTGCGGGTAT.

It is understood that the foregoing detailed description and examples are illustrative only and are not to be taken as limitations upon the scope of the invention. Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

SEQUENCE LISTING

```
<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gcgcctcgag ccgcttcaat ggggtctacg ct                                   32

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ggccggatcc tcggagacat cgttgcgggt at                                   32
``` potentiating amount of a silver-containing compound, wherein the potentiating amount of the silver-containing compound is sufficient to expand the spectrum of the antibiotic and to induce production of endogenous ROS in the microbe, but is below a threshold level required to effectively treat the Gram-negative microbial infection when used alone.

2. The method of claim 1, wherein the antibiotic is an antibiotic that does not penetrate through an outer membrane of the Gram-negative microbe, or is an antibiotic that treats a Gram-positive microbial infection.

3. The method of claim 2, wherein the antibiotic that treats the Gram-positive microbial infection is vancomycin, teicoplanin, moenomycin, dicloxacillin, daptomycin, linezolid, oxacillin, nafcillin, or a combination thereof.

4. The method of claim 3, wherein the antibiotic is daptomycin.

5. The method of claim 4, wherein the daptomycin and the silver-containing compound are administered intravenously.

6. The method of claim 5, wherein the daptomycin is administered at less than 4 mg/kg.

7. The method of claim 4, wherein the daptomycin and the silver-containing compound are administered separately.

8. The method of claim 3, wherein the silver-containing compound is selected from the group consisting of silver nitrate, silver acetate, silver benzoate, silver carbonate, silver iodate, silver iodide, silver lactate, silver laurate, silver oxide, silver palmitate, silver sulfadiazine, and any combinations thereof.

What is claimed is:

1. A method for treating an individual having a Gram-negative microbial infection comprising administering to an individual that has been determined to have a Gram-negative microbial infection an effective amount of a pharmaceutical composition comprising: an antibiotic in an amount that is below the amount normally effective for treatment of the Gram-negative microbial infection when used alone, and a 9. The method of claim 8, wherein the Gram-negative microbe is selected from the group consisting of *E. Coli, Salmonella, Shigella, Pseudomonas, Moraxella, Helicobacter, Stenotrophomonas, Bdellovibrio, Legionella, Acinetobacter, spirochaetes, Neisseria gonorrhoeae, Neisseria meningitides, Hemophilus influenzae, Klebsiella pneumoniae, Proteus mirabilis, Enterobacter, Serratia*, and any combinations thereof.

10. The method of claim 1, wherein the silver-containing compound comprises elemental silver, a silver salt, and/or ionic silver.

11. The method of claim 1, wherein the threshold level of the silver-containing compound required to effectively treat the Gram-negative microbial infection when used alone is the minimum concentration of the silver-containing compound required by itself to reduce or inhibit the growth of microbes by at least 30%, or to kill at least about 30% of the microbes.

12. The method of claim 1, wherein the antibiotic is present in the pharmaceutical composition at a level below the normal minimum inhibitory concentration (MIC) of the antibiotic when used alone.

13. A method for delivering into a Gram-negative microbe an agent that does not penetrate across an outer membrane of the Gram-negative microbe when used alone, comprising contacting the Gram-negative microbe with an effective amount of a composition comprising the agent and a potentiating amount of a silver-containing compound, wherein the potentiating amount of the silver-containing compound is sufficient to increase membrane permeability of the Gram-negative microbe to the agent, but is below a threshold level required to inhibit or kill the Gram-negative microbe when used alone, thereby delivering the agent into the Gram-negative microbe.

14. The method of claim 13, wherein the agent is an antibiotic specific for treatment of a Gram-positive microbial infection or an optical molecule.

15. A method for treating a surface having a Gram-negative microbial biofilm comprising administering to a surface that has been determined to have a Gram-negative microbial biofilm an effective amount of a composition comprising an agent in an amount that is not normally effective for treatment of the Gram-negative microbial biofilm when used alone, and a potentiating amount of a silver-containing compound, wherein the potentiating amount of the silver-containing compound is sufficient to expand the spectrum of the agent, but not enough to be effective by itself to treat the biofilm.

16. A pharmaceutical composition for treatment of a microbial infection comprising daptomycin in an amount that is not effective by itself to treat the microbial infection, and a potentiating amount of a silver-containing compound, with a pharmaceutically acceptable carrier, wherein the potentiating amount of the silver-containing compound is sufficient to expand the spectrum of daptomycin, but is below a threshold level required to effectively treat the microbial infection when used alone.

* * * * *